US012612420B2

(12) United States Patent
Gzik et al.

(10) Patent No.: US 12,612,420 B2
(45) Date of Patent: Apr. 28, 2026

(54) ARGINASE INHIBITORS AND METHODS OF USE THEREOF

(71) Applicant: Molecure S.A., Warsaw (PL)

(72) Inventors: Anna Gzik, Wartkowice (PL); Jacek Chrzanowski, Lodz (PL); Bartlomiej Borek, Lodz (PL); Roman Blaszczyk, Lodz (PL); Jacek Olczak, Lodz (PL); Adam Golebiowski, Madison, CT (US); Marcin Mikolaj Grzybowski, Lask (PL); Paulina Pomper, Piaseczno (PL); Nazan Cemre Güner-Chalimoniuk, Laz (PL); Kamil Lisiecki, Pultusk (PL); Damian Kusmirek, Czerniewice (PL)

(73) Assignee: Molecure S.A., Warsaw (PL)

( * ) Notice: Subject to any disclaimer, the term of this patent is extended or adjusted under 35 U.S.C. 154(b) by 0 days.

(21) Appl. No.: 17/558,841

(22) Filed: Dec. 22, 2021

(65) Prior Publication Data

US 2022/0204530 A1 Jun. 30, 2022

Related U.S. Application Data

(60) Provisional application No. 63/129,215, filed on Dec. 22, 2020.

(51) Int. Cl.
C07F 5/02 (2006.01)
A61K 45/06 (2006.01)

(52) U.S. Cl.
CPC .............. C07F 5/025 (2013.01); A61K 45/06 (2013.01)

(58) Field of Classification Search
CPC .................................................... C07F 5/025
See application file for complete search history.

(56) References Cited

FOREIGN PATENT DOCUMENTS

WO      WO-2017075363 A1 *   5/2017   ............. A61K 31/69
WO      WO-2017191130 A2 *  11/2017   ........... A61K 31/133
WO      WO-2019159120 A1 *   8/2019   ............. A61K 31/69

OTHER PUBLICATIONS

Vig "Amino acids as promoieties in prodrug design and development" Advanced Drug Delivery Reviews 65 (2013) 1370-1385.*
Borek "Boronic acid-based arginase inhibitors in cancer immunotherapy" Bioorganic & Medicinal Chemistry 2020, 28, 115658, Available online Jul. 23, 2020.*
Blair, Nicholas F. "Urea cycle disorders: a life-threatening yet treatable cause of metabolic encephalopathy in adults" Pract Neurol (2015) vol. 15, pp. 45-48.
Detroja, Trishna Saha et al. "Virtual Screening for FDA-Approved Drugs That Selectively Inhibit Arginase Type 1 and 2" Molecules (2022) vol. 27, 5134, 16 pages.
Diaz, George A. et al. "The role and control of arginine levels in arginase 1 deficiency" Journal of Inherited Metabolic Disease (2023) vol. 46, pp. 3-14.
Clemente, Gonçalo S. et al. "Arginase as a Potential Biomarker of Disease Progression: A Molecular Imaging Perspective" International Journal of Molecular Sciences (2020) vol. 21, p. 5291, 36 pages.

* cited by examiner

Primary Examiner — David K O'Dell
(74) Attorney, Agent, or Firm — McDonnell Boehnen Hulbert & Berghoff LLP

(57)                    ABSTRACT

The inventive compounds are small molecule therapeutics that are potent inhibitors of arginase 1 and arginase 2 activity. The invention also provides pharmaceutical compositions comprising the compounds, and methods for using the compounds for treating or preventing a disease or condition associated with arginase activity.

10 Claims, No Drawings

ARGINASE INHIBITORS AND METHODS OF USE THEREOF

RELATED APPLICATIONS

This application claims the benefit of priority to U.S. Provisional Patent Application Ser. No. 63/129,215, filed Dec. 22, 2020, and to Polish Patent Application number P.436430, filed Dec. 22, 2020.

BACKGROUND OF THE INVENTION

Field of the Invention

This disclosure relates to small molecule therapeutic inhibitors of arginase 1 and arginase 2.

Description of Related Art

Two arginase isozymes, arginase 1 and arginase 2 (denoted also as ARG1 and ARG2) exist in mammals. Both enzymes catalyze the same biochemical reaction (hydrolysis of L-arginine into L-ornithine and urea), but they differ in cellular expression level, regulation and subcellular localization. ARG1 is a cytosolic protein and ARG2 is mainly localized in mitochondria (Jenkinson C P, Grody W W, Cederbaum S D. Comparative properties of arginases. (*Comparative biochemistry and physiology Part B, Biochemistry & Molecular Biology.* 1996; 114(1):107-132).

The arginases are implicated in various pathological states. These include, without limitation: asthma, pulmonary hypertension, hypertension, T cell dysfunction, erectile dysfunction, atherosclerosis, renal disease, ischemia reperfusion injury, neurodegenerative diseases, wound healing, inflammatory diseases, fibrotic diseases, and cancer.

Arginase expression and L-arginine depletion is known as an important immune-suppressive pathway of the mammalian immune system (Munder M. Arginase: an emerging key player in the mammalian immune system. *Br J Pharmacol.* 2009; 158(3):638-651). L-Arginine deficiency down-regulates expression of T cell receptor (TCR) ζ chain, a key signaling element of the TCR, thereby impairing T cell function (Rodriguez P C, Zea A H, Culotta K S, Zabaleta J, Ochoa J B, Ochoa A C. Regulation of T cell receptor CD3zeta chain expression by L-arginine. *J Biol Chem.* 2002; 277(24):21123-21129). Depletion of L-arginine from the tumor microenvironment leads to an arrest in T cell cycle progression, inhibition of IFN-γ production, and blocking of signaling through the T cell receptor.

Arginases are produced by myeloid-derived suppressor cells (MDSC) that are highly enriched in the tumor-bearing state (Bronte V, Serafini P, De Santo C, Marigo I, Tosello V, Mazzoni A, Segal D M, Staib C, Lowel M, Sutter G, Colombo M P, Zanovello P: IL-4-Induced Arginase 1 Suppresses Alloreactive T Cells in Tumor-Bearing Mice *J Immunol* 2003; 170:270-278). Induction of the arginase pathway is an important mechanism involved in the evasion of the anti-tumor immunity. High arginase activity has been observed in patients with various malignancies, both in blood and within tumor mass.

It was shown that T cell functions are restored and tumor growth is inhibited upon inhibition of arginase produced by tumor-associated MDSCs or tumor-infiltrating CD11b+Gr-1− mature myeloid cells in various murine tumor models (Rodriguez P C, Quiceno D G, Zabaleta J, et al. Arginase 1 production in the tumor microenvironment by mature myeloid cells inhibits T-cell receptor expression and antigen-specific T-cell responses. *Cancer Res.* 2004; 64(16): 5839-5849). Depletion of the myeloid suppressor cells re-establishes T cell activation regulated by TCR and costimulatory signals (Zea A H, Rodriguez P C, Atkins M B, et al. Arginase-producing myeloid suppressor cells in renal cell carcinoma patients: a mechanism of tumor evasion. *Cancer Res.* 2005; 65(8):3044-3048).

Arginase was shown to participate in the suppression of tumor-infiltrating lymphocytes in patients with prostate carcinoma (Bronte V, Kasic T, Gri G, et al. Boosting antitumor responses of T lymphocytes infiltrating human prostate cancers. *J Exp Med.* 2005; 201(8):1257-1268), non-small cell lung carcinoma (Rodriguez P C, Quiceno D G, Zabaleta J, et al. Arginase 1 production in the tumor microenvironment by mature myeloid cells inhibits T-cell receptor expression and antigen-specific T-cell responses. *Cancer Res.* 2004; 64(16):5839-5849) and multiple myeloma (Serafini P, Meckel K, Kelso M, et al. Phosphodiesterase-5 inhibition augments endogenous antitumor immunity by reducing myeloid-derived suppressor cell function. *J Exp Med.* 2006; 203(12):2691-2702). Not only MDSC but also dendritic cells (DCs) have been shown to suppress CD8+ T cells and antitumor immune responses through ARG1 production (Norian L A, Rodriguez P C, O'Mara L A, et al. Tumor-infiltrating regulatory dendritic cells inhibit CD8+ T cell function via L-arginine metabolism. *Cancer Res.* 2009; 69(7):3086-3094).

Arginase 1 was shown to be carried over long distances and delivered to immune cells tumor cells via extracellular vesicles (Evs), impairing antitumor immune responses. It was reported that Evs found in the ascites and plasma of OvCa patients contain ARG1 and are able to suppress proliferation of CD4+ and CD8+ T cells (Czystowska-Kuzmicz, M., Sosnowska, A., Nowis, D. et al. Small extracellular vesicles containing arginase-1 suppress T-cell responses and promote tumor growth in ovarian carcinoma. *Nat Commun* 2019; 10(1):3000).

Lowe et al. demonstrated that regulatory T cells (Tregs) preferentially express ARG2 leading to the attenuation of effector T cell proliferation which can potentially result in tumor progression, especially in metastatic melanoma (Lowe M M, Boothby I, Clancy S, et al. Regulatory T cells use arginase 2 to enhance their metabolic fitness in tissues. *JCI Insight.* 2019; 4(24):e129756. Published 2019 Dec. 19. Doi:10.1172/jci.insight.129756).

A growing body of research indicate that the pathological role of arginases in cancer, especially ARG2, is not limited to the extracellular immunosuppression driven by arginine depletion in the tumor microenvironment. It was revealed that ARG2 is a cell-intrinsic regulator of CD8+ T cell activity, antitumor cytotoxicity and immune memory formation (Marti I Lindez A A, Dunand-Sauthier I, Conti M, et al. Mitochondrial arginase-2 is a cell-autonomous regulator of CD8+ T cell function and antitumor efficacy. *JCI Insight.* 2019; 4(24):e132975. Published 2019 Nov. 21. doi: 10.1172/jci.insight.132975). Furthermore, it was shown that ARG2 in cancer cells promotes cell proliferation via polyamine synthesis and controls toxicity of ammonia, which is particularly significant in hypoxic tumors (Zaytouni, T., Tsai, P Y., Hitchcock, D. S. et al. Critical role for arginase 2 in obesity-associated pancreatic cancer. *Nat Commun* 8, 242 (2017)). The pathological role of arginase was also revealed in sickle cell disease (SCD), which is an L-arginine deficiency syndrome. Since ARG1 is present in human erythrocytes, in SCD patients it is aberrantly released in active form into plasma resulting in the impaired metabolism of L-arginine. Moreover, arginase together with hemoglobin, both released during the intravascular hemolysis, cause an abnormally high NO consumption leading to the diminished NO bioavailability. Clinically, the hemolysis and altered L-arginine metabolism contribute to the development of various SCD-related complications, i.e.: endothelial dysfunction, vaso-occlusion, pulmonary hypertension, priapism, cutaneous leg ulceration, stroke, renal dysfunction, asthma, and—ultimately—early mortality. Hence, arginase inhibitors represent a group of very promising drug candidates for the treatment of SCD (V. B. Patel et al. (eds.), L-Arginine in Clinical Nutrition, Nutrition and Health, DOI 10.1007/978-3-319-26009-9_39).

Given the role of arginase in various pathological states and their role in chronic inflammation and suppression of anti-tumor immunity, the present invention provides novel boron-containing compounds as inhibitors of arginase activity, as well as methodologies for using these compounds as therapeutics.

Numerous boron-containing arginase inhibitors are well-known from the literature. One of such inhibitors is 2(S)-amino-6-boronohexanoic acid, as described in WO 99/19295 A1, published on Apr. 22, 1999 (incorporated by reference), and in WO 08/061612 A1, published on May 29, 2008 (incorporated by reference). Besides, WO 11/133653, published on Oct. 27, 2011 (incorporated by reference), and WO 13/059437, published on Apr. 25, 2013 (incorporated by reference), describe a number of alpha-amino acid derivatives bearing a terminal B(OH)$_2$ group and a spacer, usually being a 1,3-cyclobutylene moiety. Mono- or polycyclic boron-containing amino acid compounds suitable as arginase inhibitors are described in WO 12/058065, published on May 3, 2012 (incorporated by reference). Other related patent application publications are WO 10/085797 of Jul. 29, 2010 (incorporated by reference), WO 13/158262 of Oct. 24, 2013 (incorporated by reference), WO 12/091757 of Jun. 5, 2012 (incorporated by reference), and WO 2017/191130, published on Nov. 9, 2017 (incorporated by reference).

Other related patent application publications are WO 2016/210106 A1 (published on Dec. 29, 2016); WO 2017/075363 A1 (published on May 4, 2017); WO 2018/119440 A1 (published on Jun. 28, 2018); WO 2019/120296 A1 (published on Jun. 27, 2019); WO 2019/159120 A1 (published on Aug. 22, 2019); WO 2019/173188 A1 (published on Sep. 12, 2019); WO 2019/177873 A1 (published on Sep. 19, 2019); WO 2019/186497 A1 (published on Oct. 3, 2019); WO 2019/205979 A1 (published on Oct. 31, 2019); WO 2019/245890 A1 (published on Dec. 26, 2019); WO 2020/102646 A1 (published on May 22, 2020); WO 2020/104626 A1 (published on May 28, 2020); WO 2020/131598 A1 (published on Jun. 25, 2020); WO 2020/161675 A1 (published on Aug. 13, 2020); WO 2020/160707 A1 (published on Aug. 13, 2020); WO 2020/249821 A1 (published on Dec. 17, 2020). All these patent application publications are incorporated by reference.

Significance of the substitution at the alpha center of 2-amino-6-boronohexanoic acid for the inhibitory potency of arginase 1 and arginase 2 inhibitors has been discussed (Golebiowski A., et al. 2-Substituted-2-amino-6-boronohexanoic acids as arginase inhibitors. *Bioorg. & Med. Chem. Lett.,* 2013; 23:2027-2030).

Further related publications include: Golebiowski A., et al., *Bioorg. & Med. Chem. Lett.,* 2013; 23:4837-4841; Van Zandt M. C., et al., *J. Med Chem.* 2013, 56, 6, 2568-2580; Van Zandt M. C., et al., *J. Med. Chem.* 2019, 62, 17, 8164-8177; Blaszczyk R., et al., *ACS Medicinal Chemistry Letters* 2020, 11, 4, 433-438; and Mitcheltree M. J., et al.,

*ACS Medicinal Chemistry Letters* 2020, 11, 4, 582-588. The disclosure of each of these publications is incorporated by reference herein in its entirety.

There is a need to investigate the inhibition of arginases, and to discover treatments for conditions associated with elevated expression of arginases, such as asthma, allergic responses and cancer. In particular, there is a need to explore new molecular scaffolds that effectively inhibit arginases and, therefore, can act as therapeutic agents for the treatment of these conditions.

SUMMARY OF THE INVENTION

In one aspect, the invention provides a compound represented by Formula (I):

(I)

wherein:

$R^1$ is selected from the group comprising hydrogen, straight-chain $C_1$-$C_6$ alkyl, branched $C_1$-$C_6$ alkyl, HC(O)—, straight-chain $C_1$-$C_6$ alkyl-C(O)—, and branched $C_1$-$C_6$ alkyl-C(O)—;

$R^2$ and $R^3$ are each independently selected from the group comprising hydrogen, straight-chain $C_1$-$C_6$ alkyl, branched $C_1$-$C_6$ alkyl, straight-chain $C_1$-$C_6$ alkyl-C(O)—, and branched $C_1$-$C_6$ alkyl-C(O)—;

or $R^2$ and $R^3$ taken together with the boron atom and the oxygen atoms to which they are bound form a 4-, 5-, 6-, or 7-membered heterocyclyl ring that is fully saturated or partially saturated, or $R^2$ and $R^3$ taken together with the boron atom and the oxygen atoms to which they are bound form a diester of the boronic acid and the polyol selected from, but not limited to, the group comprising pinanediol, mannitol, glycerol, xylitol, sorbitol, and erythritol, or $R^2$ and $R^3$ taken together with the boron atom and the oxygen atoms to which they are bound form an anhydride or mixed ester-anhydride of the boronic acid and hydroxy acids or dicarboxylic acids or tricarboxylic acids selected from, but not limited to, iminodiacetic acid, N-methyliminodiacetic acid, oxalic acid, malonic acid, succinic acid, glutaric acid, tartaric acid, citric acid, malic acid, aspartic acid, glutamic acid, mandelic acid, glycolic acid, lactic acid, and 3-hydroxypropionic acid;

$R^4$ is selected from the group comprising hydrogen, straight-chain $C_1$-$C_6$ alkyl, and branched $C_1$-$C_6$ alkyl;

$R^5$ is selected from the group comprising hydrogen, straight-chain $C_1$-$C_6$ alkyl, and branched $C_1$-$C_6$ alkyl;

$R^6$ and $R^7$ are each independently selected from the group comprising hydrogen, straight-chain $C_1$-$C_6$ alkyl, and branched $C_1$-$C_6$ alkyl, or $R^6$ and $R^7$ taken together with the carbon atom to which they are attached form $C_{3-6}$ cycloalkyl ring;

$R^8$ is selected from the group comprising the residues of D and L alpha-amino acids including, but not limited to, alanine, arginine, asparagine, aspartic acid, citrulline, cysteine, glutamine, glutamic acid, histidine, isoleucine, leucine, tert-leucine, lysine, methionine, norvaline, ornithine, phenylalanine, pyrrolysine, selenocysteine, selenomethionine, serine, threonine, tryptophan, tyrosine, and valine, and also from the residues of glycine, D-proline, and L-proline, (R)- and (S)-2-amino-2-cyclopentylacetic acid, (R)- and (S)-2-amino-3-hydroxy-3-methylbutanoic acid, and (R)- and (S)-2-amino-2,3-dimethylbutanoic acid; and $R^9$ is selected from the group comprising hydrogen, straight-chain $C_1$-$C_6$ alkyl, and branched $C_1$-$C_6$ alkyl;

or a tautomer, stereoisomer, pharmaceutically acceptable salt, and/or a solvate thereof.

Also provided herein are pharmaceutical compositions, comprising (i) a therapeutically effective amount of at least one compound of the invention, or a tautomer, stereoisomer, pharmaceutically acceptable salt, and/or a solvate thereof; and (ii) a pharmaceutically acceptable carrier, vehicle or excipient therefor.

In another aspect, the invention provides a method for inhibiting arginase 1, arginase 2, or a combination thereof in a cell, comprising contacting the cell with at least one compound according to the invention, or a tautomer, stereoisomer, pharmaceutically acceptable salt, and/or a solvate thereof.

In another aspect, the invention provides a method for the treatment or prevention of a disease or condition associated with expression or activity of arginase 1, arginase 2, or a combination thereof in a subject, comprising administering to the subject a therapeutically effective amount of at least one compound according to the invention, or a tautomer, stereoisomer, pharmaceutically acceptable salt, and/or a solvate thereof.

In another aspect, the invention provides use of at least one compound according to the invention, or a tautomer, stereoisomer, pharmaceutically acceptable salt, and/or a solvate thereof in the manufacture of a medicament for the treatment or prevention of a disease or condition associated with expression or activity of arginase 1, arginase 2, or a combination thereof.

In another aspect, the invention provides at least one compound according to the invention, or a tautomer, stereoisomer, pharmaceutically acceptable salt, and/or a solvate thereof, for the treatment or prevention of a disease or condition associated with expression or activity of arginase 1, arginase 2, or a combination thereof.

In another aspect, the invention provides at least one compound according to the invention, or a tautomer, stereoisomer, pharmaceutically acceptable salt, and/or a solvate thereof, for use in the treatment or prevention of a disease or condition selected from the group consisting of cardiovascular disorders, sexual disorders, wound healing disorders, gastrointestinal disorders, autoimmune disorders, immune disorders, infections, pulmonary disorders, hemolytic disorders, and cancers.

In another aspect, the invention provides use of at least one compound according to the invention, or a tautomer, stereoisomer, pharmaceutically acceptable salt, and/or a solvate thereof, for protecting an organ during transport.

DETAILED DESCRIPTION

The present invention is based on a surprising finding that some small molecule arginase inhibitors possess very high activity accompanied by superior pharmacokinetics.

Definitions

The articles "a" and "an" are used herein to refer to one or to more than one (i.e., to at least one) of the grammatical object of the article. By way of example, "an element" means one element or more than one element.

The terms used herein may be preceded and/or followed by a single dash "-", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, $(C_1$-$C_6)$-alkoxycarbonyloxy and —OC(O)O($C_1$-$C_6$)alkyl indicate the same functionality; similarly arylalkyl and -alkylaryl indicate the same functionality.

The terms "hydrogen", "hydrogen atom", and symbol "H", as used herein in the context of substituents to Markush formulas, such as Formula (I), (Ia), and (Ib), denote a hydrogen atom attached to the remaining part of the molecule or group in question. For the sake of simplicity, hydrogen atoms attached to carbon atoms are not shown in the structural formulas; each carbon atom is understood to be associated with enough hydrogen atoms to give the carbon atom four bonds.

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer, or preferably 1-6 carbons. Representative examples of alkyl include, but are not limited to, methyl, ethyl, n-propyl, isopropyl, n-butyl, sec-butyl, isobutyl, tert-butyl, n-pentyl, isopentyl, neopentyl, and n-hexyl.

The term "cycloalkyl" or "carbocyclyl" means monocyclic saturated or partially saturated carbocyclic rings, having from 3-6 carbon atoms in their ring structure. Examples of monocyclic cycloalkyls include cyclopropyl, cyclobutyl, cyclopentyl, cyclopentenyl, cyclohexyl, and cyclohexenyl. Cycloalkyl groups are optionally substituted.

The term "heterocyclyl" as used herein refers to a radical of a non-aromatic ring system, including, monocyclic rings, which can be completely saturated or which can contain one or more units of unsaturation, for the avoidance of doubt, the degree of unsaturation does not result in an aromatic ring system, and having 3 to 7 atoms including at least one heteroatom, such as nitrogen, oxygen, or sulfur. More preferred heterocycloalkyl groups have from 5-7 ring members where from 1-4 of the ring members are hetero atoms selected from the group comprising O, N, and S, the remaining ring atoms being C. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, azepinyl, azepanyl, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocyclyl group is optionally substituted by one or more substituents as described below.

The term "heteroatom" is art-recognized, and includes an atom of any element other than carbon or hydrogen. Illustrative heteroatoms include boron, nitrogen, oxygen, phosphorus, sulfur and selenium, or alternatively oxygen, nitrogen and sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight-chain or branched chain hydrocarbon radical containing from 2 to 6 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, and 5-hexenyl. The unsaturated bond(s) of the alkenyl group can be located anywhere in the moiety and can have either the (Z) or the (E) configuration about the double bond(s).

The term "amino" is a term of art and as used herein refers to both unsubstituted and substituted amines, e.g., a moiety that may be represented by the general formulas:

wherein $R_a$, $R_b$, and $R_c$ each independently represent a hydrogen, an alkyl, an alkenyl, $-(CH_2)_x-R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, or a heterocyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or $-(CH_2)_x-R_d$.

In certain embodiments, the term "amino" refers to $-NH_2$.

The term "alpha-amino acid" is a term of art, including, but not limited to, any one of 20 canonical alpha-amino acids, including their D- and L-isomers; and also glycine, as well as D- and L-proline (being, in fact, imino acids). The three-letter codes, trivial names, and systematic names of residues of these amino acids (L isomer series assumed) are as follows:

| Ala | alanyl | (S)-2-aminopropanoyl; |
|---|---|---|
| Arg | arginyl | (S)-2-amino-5-guanidinopentanoyl; |
| Asn | asparaginyl | (S)-2,4-diamino-4-oxobutanoyl; |
| Asp | aspartyl | (S)-2-amino-3-carboxypropanoyl; |
| Cys | cysteinyl | (R)-2-amino-3-mercaptopropanoyl; |
| Gln | glutaminyl | (S)-2,5-diamino-5-oxopentanoyl; |
| Glu | glutamyl | (S)-2-amino-4-carboxybutanoyl; |
| Gly | glycyl | 2-aminoacetyl; |
| His | histidyl | (S)-2-amino-3-(1H-imidazol-4-yl)propanoyl; |
| Ile | isoleucyl | (2S,3S)-2-amino-3-methylpentanoyl; |
| Leu | leucyl | (S)-2-amino-4-methylpentanoyl; |
| Lys | lysyl | (S)-2,6-diaminohexanoyl; |
| Met | methionyl | (S)-2-amino-4-(methylthio)butanoyl; |
| Phe | phenylalanyl | (S)-2-amino-3-phenylpropanoyl; |
| Pro | prolyl | (S)-pyrrolidine-2-carboxyl; |
| Ser | seryl | (S)-2-amino-3-hydroxypropanoyl; |
| Thr | threonyl | (2S,3R)-2-amino-3-hydroxybutanoyl; |
| Trp | tryptophanyl | (S)-2-amino-3-(1H-indol-3-yl)propanoyl; |
| Tyr | tyrosyl | (S)-2-amino-3-(4-hydroxyphenyl)propanoyl; |
| Val | valyl | (S)-2-amino-3-methylbutanoyl. |

Other alpha-amino acid residues mentioned in this disclosure are, for example,

| tert-Leu | tert-leucyl | (S)-2-amino-3,3-dimethylbutanoyl; |
|---|---|---|
| Nva | norvalyl | (S)-2-aminopentanoyl; |
| Orn | ornithyl | (S)-2,5-diaminopentanoyl; |
| Pyl | pyrrolysyl | (S)-2-amino-6-{[(2R,3R)-3-methyl-3,4-dihydro-2H-pyrrol-2-yl]carbonylamino}hexanoyl; |
| Sec | selenocysteinyl | (R)-2-amino-3-selanylpropanoyl; |
| SeMet | selenomethionyl | (S)-2-amino-4-(methylselanyl)butanoyl; |
| Cit | citrullinyl | (S)2-amino-5-(carbamoylamino)pentanoyl; |
| | | (S)-2-amino-2-cyclopentylacetyl; |
| | | (S)-2-amino-3-hydroxy-3-methylbutanoyl; and |
| | | (S)-2-amino-2,3-dimethylbutanoyl. |

The term "hydroxy acid", as used herein, means an organic molecule bearing both at least one carboxy group and at least one hydroxy group. Examples of hydroxy acids include glycolic acid, lactic acid, and citric acid.

The term "dicarboxylic acid", as used herein, means an organic molecule bearing two carboxy groups. Examples of dicarboxylic acids include oxalic acid, malonic acid, succinic acid, maleic acid, glutaric acid, and adipic acid.

The term "tricarboxylic acid", as used herein, means an organic molecule bearing three carboxy groups. Examples of tricarboxylic acids include citric acid, isocitric acid, aconitic acid, and propane-1,2,3-tricarboxylic acid.

The term "amido", as used herein, means $-NHC(=O)-$, wherein the amido group is bound to the parent molecular moiety through the nitrogen. Examples of amido include alkylamido such as $CH_3C(=O)N(H)-$ and $CH_3CH_2C(=O)N(H)-$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "azide" or "azido", as used herein, means an —N₃ group.

The term "carbonyl" as used herein refers to —C(=O)—.

The term "thiocarbonyl" as used herein refers to —C(=S)—.

The term "alkylthio" as used herein refers to alkyl-S—.

The term "carboxy", as used herein, means a —CO₂H group.

The term "aryl" is a term of art and as used herein refers to includes monocyclic, bicyclic and polycyclic aromatic hydrocarbon groups, for example, benzene, naphthalene, anthracene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. Representative examples of the polycyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to a phenyl group.

The term "heteroaryl" is a term of art and as used herein refers to a monocyclic, bicyclic, and polycyclic aromatic group having 3 to 14, 5 to 14, or 3 to 12 total atoms including one or more heteroatoms such as nitrogen, oxygen, or sulfur in the ring structure. More preferred heteroaryl groups have from 5-10 ring members where from 1-4 of the ring members are hetero atoms selected from the group comprising O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl(C₁-C₆)alkyl" is a term of art and as used herein refers to an alkyl group, for example a C₁-C₆ alkyl group, substituted with an aryl group, wherein the moiety is appended to the parent molecule through the alkyl group.

The term "heteroaralkyl", "heteroarylalkyl", or "heteroaryl(C₁-C₆)alkyl" is a term of art and as used herein refers to an alkyl group, for example a C₁-C₆ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH—CH_2—O—$) and vinyloxy (i.e., $CH_2=CH—O—$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The terms "cyano" and "nitrile" are terms of art and as used herein refer to —CN.

The term "nitro", as used herein, means —NO$_2$.

The terms "halo" and "halogen" are terms of art and as used herein refer to —F, —Cl, —Br, or —I.

The term "haloalkyl" as used herein refers to an alkyl group, as defined herein, wherein some or all of the hydrogens are replaced with halogen atoms. The term "haloalkoxyl" refers to an alkoxy group, as defined herein, wherein some or all of the hydrogens are replaced with halogen atoms. An exemplary haloalkyl group is trifluoromethyl.

The terms "hydroxy" and "hydroxyl" are a term of art and as used herein refer to —OH.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "polyol", as used herein, denotes an organic compound containing more than one hydroxy group, an no other functional groups. Representative examples of polyols include, but are not limited to, glycerol, erythritol, xylitol, sorbitol, mannitol, and pinanediol.

Certain compounds contained in compositions of the present invention may exist in particular geometrical isomer or stereoisomeric forms. In addition, compounds of the present invention may also be optically active. The present invention contemplates all such compounds, including cis- and trans-isomers, (R)- and (S)-enantiomers, diastereoisomers, D-isomers, L-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or other substituents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2$^{nd}$* ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

An "unsaturated" or "partially saturated" compound means that the referenced chemical structure may contains on or more multiple carbon-carbon bonds, but is not aromatic. For example, an unsaturated cycloalkyl group as defined herein includes cyclohexenyl, cyclopentenyl, cyclohexadienyl, and the like.

For purposes of the invention, the chemical elements are identified in accordance with the Periodic Table of the Elements, CAS version, *Handbook of Chemistry and Physics,* 67th ed., 1986-87, inside cover.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

The chemical structure of examples that are a mixture of diastereoisomers or a single diastereoisomer but with unknown relative configuration are drawn and named without defined stereochemical configuration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, pamoic (embonic), succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula (I). As another example, the salt may comprise less than one inorganic or organic acid molecule per molecule of base, such as two molecules of compound of Formula (I) per molecule of tartaric acid.

The compounds according to the invention, e.g., the compounds of Formula (I), can form solvates with a stoichiometric or non-stoichiometric amount of one or more solvents, such as water, ethanol, diethyl ether, or ethyl acetate. The solvates formed with water ale called hydrates.

As used herein, a protic solvent is a solvent that has a hydrogen atom bound to an oxygen atom (as in a hydroxyl group) or a nitrogen atom (as in an amine group). In general terms, any solvent that contains labile $H^+$ is called a protic solvent. The molecules of such solvents readily donate protons ($H^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, tert-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) *Harrison's Principles of Internal Medicine* 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). Thus, in certain aspects, the disclosure encompasses non-prophylactic treatment, i.e., therapeutic treatment.

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In one aspect, the invention provides a compound represented by Formula (I):

(I)

wherein:

$R^1$ is selected from the group comprising hydrogen, straight-chain $C_1$-$C_6$ alkyl, branched $C_1$-$C_6$ alkyl, HC(O)—, straight-chain $C_1$-$C_6$ alkyl-C(O)—, and branched $C_1$-$C_6$ alkyl-C(O)—;

$R^2$ and $R^3$ are each independently selected from the group comprising hydrogen, straight-chain $C_1$-$C_6$ alkyl, branched $C_1$-$C_6$ alkyl, straight-chain $C_1$-$C_6$ alkyl-C(O)—, and branched $C_1$-$C_6$ alkyl-C(O)—;

or $R^2$ and $R^3$ taken together with the boron atom and the oxygen atoms to which they are bound form a 4-, 5-, 6-, or 7-membered heterocyclyl ring that is fully saturated or partially saturated, or $R^2$ and $R^3$ taken together with the boron atom and the oxygen atoms to which they are bound form a diester of the boronic acid and the polyol selected from, but not limited to, the group comprising pinanediol, mannitol, glycerol, xylitol, sorbitol, and erythritol, or $R^2$ and $R^3$ taken together with the boron atom and the oxygen atoms to which they are bound form an anhydride or mixed ester-anhydride of the boronic acid and hydroxy acids or dicarboxylic acids or tricarboxylic acids selected from, but not limited to, iminodiacetic acid, N-methyliminodiacetic acid, oxalic acid, malonic acid, succinic acid, glutaric acid, tartaric acid, citric acid, malic acid, aspartic acid, glutamic acid, mandelic acid, glycolic acid, lactic acid, and 3-hydroxypropionic acid;

$R^4$ is selected from the group comprising hydrogen, straight-chain $C_1$-$C_6$ alkyl, and branched $C_1$-$C_6$ alkyl;

$R^5$ is selected from the group comprising hydrogen, straight-chain $C_1$-$C_6$ alkyl, and branched $C_1$-$C_6$ alkyl;

$R^6$ and $R^7$ are each independently selected from the group comprising hydrogen, straight-chain $C_1$-$C_6$ alkyl, and branched $C_1$-$C_6$ alkyl, or $R^6$ and $R^7$ taken together with the carbon atom to which they are attached form $C_{3-6}$ cycloalkyl ring;

$R^8$ is selected from the group comprising the residues of D- and L-alpha-amino acids including, but not limited to, alanine, arginine, asparagine, aspartic acid, citrulline, cysteine, glutamine, glutamic acid, histidine, isoleucine, leucine, tert-leucine, lysine, methionine, norvaline, ornithine, phenylalanine, pyrrolysine, selenocysteine, selenomethionine, serine, threonine, tryptophan, tyrosine, and valine, and also from the residues of glycine, D-proline, and L-proline, (R)- and (S)-2-amino-2-cyclopentylacetic acid, (R)- and (S)-2-amino-3-hydroxy-3-methylbutanoic acid, and (R)- and (S)-2-amino-2,3-dimethylbutanoic acid; and $R^9$ is selected from the group comprising hydrogen, straight-chain $C_1$-$C_6$ alkyl, and branched $C_1$-$C_6$ alkyl;

or a tautomer, stereoisomer, pharmaceutically acceptable salt, and/or a solvate thereof.

The above-defined general Formula (I) covers certain compounds of the invention, which can be described in more detail as follows.

In certain embodiments, the compounds of Formula (I) according to the invention have the structure of Formula (Ia):

(Ia)

In certain embodiments, the compounds of Formula (I) according to the invention have the structure of Formula (Ib):

(Ib)

A person skilled in the art readily recognizes that, in Formula (Ib), the substituents $R^5$, $R^6$, and $R^7$ all denote hydrogen atoms, so they are not shown in the structure for the sake of simplicity.

In certain embodiments, the compound according to the invention has the structure of Formula (I) or (Ia), wherein:

$R^1$ is hydrogen, methyl, or ethyl;

preferably $R^1$ is hydrogen or methyl;

$R^2$ is hydrogen;

$R^3$ is hydrogen, or $R^2$ and $R^3$ taken together with the boron atom and the oxygen atoms to which they are bound form a mixed ester-anhydride of the boronic acid and citric acid;

$R^4$ is hydrogen or methyl;

$R^5$ is hydrogen or methyl;

$R^6$ is hydrogen or methyl;

$R^7$ is hydrogen or methyl;

or $R^6$ and $R^7$ combine with the carbon atom to which they are attached to form cyclopropane ring;

$R^8$ is selected from the group comprising D-alanyl, L-alanyl, L-arginyl, L-asparaginyl, glycyl, L-histidyl, L-isoleucyl, L-leucyl, L-tert-leucyl, L-lysyl, L-methionyl, L-norvalyl, L-phenylalanyl, L-prolyl, L-seryl, L-threonyl, L-tryptophanyl, L-tyrosyl, D-valyl, L-valyl, (S)-2-amino-2-cyclopentylacetyl, (S)-2-amino-3-hydroxy-3-methylbutyryl, and (S)-2-amino-2,3-dimethylbutyryl; and $R^9$ is hydrogen or methyl.

In certain embodiments, the compound according to the invention has the structure of Formula (I) or (Ia) or (Ib), wherein:

$R^1$ is hydrogen;

$R^2$ is hydrogen;

$R^3$ is hydrogen;

$R^4$ is hydrogen;

$R^5$ is hydrogen;

$R^6$ is hydrogen;

$R^7$ is hydrogen;

$R^8$ is selected from the group comprising D-alanyl, L-alanyl, L-arginyl, L-asparaginyl, glycyl, L-histidyl, L-isoleucyl, L-leucyl, L-tert-leucyl, L-lysyl, L-methionyl, L-norvalyl, L-phenylalanyl, L-prolyl, L-seryl, L-threonyl, L-tryptophanyl, L-tyrosyl, D-valyl, L-valyl, (S)-2-amino-2-cyclopentylacetyl, (S)-2-amino-3-hydroxy-3-methylbutyryl, and (S)-2-amino-2,3-dimethylbutyryl; and $R^9$ is hydrogen or methyl.

In certain embodiments, the compound according to the invention is:

(1R,2S,5R)-1-amino-2-(((S)-2-aminopropanamido)methyl)-5-(2-boronoethyl)cyclohexane-1-carboxylic acid;

(1R,2S,5R)-1-amino-2-(((S)-2-amino-3-methylbutanamido)methyl)-5-(2-boronoethyl)cyclohexane-1-carboxylic acid;

(1R,2S,5R)-1-amino-2-(((S)-2-amino-3-phenylpropanamido)methyl)-5-(2-boronoethyl)cyclohexane-1-carboxylic acid;

(1R,2S,5R)-1-amino-2-((2-aminoacetamido)methyl)-5-(2-boronoethyl)cyclohexane-1-carboxylic acid;

(1R,2S,5R)-1-amino-5-(2-boronoethyl)-2-(((S)-pyrrolidine-2-carboxamido)methyl)cyclohexane-1-carboxylic acid;

(1R,2S,5R)-1-amino-2-(((S)-2-amino-4-methylpentanamido)methyl)-5-(2-boronoethyl)cyclohexane-1-carboxylic acid;

(1R,2S,5R)-1-amino-2-(((S)-2-amino-3-hydroxypropanamido)methyl)-5-(2-boronoethyl)cyclohexane-1-carboxylic acid;

(1R,2S,5R)-1-amino-2-(((S)-2-amino-3-(1H-imidazol-4-yl)propanamido)methyl)-5-(2-boronoethyl)cyclohexane-1-carboxylic acid (1R,2S,5R)-1-amino-5-(2-boronoethyl)-2-(((S)-2,6-diaminohexanamido)methyl)cyclohexane-1-carboxylic acid;

(1R,2S,5R)-1-amino-2-(((2S,3S)-2-amino-3-methylpentanamido)methyl)-5-(2-boronoethyl)cyclohexane-1-carboxylic acid;

(1R,2S,5R)-1-amino-2-(((S)-2-amino-2-cyclopentylacetamido)methyl)-5-(2-boronoethyl)cyclohexane-1-carboxylic acid;

(1R,2S,5R)-1-amino-2-(((S)-2-amino-3,3-dimethylbutanamido)methyl)-5-(2-boronoethyl)cyclohexane-1-carboxylic acid;

(1R,2S,5R)-1-amino-2-(((S)-2-amino-5-guanidinopentanamido)methyl)-5-(2-boronoethyl)cyclohexane-1-carboxylic acid;

(1R,2S,5R)-1-amino-2-(((S)-2-amino-3-(4-hydroxyphenyl)propanamido)methyl)-5-(2-boronoethyl)cyclohexane-1-carboxylic acid;

(1R,2S,5R)-1-amino-5-(2-boronoethyl)-2-(((S)-2,4-diamino-4-oxobutanamido)methyl)cyclohexane-1-carboxylic acid;

(1R,2S,5R)-1-amino-2-(((S)-2-amino-3-hydroxy-3-methylbutanamido)methyl)-5-(2-boronoethyl)cyclohexane-1-carboxylic acid;

(1R,2S,5R)-1-amino-2-(((S)-2-amino-4-(methylthio)butanamido)methyl)-5-(2-boronoethyl)cyclohexane-1-carboxylic acid;

(1R,2S,5R)-1-amino-2-(((S)-2-amino-3-(1H-indol-3-yl)propanamido)methyl)-5-(2-boronoethyl)cyclohexane-1-carboxylic acid;

(1R,2S,5R)-1-amino-2-(((2S,3R)-2-amino-3-hydroxybutanamido)methyl)-5-(2-boronoethyl)cyclohexane-1-carboxylic acid;

(1R,2S,5R)-1-amino-2-(((S)-2-aminopentanamido)methyl)-5-(2-boronoethyl)cyclohexane-1-carboxylic acid;

(1R,2S,5R)-1-amino-2-((2-amino-2,3-dimethylbutanamido)methyl)-5-(2-boronoethyl)cyclohexane-1-carboxylic acid;

(1R,2S,5R)-1-amino-2-(((R)-2-aminopropanamido)methyl)-5-(2-boronoethyl)cyclohexane-1-carboxylic acid;

(1R,2S,5R)-1-amino-2-(((R)-2-amino-3-methylbutanamido)methyl)-5-(2-boronoethyl)cyclohexane-1-carboxylic acid;

(1R,2S,5R)-1-amino-2-(((S)-2-amino-N-methylpropanamido)methyl)-5-(2-boronoethyl)cyclohexane-1-carboxylic acid;

(1R,2S,5R)-1-amino-2-(((S)-2-amino-N,3-dimethylbutanamido)methyl)-5-(2-boronoethyl)cyclohexane-1-carboxylic acid;

(1R,2S,5R)-1-amino-2-(((R)-2-amino-3-(1-methyl-1H-indol-3-yl)propanamido)methyl)-5-(2-boronoethyl)cyclohexane-1-carboxylic acid;

(1R,2S,5R)-1-amino-2-(((R)-2-amino-3-mercaptopropanamido)methyl)-5-(2-boronoethyl)cyclohexane-1-carboxylic acid;

(1R,2S,5R)-1-amino-5-(2-boronoethyl)-2-(((S)-2,5-diamino-5-oxopentanamido)methyl)cyclohexane-1-carboxylic acid;

(1R,2S,5R)-1-amino-2-(((S)-2-amino-3-carboxypropanamido)methyl)-5-(2-boronoethyl)cyclohexane-1-carboxylic acid;

(1R,2S,5R)-1-amino-2-(((S)-2-amino-4-carboxybutanamido)methyl)-5-(2-boronoethyl)cyclohexane-1-carboxylic acid;

(1R,2S,5R)-1-amino-5-(2-boronoethyl)-2-((2-(methylamino)acetamido)methyl)cyclohexane-1-carboxylic acid;

(2-((1R,3R,4S)-3-amino-4-(((S)-2-amino-3-methylbutanamido)methyl)-3-(methoxycarbonyl)cyclohexyl)ethyl)boronic acid;

2-(2-((1R,3R,4S)-3-amino-4-(((S)-2-amino-3-methylbutanamido)methyl)-3-carboxycyclohexyl)ethyl)-4-(carboxymethyl)-6-oxo-1,3,2-dioxaborinane-4-carboxylic acid;

(1R,2R,5R)-1-amino-2-(((S)-2-amino-3-methylbutanamido)methyl)-5-(2-boronoethyl)cyclohexane-1-carboxylic acid;

(1R,2S,5R)-2-(((S)-2-aminopropanamido)methyl)-5-(2-boronoethyl)-1-(ethylamino)cyclohexane-1-carboxylic acid; or (1R,2S,5R)-2-(((S)-2-aminopropanamido)methyl)-5-(2-boronoethyl)-1-(methylamino)cyclohexane-1-carboxylic acid;

or a tautomer, stereoisomer, pharmaceutically acceptable salt, and/or a solvate thereof.

In some preferred embodiments, the compound according to the invention is:

(1R,2S,5R)-1-amino-2-((2-aminoacetamido)methyl)-5-(2-boronoethyl)cyclohexane-1-carboxylic acid;

(1R,2S,5R)-1-amino-5-(2-boronoethyl)-2-(((S)-pyrrolidine-2-carboxamido)methyl)cyclohexane-1-carboxylic acid;

(1R,2S,5R)-1-amino-2-(((S)-2-amino-4-methylpentana-mido)methyl)-5-(2-boronoethyl)cyclohexane-1-carbox-ylic acid;

(1R,2S,5R)-1-amino-5-(2-boronoethyl)-2-(((S)-2,6-di-aminohexanamido)methyl)cyclohexane-1-carboxylic acid;

(1R,2S,5R)-1-amino-2-(((2S,3S)-2-amino-3-methylpen-tanamido)methyl)-5-(2-boronoethyl)cyclohexane-1-car-boxylic acid;

(1R,2S,5R)-1-amino-2-(((S)-2-amino-2-cyclopentylacet-amido)methyl)-5-(2-boronoethyl)cyclohexane-1-carbox-ylic acid;

(1R,2S,5R)-1-amino-2-(((S)-2-amino-3,3-dimethylbutana-mido)methyl)-5-(2-boronoethyl)cyclohexane-1-carbox-ylic acid;

(1R,2S,5R)-1-amino-2-(((S)-2-amino-5-guanidinopentana-mido)methyl)-5-(2-boronoethyl)cyclohexane-1-carbox-ylic acid;

(1R,2S,5R)-1-amino-2-(((S)-2-amino-4-(methylthio)bu-tanamido)methyl)-5-(2-boronoethyl)cyclohexane-1-car-boxylic acid;

(1R,2S,5R)-1-amino-2-(((S)-2-aminopentanamido)methyl)-5-(2-boronoethyl)cyclohexane-1-carboxylic acid;

(1R,2S,5R)-1-amino-2-(((R)-2-aminopropanamido) methyl)-5-(2-boronoethyl)cyclohexane-1-carboxylic acid; or (1R,2S,5R)-1-amino-2-(((S)-2-amino-3-methylbutanamido) methyl)-5-(2-boronoethyl)cyclohexane-1-carboxylic acid;

or a tautomer, stereoisomer, pharmaceutically acceptable salt, and/or a solvate thereof.

The following representative structures are disclosed herein:

| Example No. | Compound Structure | Compound Name |
|---|---|---|
| 1 | | (1R,2S,5R)-1-amino-2-(((S)-2-aminopropanamido)methyl)-5-(2-boronoethyl)cyclohexane-1-carboxylic acid |
| 2 | | (1R,2S,5R)-1-amino-2-(((S)-2-amino-3-methylbutanamido)methyl)-5-(2-boronoethyl)cyclohexane-1-carboxylic acid |
| 3 | | (1R,2S,5R)-1-amino-2-(((S)-2-amino-3-phenylpropanamido)methyl)-5-(2-boronoethyl)cyclohexane-1-carboxylic acid |
| 4 | | (1R,2S,5R)-1-amino-2-((2-amino-acetamido)methyl)-5-(2-boronoethyl)cyclohexane-1-carboxylic acid |
| 5 | | (1R,2S,5R)-1-amino-5-(2-boronoethyl)-2-(((S)-pyrrolidine-2-carboxamido)methyl)cyclohexane-1-carboxylic acid |
| 6 | | (1R,2S,5R)-1-amino-2-(((S)-2-amino-4-methylpentanamido)methyl)-5-(2-boronoethyl)cyclohexane-1-carboxylic acid |

-continued

| Example No. | Compound Structure | Compound Name |
|---|---|---|
| 7 | | (1R,2S,5R)-1-amino-2-(((S)-2-amino-3-hydroxypropanamido)methyl)-5-(2-boronoethyl)cyclohexane-1-carboxylic acid |
| 8 | | (1R,2S,5R)-1-amino-2-(((S)-2-amino-3-(1H-imidazol-4-yl)propanamido)methyl)-5-(2-boronoethyl)cyclohexane-1-carboxylic acid |
| 9 | | (1R,2S,5R)-1-amino-5-(2-boronoethyl)-2-(((S)-2,6-diaminohexanamido)methyl)cyclohexane-1-carboxylic acid |
| 10 | | (1R, 2S, 5R)-1-amino-2-(((2S,3S)-2-amino-3-methylpentanamido)methyl)-5-(2-boronoethyl)cyclohexane-1-carboxylic acid |
| 11 | | (1R,2S,5R)-1-amino-2-(((S)-2-amino-2-cyclopentylacetamido)methyl)-5-(2-boronoethyl)cyclohexane-1-carboxylic acid |
| 12 | | (1R,2S,5R)-1-amino-2-(((S)-2-amino-3,3-dimethylbutanamido)methyl)-5-(2-boronoethyl)cyclohexane-1-carboxylic acid |
| 13 | | (1R,2S,5R)-1-amino-2-(((S)-2-amino-5-guanidinopentanamido)methyl)-5-(2-boronoethyl)cyclohexane-1-carboxylic acid |
| 14 | | (1R,2S,5R)-1-amino-2-(((S)-2-amino-3-(4-hydroxyphenyl)propanamido)methyl)-5-(2-boronoethyl)cyclohexane-1-carboxylic acid |
| 15 | | (1R,2S,5R)-1-amino-5-(2-boronoethyl)-2-(((S)-2,4-diamino-4-oxobutanamido)methyl)cyclohexane-1-carboxylic acid |

-continued

| Example No. | Compound Structure | Compound Name |
|---|---|---|
| 16 | | (1R,2S,5R)-1-amino-2-(((S)-2-amino-3-hydroxy-3-methylbutanamido)methyl)-5-(2-boronoethyl)cyclohexane-1-carboxylic acid |
| 17 | | (1R,2S,5R)-1-amino-2-(((S)-2-amino-4-(methylthio)butanamido)methyl)-5-(2-boronoethyl)cyclohexane-1-carboxylic acid |
| 18 | | (1R,2S,5R)-1-amino-2-(((S)-2-amino-3-(1H-indol-3-yl)propanamido)methyl)-5-(2-boronoethyl)cyclohexane-1-carboxylic acid |
| 19 | | (1R,2S,5R)-1-amino-2-(((2S,3R)-2-amino-3 -hydroxybutanamido)methyl)-5-(2-boronoethyl)cyclohexane-1-carboxylic acid |
| 20 | | (1R,2S,5R)-1-amino-2-(((S)-2-aminopentanamido)methyl)-5-(2-boronoethyl)cyclohexane-1-carboxylic acid |
| 21 | | (1R,2S,5R)-1-amino-2-((2-amino-2,3-dimethylbutanamido)methyl)-5-(2-boronoethyl)cyclohexane-1-carboxylic acid |
| 22 | | (1R,2S,5R)-1-amino-2-(((R)-2-aminopropanamido)methyl)-5-(2-boronoethyl)cyclohexane-1-carboxylic acid |
| 23 | | (1R,2S,5R)-1-amino-2-(((R)-2-amino-3-methylbutanamido)methyl)-5-(2-boronoethyl)cyclohexane-1-carboxylic acid |
| 24 | | (1R,2S,5R)-1-amino-2-(((S)-2-amino-N-methylpropanamido)methyl)-5-(2-boronoethyl)cyclohexane-1-carboxylic acid |

| Example No. | Compound Structure | Compound Name |
|---|---|---|
| 25 | | (1R,2S,5R)-1-amino-2-(((S)-2-amino-N,3-dimethylbutanamido)methyl)-5-(2-boronoethyl)cyclohexane-1-carboxylic acid |
| 26 | | (1R,2S,5R)-1-amino-2-(((R)-2-amino-3-(1-methyl-1H-indol-3-yl)propanamido)methyl)-5-(2-boronoethyl)cyclohexane-1-carboxylic acid |
| 27 | | (1R,2S,5R)-1-amino-2-(((R)-2-amino-3-mercaptopropanamido)methyl)-5-(2-boronoethyl)cyclohexane-1-carboxylic acid |
| 28 | | (1R,2S,5R)-1-amino-5-(2-boronoethyl)-2-(((S)-2,5-diamino-5-oxopentanamido)methyl)cyclohexane-1-carboxylic acid |
| 29 | | (1R,2S,5R)-1-amino-2-(((S)-2-amino-3-carboxypropanamido)methyl)-5-(2-boronoethyl)cyclohexane-1-carboxylic acid |
| 30 | | (1R,2S,5R)-1-amino-2-(((S)-2-amino-4-carboxybutanamido)methyl)-5-(2-boronoethyl)cyclohexane-1-carboxylic acid |
| 31 | | (1R,2S,5R)-1-amino-5-(2-boronoethyl)-2-((2-(methylamino)acetamido)methyl)cyclohexane-1-carboxylic acid |
| 32 | | (2-((1R,3R,4S)-3-amino-4-(((S)-2-amino-3-methylbutanamido)methyl)-3-(methoxycarbonyl)cyclohexyl)ethyl)boronic acid |

-continued

| Example No. | Compound Structure | Compound Name |
| --- | --- | --- |
| 33 | | 2-(2-((1R,3R,4S)-3-amino-4-(((S)-2-amino-3-methylbutanamido)methyl)-3-carboxycyclohexyl)ethyl)-4-(carboxymethyl)-6-oxo-1,3,2-dioxaborinane-4-carboxylic acid |
| 34 | | (1R,2R,5R)-1-amino-2-(((S)-2-amino-3-methylbutanamido)methyl)-5-(2-boronoethyl)cyclohexane-1-carboxylic acid |
| 35 | | (1R,2S,5R)-2-(((S)-2-aminopropanamido)methyl)-5-(2-boronoethyl)-1-(ethylamino)cyclohexane-1-carboxylic acid |
| 36 | | (1R,2S,5R)-2-(((S)-2-aminopropanamido)methyl)-5-(2-boronoethyl)-1-(methylamino)cyclohexane-1-carboxylic acid |

In certain embodiments, the disclosed compounds can be in the form of pharmaceutically acceptable salts. For example, the representative hydrochloride salts of the disclosed compounds can be:

x 2 HCl x 2 HCl

-continued x 2 HCl x 2 HCl x 2 HCl

29 x 2 HCl x 2 HCl x 3 HCl x 3 HCl x 2 HCl x 2 HCl x 2 HCl x 3 HCl x 2 HCl

30 x 2 HCl x 2 HCl x 2 HCl x 2 HCl x 2 HCl x 2 HCl x 2 HCl x 2 HCl x 2 HCl 31            32

-continued           -continued x 2 HCl x 2 HCl x 2 HCl x 2 HCl x 2 HCl x 2 HCl x 2 HCl x 2 HCl x 2 HCl x 2 HCl x 2 HCl x 2 HCl Pharmaceutical Compositions of the Invention In another aspect, the invention provides a pharmaceutical composition comprising (i) a therapeutically effective amount of at least one compound of the invention, or a tautomer, stereoisomer, pharmaceutically acceptable salt, and/or a solvate thereof, and (ii) a pharmaceutically acceptable carrier, vehicle or excipient therefor. In general, pharmaceutical compositions comprise (i) a therapeutically effective amount of at least one compound of the invention, or a tautomer, stereoisomer, pharmaceutically acceptable salt, and/or a solvate thereof; and (ii) a pharmaceutically acceptable carrier, vehicle or excipient therefor, including, but not limited to, bioavailability enhancers, penetration enhancers, biopolymers, PLGA-based nanoparticles, sugar-based nanoparticles, coating to avoid the deleterious effects of the stomach environment, either by protection of the compound of the invention or derivative thereof, or by release of the biologically active material beyond the stomach environment, such as in the intestine.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituxan, PD4 inhibitors, p38 inhibitors, PDE4 inhibitors, and antihistamines, immunotherapeutic agents, including checkpoint inhibitors such as PD-1, PD-L1 or CTLA-4 inhibitors and IDO/TDO inhibitors, immunosuppressants, agents affecting interleukins, cytokines and chemokine, kinase inhibitors, chemotherapeutic agents including alkylating antineoplastic agents, antimetabolites, anti-microtubule agents, topoisomerase inhibitors, cytotoxic antibiotics or targeted therapies such as antibodies, antibodies drug conjugates, cell-based immunotherapies, nanoparticles, anti-cancer vaccines and radiotherapy.

In some embodiments, the one or more additional chemotherapeutic agents includes aminoglutethimide, amsacrine, anastrozole, asparaginase, AZD5363, Bacillus Calmette-Guerin vaccine (BCG), bicalutamide, bleomycin, bortezomib, buserelin, busulfan, camptothecin, capecitabine, carboplatin, carfilzomib, carmustine, chlorambucil, chloroquine, cisplatin, cladribine, clodronate, cobimetinib, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, erlotinib, estradiol, estramustine, etoposide, everolimus, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, lenalidomide, letrozole, leucovorin, leuprolide, levamisole, lomustine, lonidamine, mechlorethamine, medroxyprogesterone, megestrol, melphalan, mercaptopurine, mesna, metformin, methotrexate, miltefosine, mitomycin, mitotane, mitoxantrone, MK-2206, nilutamide, nocodazole, octreotide, olaparib, oxaliplatin, paclitaxel, pamidronate, pazopanib, pentostatin, perifosine, plicamycin, pomalidomide, porfimer, procarbazine, raltitrexed, rituximab, rucaparib, selumetinib, sorafenib, streptozocin, sunitinib, suramin, talazoparib, tamoxifen, temozolomide, temsirolimus, teniposide, testosterone, thalidomide, thioguanine, thiotepa, titanocene dichloride, topotecan, trametinib, trastuzumab, tretinoin, veliparib, vinblastine, vincristine, vindesine, or vinorelbine.

In some embodiments, the one or more additional chemotherapeutic agents includes abagovomab, adecatumumab, afutuzumab, anatumomab, mafenatox, apolizumab, blinatumomab, catumaxomab, durvalumab, epratuzumab, inotuzumab, ozogamicin, intelumumab, ipilimumab, isatuximab, lambrolizumab, nivolumab, ocaratuzumab, olatatumab, pembrolizumab, pidilizumab, ticilimumab, samalizumab or tremelimumab.

In some embodiments, the one or more additional immunotherapeutic agents includes epacadostat, GDC-0919, 1-methyl-D-tryptophan, BMS-986205 or PF-06840003.

In some embodiments, the one or more additional chemotherapeutic agents includes ipilimumab, nivolumab, pembrolizumab or pidilizumab.

In other embodiments, the method further comprises administering one or more non-chemical methods of cancer treatment, such as radiation therapy, surgery, thermoablation, focused ultrasound therapy, cryotherapy, or a combination thereof.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "*Soluble Polymer-Enzyme Adducts*", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal, oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Cin Invest* 84:1145-1146 (a-1-proteinase);

Oswein et al., 1990, "*Aerosolization of Proteins*", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluenesulfonic, tartaric, citric, methane sulfonic, formic, malonic, succinic, naphthalene-2-sulfonic, and benzenesulfonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, non-erodible, biodegradable, or non-biodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bio-erodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly (hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions, methods, and uses described herein are readily apparent from the description of the invention contained herein in view of information known to the ordinarily skilled artisan, and may be made without departing from the scope of the invention or any embodiment thereof.

Methods of the Invention

Another aspect of the invention is a method for inhibiting arginase 1, arginase 2, or a combination thereof in a cell, comprising contacting the cell with at least one compound according to the invention, or a tautomer, stereoisomer, pharmaceutically acceptable salt, and/or a solvate thereof.

In another aspect, the invention provides a method for the treatment or prevention of a disease or condition associated with expression or activity of arginase 1, arginase 2, or a combination thereof in a subject, comprising administering to the subject a therapeutically effective amount of at least one compound according to the invention, or a tautomer, stereoisomer, pharmaceutically acceptable salt, and/or a solvate thereof.

In certain embodiments, the disease or condition is selected from the group consisting of cardiovascular disorders, sexual disorders, wound healing disorders, gastrointestinal disorders, autoimmune disorders, immune disorders, infections, pulmonary disorders, hemolytic disorders, and cancers.

In certain embodiments, the disease or condition is a cardiovascular disorder selected from the group consisting of systemic hypertension, pulmonary arterial hypertension (PAH), pulmonary arterial hypertension in high altitude, ischemia reperfusion (IR) injury, myocardial infarction, atherosclerosis.

In certain embodiments, the cardiovascular disorder is pulmonary arterial hypertension (PAH).

In certain embodiments, the cardiovascular disorder is ischemia reperfusion (IR) injury selected from the group consisting of liver IR, kidney IR, and myocardial IR.

In certain embodiments, the cardiovascular disorder is myocardial infarction or atherosclerosis.

In certain embodiments, the disease or condition is a sexual disorder selected from the group consisting of Peyronie's disease and erectile dysfunction.

In certain embodiments, the disease or condition is a wound healing disorder selected from the group consisting of infected and uninfected wound healing.

In certain embodiments, the disease or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease or condition is an autoimmune disorder is selected from the group consisting of encephalomyelitis, multiple sclerosis, anti-phospholipid syndrome 1, autoimmune hemolytic anemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture syndrome.

In certain embodiments, the disease or condition is an immune disorder selected from the group consisting of myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction.

In certain embodiments, the disease or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the pulmonary disorder is pulmonary hypertension.

In certain embodiments, the pulmonary disorder is asthma.

In certain embodiments, the disease or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

In certain embodiments, the hemolytic disorder is sickle-cell disease.

In certain embodiments, the disease or condition is a cancer selected from the group consisting of gastric cancer, gastroesophageal junction cancer, colorectal cancer, pancreatic cancer, liver cancer, breast cancer, brain tumor, non-small cell lung carcinoma, renal cell carcinoma, prostate carcinoma, multiple myeloma, acute and chronic leukemias, T cell, B cell and NK cell lymphomas, neuroblastoma, glioblastoma, astrocytoma, squamous-cell carcinomas of the head and neck, and melanoma.

In certain embodiments, the disease or condition is a cancer selected from the group consisting of chronic lymphocytic leukemia, acute lymphoblastic leukemia, chronic myelogenous leukemia, acute myeloid leukemia, adrenocortical carcinoma, anal cancer, appendix cancer, atypical teratoid/rhabdoid tumor, basal cell carcinoma, bile duct cancer, bladder cancer, bone cancer, brain and spinal cord tumor, brain stem glioma, central nervous system atypical teratoid/rhabdoid tumor, central nervous system embryonal tumors, breast cancer, bronchial tumors, Burkitt lymphoma, carcinoid tumor, carcinoma of unknown primary, central nervous system cancer, cervical cancer, childhood cancers, chordoma, chronic myeloproliferative disorders, colon cancer, craniopharyngioma, cutaneous T-cell lymphoma, ductal carcinoma in situ, embryonal tumors, endometrial cancer, ependymoblastoma, ependymoma, esophageal cancer, esthesioneuroblastoma, Ewing sarcoma, extracranial germ cell tumor, extrahepatic bile duct cancer, eye cancer, fibrous histiocytoma of bone, gallbladder cancer, gastric cancer, gastrointestinal carcinoid tumor, gastrointestinal stromal tumors, germ cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular cancer, histiocytosis, Langerhans cell cancer, Hodgkin lymphoma, hypopharyngeal cancer, intraocular melanoma, islet cell tumors, Kaposi sarcoma, kidney cancer, Langerhans cell histiocytosis, laryngeal cancer, lip and oral cavity cancer, lobular carcinoma in situ, lymphoma, AIDS-related lymphoma, macroglobulinemia, male breast cancer, medulloblastoma, medulloepithelioma, Merkel cell carcinoma, malignant mesothelioma, metastatic squamous neck cancer with occult primary, midline tract carcinoma involving nut gene, mouth cancer, multiple endocrine neoplasia syndrome, plasma cell neoplasm, mycosis fungoides, myeloma, chronic myeloproliferative disorder, nasal cavity cancer, paranasal sinus cancer, nasopharyngeal cancer, non-Hodgkin lymphoma, oral cancer, oral cavity cancer, lip cancer, oropharyngeal cancer, osteosarcoma, ovarian cancer, papillomatosis, paraganglioma, paranasal sinus cancer, nasal cavity cancer, parathyroid cancer, penile cancer, pharyngeal cancer, pheochromocytoma, pineal parenchymal tumors of intermediate differentiation, pineoblastoma, pituitary tumor, plasma cell neoplasm, pleuropulmonary blastoma, primary central nervous system lymphoma, rectal cancer, renal cell cancer, renal pelvis cancer, ureter cancer, transitional cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer with occult primary, supratentorial primitive neuroectodermal tumors, testicular cancer, throat cancer, thymoma, thymic carcinoma, thyroid cancer, transitional cell cancer of the renal pelvis and ureter, gestational trophoblastic tumor, unknown primary, unusual cancer of childhood, urethral cancer, uterine cancer, uterine sarcoma, Waldenström macroglobulinemia, and Wilms tumor.

In certain embodiments, the method of treatment further comprises administering to the subject of one or more other therapeutic agent(s) selected from the group consisting of steroids, membrane stabilizers, 5LO inhibitors, leukotriene synthesis and receptor inhibitors, inhibitors of IgE isotype switching or IgE synthesis, IgG isotype switching or IgG synthesis, β-agonists, tryptase inhibitors, aspirin, COX inhibitors, methotrexate, anti-TNF drugs, rituximab, p38 inhibitors, PDE4 inhibitors, and antihistamines, immunotherapeutic agents, including checkpoint inhibitors such as PD-1, PD-L1, CTLA-4, LAG-3, TIM-3, TIGIT, VISTA inhibitors, IDO/TDO inhibitors, adenosine A2A receptor antagonists, ectonucleotidase (CD73 and CD39) inhibitors, immunosuppressants, agents affecting interleukins, cytokines and chemokines, kinase inhibitors, chemotherapeutic agents including alkylating antineoplastic agents, antimetabolites, anti-microtubule agents, topoisomerase inhibitors, cytotoxic antibiotics or targeted therapies such as antibodies, antibodies drug conjugates, cell-based immunotherapies, nanoparticles, anti-cancer vaccines, and radiotherapy, prior to, simultaneously with, or after administration of the at least one compound according to the invention, or a tautomer, stereoisomer, pharmaceutically acceptable salt, and/or a solvate thereof.

In certain embodiments, the subject is a mammal selected from the group consisting of human, dog, cat, horse, cow, pig, sheep, goat, and ape.

Uses of the Invention

In another aspect, the invention provides use of a compound according to the invention, or a tautomer, stereoisomer, pharmaceutically acceptable salt, and/or a solvate thereof in the manufacture of a medicament for the treatment or prevention of a disease or condition associated with expression or activity of arginase 1, arginase 2, or a combination thereof.

In another aspect, the invention provides a compound according to the invention, or a tautomer, stereoisomer, pharmaceutically acceptable salt, and/or a solvate thereof, for use in the treatment or prevention of a disease or condition associated with expression or activity of arginase 1, arginase 2, or a combination thereof.

In another aspect, the invention provides a compound according to the invention, or a tautomer, stereoisomer, pharmaceutically acceptable salt, and/or a solvate thereof, for use in the treatment or prevention of a disease or condition selected from the group consisting of cardiovascular disorders, sexual disorders, wound healing disorders, gastrointestinal disorders, autoimmune disorders, immune disorders, infections, pulmonary disorders, hemolytic disorders, and cancers.

In certain embodiments, the disease or condition is selected from the group consisting of cardiovascular disorders, sexual disorders, wound healing disorders, gastrointestinal disorders, autoimmune disorders, immune disorders, infections, pulmonary disorders, hemolytic disorders, and cancers.

In certain embodiments, the disease or condition is a cardiovascular disorder selected from the group consisting of systemic hypertension, pulmonary arterial hypertension (PAH), pulmonary arterial hypertension in high altitude, ischemia reperfusion (IR) injury, myocardial infarction, atherosclerosis.

In certain embodiments, the cardiovascular disorder is pulmonary arterial hypertension (PAH).

In certain embodiments, the cardiovascular disorder is ischemia reperfusion (IR) injury selected from the group consisting of liver IR, kidney IR, and myocardial IR.

In certain embodiments, the cardiovascular disorder is myocardial infarction or atherosclerosis.

In certain embodiments, the disease or condition is a sexual disorder selected from the group consisting of Peyronie's disease and erectile dysfunction.

In certain embodiments, the disease or condition is a wound healing disorder selected from the group consisting of infected and uninfected wound healing.

In certain embodiments, the disease or condition is a gastrointestinal disorder selected from the group consisting of gastrointestinal motility disorders, gastric cancers, inflammatory bowel disease, Crohn's disease, ulcerative colitis, and gastric ulcers.

In certain embodiments, the disease or condition is an autoimmune disorder is selected from the group consisting of encephalomyelitis, multiple sclerosis, anti-phospholipid syndrome 1, autoimmune hemolytic anemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture syndrome.

In certain embodiments, the disease or condition is an immune disorder selected from the group consisting of myeloid-derived suppressor cell (MDSC) mediated T-cell dysfunction, human immunodeficiency virus (HIV), autoimmune encephalomyelitis, and ABO mismatch transfusion reaction.

In certain embodiments, the disease or condition is myeloid-derived suppressor cell (MDSC) mediated T-cell dysfunction.

In certain embodiments, the disease or condition is a pulmonary disorder selected from the group consisting of chemically-induced lung fibrosis, idiopathic pulmonary fibrosis, cystic fibrosis, chronic obstructive pulmonary disease (COPD), and asthma.

In certain embodiments, the pulmonary disorder is pulmonary hypertension.

In certain embodiments, the pulmonary disorder is asthma.

In certain embodiments, the disease or condition is a hemolytic disorder selected from the group consisting of sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

In certain embodiments, the hemolytic disorder is sickle-cell disease.

In certain embodiments, the disease or condition is a cancer selected from the group consisting of gastric cancer, gastroesophageal junction cancer, colorectal cancer, pancreatic cancer, liver cancer, breast cancer, brain tumor, non-small cell lung carcinoma, renal cell carcinoma, prostate carcinoma, multiple myeloma, acute and chronic leukemias, T cell, B cell and NK cell lymphomas, neuroblastoma, glioblastoma, astrocytoma, squamous-cell carcinomas of the head and neck, and melanoma.

In certain embodiments, the disease or condition is a cancer selected from the group consisting of chronic lymphocytic leukemia, acute lymphoblastic leukemia, chronic myelogenous leukemia, acute myeloid leukemia, adrenocortical carcinoma, anal cancer, appendix cancer, atypical teratoid/rhabdoid tumor, basal cell carcinoma, bile duct cancer, bladder cancer, bone cancer, brain and spinal cord tumor, brain stem glioma, central nervous system atypical teratoid/rhabdoid tumor, central nervous system embryonal tumors, breast cancer, bronchial tumors, Burkitt lymphoma, carcinoid tumor, carcinoma of unknown primary, central nervous system cancer, cervical cancer, childhood cancers, chordoma, chronic myeloproliferative disorders, colon cancer, craniopharyngioma, cutaneous T-cell lymphoma, ductal carcinoma in situ, embryonal tumors, endometrial cancer, ependymoblastoma, ependymoma, esophageal cancer, esthesioneuroblastoma, Ewing sarcoma, extracranial germ cell tumor, extrahepatic bile duct cancer, eye cancer, fibrous histiocytoma of bone, gallbladder cancer, gastric cancer, gastrointestinal carcinoid tumor, gastrointestinal stromal tumors, germ cell tumor, extracranial germ cell tumor, extragonadal germ cell tumor, ovarian germ cell tumor, gestational trophoblastic tumor, glioma, hairy cell leukemia, head and neck cancer, heart cancer, hepatocellular cancer, histiocytosis, Langerhans cell cancer, Hodgkin lymphoma, hypopharyngeal cancer, intraocular melanoma, islet cell tumors, Kaposi sarcoma, kidney cancer, Langerhans cell histiocytosis, laryngeal cancer, lip and oral cavity cancer, lobular carcinoma in situ, lymphoma, AIDS-related lymphoma, macroglobulinemia, male breast cancer, medulloblastoma, medulloepithelioma, Merkel cell carcinoma, malignant mesothelioma, metastatic squamous neck cancer with occult primary, midline tract carcinoma involving nut gene, mouth cancer, multiple endocrine neoplasia syndrome, plasma cell neoplasm, mycosis fungoides, myeloma, chronic myeloproliferative disorder, nasal cavity cancer, paranasal sinus cancer, nasopharyngeal cancer, non-Hodgkin lymphoma, oral cancer, oral cavity cancer, lip cancer, oropharyngeal cancer, osteosarcoma, ovarian cancer, papillomatosis, paraganglioma, paranasal sinus cancer, nasal cavity cancer, parathyroid cancer, penile cancer, pharyngeal cancer, pheochromocytoma, pineal parenchymal tumors of intermediate differentiation, pineoblastoma, pituitary tumor, plasma cell neoplasm, pleuropulmonary blastoma, primary central nervous system lymphoma, rectal cancer, renal cell cancer, renal pelvis cancer, ureter cancer, transitional cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer with occult primary, supratentorial primitive neuroectodermal tumors, testicular cancer, throat cancer, thymoma, thymic carcinoma, thyroid cancer, transitional cell cancer of the renal pelvis and ureter, gestational trophoblastic tumor, unknown primary, unusual cancer of childhood, urethral cancer, uterine cancer, uterine sarcoma, Waldenström macroglobulinemia, and Wilms tumor.

In another aspect, the invention provides use of a compound according to the invention, or a tautomer, stereoisomer, pharmaceutically acceptable salt, and/or a solvate thereof, for protecting an organ during transport.

EXAMPLES

The present invention is further illustrated by the following examples, which in no way should be construed as limiting the scope of the claimed invention.

Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the method of synthesis. All variable groups of these methods are as described in the generic description if they are not specifically defined below.

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

For the more specific guidance concerning the synthetic approach to boron bearing alpha-amino acids, the reader is referred to the international patent application publications WO 11/133653 (incorporated by reference), WO 13/059437 (incorporated by reference), WO 17/075363, WO 16/108707, WO 17/191130.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are in J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by literature methods.

All solvents, substrates and reagents that were commercially available were used without further purification. TLC analysis was performed using pre-coated glass plates (TLC silica gel 60 F$_{254}$) from Merck. Column chromatography was performed using high-purity grade silica gel (pore size 60 Å, 230-400 mesh particle size, 40-63 µm particle size) from Merck.

Preparative HPLC were performed on LC-20AP Shimadzu with ELSD-LTII detector equipped with Luna 21.2/ 250 mm, 5 µm C18(2) 100 Å LC column.

$^{1}$H and $^{13}$C NMR spectra were recorded on Bruker AVANCE II PLUS (Ultra Shield) NMR spectrometer at 700 MHz.

All spectra were recorded in appropriate deuterated solvents (CDCl$_3$, DMSO-d$_6$, D$_2$O, CD$_3$OD, etc.) that were commercially available.

Resonances are given in parts per million relative to tetramethylsilane. Data are reported as follows: chemical shift, multiplicity (s=singlet, d=doublet, t=triplet, m=multiplet, bs=broad singlet), coupling constants (Hz) and integration.

ESI-MS spectra were obtained on a Shimadzu LC-20AD LPG separation module with a SPD-M20A UV detector and LCMS-2020 mass detector equipped with Kinetex 2.1/30 mm, 1.7 µm XB-C18 100 Å LC column eluted with 1 mL/min flow of 10-90% gradient (over 3 min) of acetonitrile in water.

Abbreviations used are those conventional in the art or the following: Ac=acetyl, aq=aqueous, Bn=benzyl, Boc=tert-butoxycarbonyl, t-Bu=tert-butyl, ° C.=degree Celsius, Cod=1,5-cyclooctadiene, DCE=1,2-dichloroethane, DCM=dichloromethane, DMF=N,N-dimethylformamide, DMSO=dimethyl sulfoxide, dppe=1,2-bis(diphenylphosphino)ethane, ELSD=evaporative light scattering detector, EtOAc or AcOEt=ethyl acetate, EtOH=ethanol, ESI+ MS=electrospray ionization mass spectrometry (in the positive ion mode), ESI-MS=electrospray ionization mass spectrometry (in the negative ion mode), g=gram, h=hour(s), HMPA=hexamethylphosphoramide, HPLC=high pressure liquid chromatography, K=kelvin, L=liter, LCMS=liquid chromatography and mass spectrometry, MeCN=acetonitrile, MeOH=methanol, min=minutes, mL=milliliter(s), M=molar, m/z=mass to charge ratio, nM=nanomolar, NMR=nuclear magnetic resonance, N=normal, OSu=N-oxysuccinimidyl, pin=pinacol, RT or rt=room temperature, TEA=triethylamine, TFA=trifluoroacetic acid, THF=tetrahydrofuran, TMSCl=chlorotrimethylsilane.

If not otherwise defined, purity of a solid substance is expressed as a ratio of the weight of the component in question to the total weight, multiplied by 100 (weight %); purity of a liquid is expressed as a ratio of the volume of the component in question to the total volume, multiplied by 100 (volume %); concentration of a solution is expressed as a ratio of the weight of the solute (in grams) to the total volume (in mL) of the solution, multiplied by 100 (w/v %). Yield of a reaction is expressed as a ratio of the weight of the product in question to the theoretical yield of this product, multiplied by 100(%). Composition of a mixed solvent is expressed as a proportion of volume parts of the component solvents (e.g., 3:1).

Exemplary general synthetic methodologies for making compounds of Formula (I) are provided below.

Example 1. (1R,2S,5R)-1-Amino-2-(((S)-2-amino-propanamido)methyl)-5-(2-boronoethyl)cyclo-hexane-1-carboxylic acid dihydrochloride Step A. (1R,2S,5R)-1-Acetamido-N-(tert-butyl)-2-((dibenzylamino)methyl)-5-vinylcyclohexane-1-carboxamide To a solution of ethyl (1R,2R,4R)-2-acetamido-2-(tert-butylcarbamoyl)-4-vinylcyclohexane-1-carboxylate (the compound was synthesized according to procedure from U.S. Pat. No. 10,391,077 B2) (1.05 g, 3.10 mmol) in dry DCM (42 mL) a solution of 1 M DIBAL-H in DCM (9.62 mL, 9.62 mmol) was added dropwise at −78° C. under argon. After 0.5 h of stirring at this temperature, the reaction mixture was quenched with glacial acetic acid (0.89 mL, 15.51 mmol) and was stirred at −78° C. for 10 min. Then, N,N-dibenzylamine (0.9 mL, 4.65 mmol) was added dropwise and cooling bath was removed. After 15 min sodium triacetoxyborohydride (2.63 g, 12.41 mmol) was added portionwise and the resulting mixture was allowed to warm to room temperature and was stirred for 2 h. 1 M HCl (30 mL) was added at 0° C. to the reaction mixture, and it was stirred for 15 min. The layers were separated and the organic layer was washed with 5% NaHCO$_3$ (1×30 mL), brine (1×30 mL), dried over Na$_2$SO$_4$, filtered and concentrated in vacuo. The residue was purified by silica gel flash chromatography (hexane/AcOEt 15:1 to 12:1) to give the corresponding product (0.66 g, 45% yield, colorless oil). ESI+MS: m/z=476.15 (M+1)+; ESI-MS: m/z=474.20 (M−1)⁻. ¹H NMR (700 MHz, chloroform-d) δ 9.13 (s, 1H), 8.14 (s, 1H), 7.38-7.20 (m, 10H), 5.69 (ddd, J=17.1, 10.4, 6.5 Hz, 1H), 4.96-4.88 (m, 2H), 3.85 (d, J=13.1 Hz, 2H), 3.73 (dd, J=13.8, 9.1 Hz, 1H), 3.18 (d, J=13.1 Hz, 2H), 3.16-3.12 (m, 1H), 2.23-2.15 (m, 2H), 2.02-1.95 (m, 1H), 1.85 (s, 3H), 1.80-1.74 (m, 1H), 1.66-1.57 (m, 1H), 1.51-1.42 (m, 1H), 1.18 (s, 9H), 1.15-1.08 (m, 2H).

Step B. (1R,2S,5R)-1-Acetamido-N-(tert-butyl)-2-((dibenzylamino)methyl)-5-(2-(4,4,5,5-tetramethyl-1,3,2-dioxaborolan-2-yl)ethyl)cyclohexane-1-car-boxamide A mixture of dppe (33 mg, 0.08 mmol) and bis(1,5-cyclooctadiene)diiridium(I) dichloride (28 mg, 0.04 mmol) in DCM (5 mL) was flushed with argon (bubbling). Subsequently, the separately prepared solution of (1R,2S,5R)-1-acetamido-N-(tert-butyl)-2-((dibenzylamino)methyl)-5-vi-nylcyclohexane-1-carboxamide (0.66 g, 1.39 mmol) in 5 mL of DCM was added successively. Finally, 4,4,5,5-tetram-ethyl-1,3,2-dioxaborolane (0.30 mL, 2.08 mmol) was added dropwise to the reaction mixture and it was stirred at room temperature overnight. The reaction mixture was diluted with DCM (30 mL) and washed with 5% NaHCO$_3$ (1×30 mL). The organic layer was dried over Na$_2$SO$_4$, filtered and concentrated in vacuo. The crude product was purified by column chromatography on silica gel (hexane/AcOEt 15:1 to 3:1) to give the corresponding product (0.74 mg, 88% yield, colorless oil). ESI+MS: m/z=604.20 (M+1)+; ESI-MS: m/z=601.90 (M−1)⁻. ¹H NMR (700 MHz, chloroform-d) δ 9.08 (s, 1H), 8.14 (s, 1H), 7.32-7.21 (m, 10H), 3.83 (d, J=13.1 Hz, 2H), 3.73 (dd, J=13.8, 9.1 Hz, 1H), 3.17 (d, J=13.1 Hz, 2H), 3.12 (dt, J=13.2, 2.1 Hz, 1H), 2.17-2.14 (m, 1H), 2.10 (qd, J=13.3, 4.4 Hz, 1H), 1.84 (s, 3H), 1.76-1.70 (m, 1H), 1.63-1.55 (m, 2H), 1.46-1.39 (m, 1H), 1.31-1.25 (m, 2H), 1.22 (s, 12H), 1.16 (s, 9H), 0.95-0.87 (m, 2H), 0.82-0.74 (m, 1H), 0.71-0.66 (m, 1H).

Step C. (1R,2S,5R)-1-Amino-5-(2-boronoethyl)-2-((dibenzylamino)methyl)cyclohexane-1-carboxylic acid dihydrochloride A mixture of (1R,2S,5R)-1-acetamido-N-(tert-butyl)-2-((dibenzylamino)methyl)-5-(2-(4,4,5,5-tetramethyl-1,3,2-dioxaborolan-2-yl)ethyl)cyclohexane-1-carboxamide (0.52 g, 0.86 mmol) and 12 M HCl$_{aq}$ (10 mL) was heated at 120° C. for 3 h. The reaction mixture was concentrated under reduced pressure and the residue was purified by preparative HPLC (1-50% of acetonitrile in water) to give the corre-sponding product (0.38 g, 89% yield, white solid). ESI+MS: m/z=425.05 (M+1)+; ESI-MS: m/z=423.05 (M−1)⁻. ¹H NMR (700 MHz, deuterium oxide) δ 7.78-7.34 (m, 10H), 4.72-4.56 (m, 2H), 4.50-4.14 (m, 2H), 3.46 (dd, J=13.7, 2.4 Hz, 1H), 3.25 (dd, J=13.6, 11.1 Hz, 1H), 2.32-2.20 (m, 2H), 1.88-1.78 (m, 2H), 1.67-1.59 (m, 1H), 1.51-1.42 (m, 1H), 1.37-1.29 (m, 3H), 0.95-0.88 (m, 1H), 0.78 (dd, J=9.4, 7.0 Hz, 2H).

Step D. (1R,2S,5R)-1-Amino-2-(aminomethyl)-5-(2-boronoethyl)cyclohexane-1-carboxylic acid dihydrochloride To a solution of (1R,2S,5R)-1-amino-5-(2-boronoethyl)-2-((dibenzylamino)methyl)cyclohexane-1-carboxylic acid dihydrochloride (0.60 g, 1.21 mmol) in MeOH (25 mL) under argon, Pd(OH)$_2$/C (20%, 200 mg) was added. The mixture was degassed, charged with H$_2$, and stirred for 2 days at room temperature. The reaction mixture was filtered through a pad of Celite, washed with MeOH (2×10 mL) and the filtrate was concentrated in vacuo to give the corresponding product (0.38 g, 99% yield, white solid). ESI+MS: m/z=244.95 (M+1)$^+$; ESI-MS: m/z=243.15 (M–1)$^-$. $^1$H NMR (700 MHz, deuterium oxide) δ 3.37 (dd, J=13.2, 3.1 Hz, 1H), 3.00 (dd, J=13.2, 10.1 Hz, 1H), 2.32 (d, J=13.1 Hz, 1H), 2.09-2.04 (m, 1H), 2.01-1.96 (m, 2H), 1.87-1.73 (m, 2H), 1.44-1.32 (m, 3H), 1.06-0.97 (m, 1H), 0.83 (dd, J=9.0, 7.4 Hz, 2H).

Step E. (1R,2S,5R)-1-Amino-5-(2-boronoethyl)-2-(((S)-2-((tert-butoxycarbonyl)amino)propanamido)methyl)cyclohexane-1-carboxylic acid To a stirred solution of (1R,2S,5R)-1-amino-2-(aminomethyl)-5-(2-boronoethyl)cyclohexane-1-carboxylic acid dihydrochloride (63 mg, 0.20 mmol) in DMF (3.5 mL), Boc-L-Ala-OSu (63 mg, 0.22 mmol) and TEA (0.14 mL, 1 mmol) were added and the resulting mixture was stirred at room temperature overnight. DMF was evaporated under reduced pressure and the residue purified by preparative HPLC (1-50% of acetonitrile in water) to give the corresponding product (58 mg, 68% yield, white solid). ESI+MS: m/z=415.95 (M+1)$^+$; ESI-MS: m/z=414.00 (M–1)$^-$. $^1$H NMR (700 MHz, methanol-d$_4$) δ 4.00 (q, J=7.2 Hz, 1H), 3.60-3.56 (m, 1H), 2.89 (dd, J=13.6, 8.2 Hz, 1H), 2.23-2.16 (m, 1H), 2.04-1.80 (m, 4H), 1.74-1.67 (m, 1H), 1.49 (s, 9H), 1.34-1.28 (m, 5H), 1.13 (t, J=12.5 Hz, 1H), 0.90-0.78 (m, 3H).

Step F. (1R,2S,5R)-1-Amino-2-(((S)-2-aminopropanamido)methyl)-5-(2-boronoethyl)cyclohexane-1-carboxylic acid dihydrochloride 4.5 M HCl in dioxane (4 mL) was added to (1R,2S,5R)-1-amino-5-(2-boronoethyl)-2-(((S)-2-((tert-butoxycarbonyl)

amino)propanamido)methyl)cyclohexane-1-carboxylic acid (50 mg, 0.12 mmol) and the resulting mixture was stirred at room temperature for 1.5 h. Then the reaction mixture was concentrated and the residue was purified by preparative HPLC (0.1-10% of acetonitrile in water) to give the corresponding product (36 mg, 77% yield, white solid). ESI+MS: m/z=315.90 (M+1)$^+$; ESI-MS: m/z=314.00 (M–1)$^-$. $^1$H NMR (700 MHz, deuterium oxide) δ 4.10 (q, J=7.1 Hz, 1H), 3.63 (dd, J=13.9, 2.7 Hz, 1H), 3.10 (dd, J=13.9, 9.4 Hz, 1H), 2.29 (d, J=11.6 Hz, 1H), 1.98-1.86 (m, 3H), 1.85-1.72 (m, 2H), 1.56 (d, J=7.1 Hz, 3H), 1.42-1.28 (m, 3H), 0.95 (qd, J=13.1, 3.4 Hz, 1H), 0.82 (dd, J=9.4, 6.9 Hz, 2H).

Example 2. (1R,2S,5R)-1-Amino-2-(((S)-2-amino-3-methylbutanamido)methyl)-5-(2-boronoethyl)cyclohexane-1-carboxylic acid dihydrochloride Step A. (1R,2S,5R)-1-Amino-5-(2-boronoethyl)-2-(((S)-2-((tert-butoxycarbonyl)amino)-3-methylbutanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (41 mg, 0.13 mmol), Boc-L-Val-OSu (45 mg, 0.14 mmol), TEA (90 μL, 0.65 mmol) and DMF (2.3 mL). The residue was purified by preparative HPLC (1-60% of acetonitrile in water) to give the corresponding product (36 mg, 63% yield, white solid). ESI+MS: m/z=443.95 (M+1)$^+$; ESI-MS: m/z=442.05 (M–1)$^-$. $^1$H NMR (700 MHz, methanol-d$_4$) δ 3.80 (d, J=6.4 Hz, 1H), 3.62 (dd, J=13.8, 2.9 Hz, 1H), 2.88 (dd, J=13.7, 8.4 Hz, 1H), 2.21-2.17 (m, 1H), 2.06-1.82 (m, 5H), 1.72-1.67 (m, 1H), 1.49 (s, 9H), 1.34-1.29 (m, 2H), 1.11 (t, J=12.5 Hz, 1H), 1.01-0.94 (m, 6H), 0.89-0.77 (m, 3H).

Step B. (1R,2S,5R)-1-Amino-2-(((S)-2-amino-3-methylbutanamido)methyl)-5-(2-boronoethyl)cyclohexane-1-carboxylic acid dihydrochloride The title compound was obtained in the same manner as in Example 1, step F, using (1R,2S,5R)-1-amino-5-(2-boronoethyl)-2-(((S)-2-((tert-butoxycarbonyl)amino)-3-methylbutanamido)methyl)cyclohexane-1-carboxylic acid (32 mg, 0.07 mmol) and 4.5 M HCl in dioxane (3 mL). The crude material was purified by preparative HPLC (0.1-3% of acetonitrile in water) to give the corresponding product (18 mg, 60% yield, white solid). ESI+MS: m/z=343.90 (M+1)+; ESI-MS: m/z=342.00 (M−1)−. $^1$H NMR (700 MHz, deuterium oxide) δ 3.82 (d, J=5.9 Hz, 1H), 3.71 (dd, J=13.8, 2.7 Hz, 1H), 3.04 (dd, J=13.8, 10.0 Hz, 1H), 2.34-2.19 (m, 2H), 1.97-1.72 (m, 5H), 1.38 (dd, J=15.2, 7.3 Hz, 2H), 1.33 (t, J=12.8 Hz, 1H), 1.06 (dd, J=6.9, 1.4 Hz, 6H), 0.98-0.91 (m, 1H), 0.86-0.78 (m, 2H).

Example 3. (1R,2S,5R)-1-Amino-2-(((S)-2-amino-3-phenylpropanamido)methyl)-5-(2-boronoethyl)cyclohexane-1-carboxylic acid dihydrochloride x 2 HCl

Step A. (1R,2S,5R)-1-Amino-5-(2-boronoethyl)-2-(((S)-2-((tert-butoxycarbonyl)amino)-3-phenylpropanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (41 mg, 0.13 mmol), Boc-L-Phe-OSu (52 mg, 0.14 mmol), TEA (90 μL, 0.65 mmol) and DMF (2.3 mL). The residue was purified by preparative HPLC (1-60% of acetonitrile in water) to give the corresponding product (38 mg, 60% yield, white solid). ESI+MS: m/z=492.15 (M+1)+; ESI-MS: m/z=490.10 (M−1)−. $^1$H NMR (700 MHz, methanol-d$_4$) δ 7.38-7.22 (m, 5H), 4.24 (t, J=7.4 Hz, 1H), 3.51 (dd, J=13.9, 3.2 Hz, 1H), 3.05 (dd, J=13.5, 7.3 Hz, 1H), 2.92 (dd, J=13.6, 7.9 Hz, 1H), 2.79 (dd, J=13.8, 8.5 Hz, 1H), 2.18-2.14 (m, 1H), 2.03-1.95 (m, 1H), 1.86-1.77 (m, 2H), 1.59-1.46 (m, 2H), 1.44 (s, 9H), 1.30 (dd, J=15.6, 7.5 Hz, 2H), 1.07 (t, J=12.4 Hz, 1H), 0.86-0.75 (m, 3H).

Step B. (1R,2S,5R)-1-Amino-2-(((S)-2-amino-3-phenylpropanamido)methyl)-5-(2-boronoethyl)cyclohexane-1-carboxylic acid dihydrochloride (1R,2S,5R)-1-Amino-5-(2-boronoethyl)-2-(((S)-2-((tert-butoxycarbonyl)amino)-3-phenylpropanamido)methyl)cyclohexane-1-carboxylic acid (35 mg, 0.07 mmol) was treated with 2 M HCl$_{aq}$ (1 mL) and the resulting mixture was stirred at room temperature for 1.5 h. Then the reaction mixture was concentrated under reduced pressure at 35° C. and the residue was lyophilized to give the corresponding product (30 mg, 91% yield, white solid). ESI+MS: m/z=392.05 (M+1)+; ESI-MS: m/z=390.00 (M−1)−. $^1$H NMR (700 MHz, deuterium oxide) δ 7.50-7.42 (m, 3H), 7.32 (d, J=7.2 Hz, 2H), 4.18 (dd, J=10.2, 5.8 Hz, 1H), 3.66

(dd, J=13.8, 2.6 Hz, 1H), 3.32 (dd, J=13.4, 5.7 Hz, 1H), 3.11 (dd, J=13.4, 10.2 Hz, 1H), 2.66 (dd, J=13.7, 10.2 Hz, 1H), 2.23-2.19 (m, 1H), 1.79-1.69 (m, 2H), 1.51-1.32 (m, 4H), 1.24 (t, J=12.7 Hz, 1H), 1.03-0.98 (m, 1H), 0.84-0.73 (m, 3H).

Example 4. (1R,2S,5R)-1-Amino-2-((2-aminoacetamido)methyl)-5-(2-boronoethyl)cyclohexane-1-carboxylic acid dihydrochloride x 2 HCl

Step A. (1R,2S,5R)-1-Amino-5-(2-boronoethyl)-2-((2-((tert-butoxycarbonyl)amino)acetamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (41 mg, 0.13 mmol), Boc-Gly-OSu (39 mg, 0.14 mmol), TEA (90 μL, 0.65 mmol) and DMF (2.3 mL). The residue was purified by preparative HPLC (1-60% of acetonitrile in water) to give the corresponding product (21 mg, 41% yield, white solid). ESI+MS: m/z=401.95 (M+1)+; ESI-MS: m/z=400.05 (M−1)−. $^1$H NMR (700 MHz, methanol-d$_4$) δ 3.70 (s, 2H), 3.60-3.48 (m, 1H), 2.94 (dd, J=13.7, 7.9 Hz, 1H), 2.24-2.16 (m, 1H), 2.12-1.79 (m, 4H), 1.75-1.66 (m, 1H), 1.50 (s, 9H), 1.34-1.26 (m, 2H), 1.10 (t, J=12.5 Hz, 1H), 0.92-0.73 (m, 3H).

Step B. (1R,2S,5R)-1-Amino-2-((2-aminoacetamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-((2-((tert-butoxycarbonyl)amino)acetamido)methyl)cyclohexane-1-carboxylic acid (17 mg, 0.04 mmol) and 2 M HCl$_{aq}$ (1 mL). The desired product was obtained as a white solid (14.7 mg, 93% yield). ESI+MS: m/z=301.90 (M+1)+; ESI-MS: m/z=299.85 (M−1)−. $^1$H NMR (700 MHz, deuterium oxide) δ 3.84 (s, 2H), 3.58 (dd, J=14.0, 2.8 Hz, 1H), 3.18 (dd, J=14.0, 9.2 Hz, 1H), 2.33-2.26 (m, 1H), 1.98-1.86 (m, 3H), 1.85-1.70 (m, 2H), 1.43-1.28 (m, 3H), 1.00-0.92 (m, 1H), 0.85-0.78 (m, 2H).

Example 5. (1R,2S,5R)-1-Amino-5-(2-boronoethyl)-2-(((S)-pyrrolidine-2-carboxamido)methyl)cyclo-hexane-1-carboxylic acid dihydrochloride Step A. (1R,2S,5R)-1-Amino-5-(2-boronoethyl)-2-(((S)-1-(tert-butoxycarbonyl)pyrrolidine-2-carbox-amido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (38 mg, 0.12 mmol), Boc-L-Pro-OSu (41 mg, 0.13 mmol), TEA (84 μL, 0.60 mmol) and DMF (2 mL). The residue was purified by preparative HPLC (1-60% of acetonitrile in water) to give the corresponding product (32 mg, 60% yield, white solid). ESI+MS: m/z=442.00 (M+1)⁺; ESI-MS: m/z=440.00 (M−1)⁻. ¹H NMR (700 MHz, metha-nol-d₄) δ 4.22-4.13 (m, 1H), 3.75-3.51 (m, 2H), 3.48-3.43 (m, 1H), 2.97-2.77 (m, 1H), 2.30-2.16 (m, 2H), 2.06-1.80 (m, 7H), 1.76-1.62 (m, 1H), 1.49 (d, J=36.1 Hz, 9H), 1.34-1.26 (m, 2H), 1.11 (t, J=12.5 Hz, 1H), 0.92-0.77 (m, 3H).

Step B. (1R,2S,5R)-1-Amino-5-(2-boronoethyl)-2-(((S)-pyrrolidine-2-carboxamido)methyl)cyclo-hexane-1-carboxylic acid dihydrochloride The title compound was obtained in the same manner as in Example 3, step B, using (1R,2S,5R)-1-amino-5-(2-bo-ronoethyl)-2-(((S)-1-(tert-butoxycarbonyl)pyrrolidine-2-carboxamido)methyl)cyclohexane-1-carboxylic acid (29 mg, 0.07 mmol) and 2 M HCl$_{aq}$ (1 mL). The desired product was obtained as a white solid (25.6 mg, 94% yield). ESI+ MS: m/z=341.90 (M+1)⁺; ESI-MS: m/z=340.00 (M−1)⁻. ¹H NMR (700 MHz, deuterium oxide) δ 4.40 (dd, J=8.5, 6.7 Hz, 1H), 3.63 (dd, J=13.9, 2.7 Hz, 1H), 3.51-3.41 (m, 2H), 3.13 (dd, J=13.9, 9.2 Hz, 1H), 2.52-2.46 (m, 1H), 2.31-2.27 (m, 1H), 2.15-2.02 (m, 3H), 1.98-1.87 (m, 3H), 1.85-1.72 (m, 2H), 1.41-1.27 (m, 3H), 0.99-0.92 (m, 1H), 0.82 (dd, J=9.4, 6.8 Hz, 2H).

Example 6. (1R,2S,5R)-1-Amino-2-(((S)-2-amino-4-methylpentanamido)methyl)-5-(2-boronoethyl)cyclohexane-1-carboxylic acid dihydrochloride Step A. (1R,2S,5R)-1-Amino-5-(2-boronoethyl)-2-(((S)-2-((tert-butoxycarbonyl)amino)-4-methylpen-tanamido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (38 mg, 0.12 mmol), Boc-L-Leu-OSu (43 mg, 0.13 mmol), TEA (84 μL, 0.60 mmol) and DMF (2.1 mL). The residue was purified by preparative HPLC (1-60% of acetonitrile in water) to give the corresponding product (36 mg, 66% yield, white solid). ESI+MS: m/z=458.05 (M+1)⁺; ESI-MS: m/z=456.05 (M−1)⁻. ¹H NMR (700 MHz, methanol-d₄) δ 4.02 (t, J=7.5 Hz, 1H), 3.58 (dd, J=14.2, 3.7 Hz, 1H), 2.89 (dd, J=14.1, 8.0 Hz, 1H), 2.20-2.15 (m, 1H), 2.06-1.93 (m, 2H), 1.91-1.85 (m, 1H), 1.83-1.78 (m, 1H), 1.76-1.65 (m, 2H), 1.54 (t, J=7.3 Hz, 2H), 1.49 (s, 9H), 1.35-1.26 (m, 2H), 1.11 (t, J=12.4 Hz, 1H), 0.98 (dd, J=20.6, 6.6 Hz, 6H), 0.89-0.73 (m, 3H).

Step B. (1R,2S,5R)-1-Amino-2-(((S)-2-amino-4-methylpentanamido)methyl)-5-(2-boronoethyl)cy-clohexane-1-carboxylic acid dihydrochloride The title compound was obtained in the same manner as in Example 3, step B, using (1R,2S,5R)-1-amino-5-(2-bo-ronoethyl)-2-(((S)-2-((tert-butoxycarbonyl)amino)-4-meth-ylpentanamido)methyl)cyclohexane-1-carboxylic acid (33 mg, 0.07 mmol) and 2 M HCl$_{aq}$ (1 mL). The desired product was obtained as a white solid (30.6 mg, 99% yield). ESI+ MS: m/z=358.00 (M+1)⁺; ESI-MS: m/z=356.00 (M−1)⁻. ¹H NMR (700 MHz, deuterium oxide) δ 4.01 (t, J=7.4 Hz, 1H), 3.70 (dd, J=13.8, 2.7 Hz, 1H), 3.00 (dd, J=13.8, 9.6 Hz, 1H), 2.30-2.24 (m, 1H), 1.97-1.91 (m, 1H), 1.91-1.81 (m, 3H), 1.80-1.73 (m, 3H), 1.71-1.64 (m, 1H), 1.37 (dd, J=15.6, 7.4 Hz, 2H), 1.29 (t, J=12.7 Hz, 1H), 1.01 (dd, J=9.3, 6.6 Hz, 6H), 0.93 (ddd, J=25.4, 13.0, 3.7 Hz, 1H), 0.86-0.78 (m, 2H).

Example 7. (1R,2S,5R)-1-Amino-2-(((S)-2-amino-3-hydroxypropanamido)methyl)-5-(2-boronoethyl)cyclohexane-1-carboxylic acid dihydrochloride x 2 HCl

Step A. (1R,2S,5R)-1-Amino-2-(((S)-3-(benzyloxy)-2-((tert-butoxycarbonyl)amino)propanamido)methyl)-5-(2-boronoethyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (41 mg, 0.13 mmol), Boc-L-Ser(OBn)-OSu (56 mg, 0.14 mmol), TEA (90 μL, 0.65 mmol) and DMF (2.3 mL). The residue was purified by preparative HPLC (1-60% of acetonitrile in water) to give the corresponding product (40 mg, 59% yield, white solid). ESI+MS: m/z=522.20 (M+1)$^+$; ESI-MS: m/z=520.30 (M-1)$^-$. $^1$H NMR (700 MHz, methanol-d$_4$) δ 7.38-7.30 (m, 5H), 4.57 (s, 2H), 4.26-4.22 (m, 1H), 3.78-3.74 (m, 1H), 3.70 (dd, J=9.5, 5.2 Hz, 1H), 3.65-3.60 (m, 1H), 2.91-2.83 (m, 1H), 2.19-2.14 (m, 1H), 2.06-1.99 (m, 1H), 1.97-1.90 (m, 1H), 1.85-1.78 (m, 2H), 1.71-1.65 (m, 1H), 1.49 (s, 9H), 1.29 (dd, J=15.1, 8.1 Hz, 2H), 1.08 (t, J=12.5 Hz, 1H), 0.84-0.76 (m, 3H).

Step B. (1R,2S,5R)-1-Amino-2-(((S)-2-amino-3-(benzyloxy)propanamido)methyl)-5-(2-boronoethyl)cyclohexane-1-carboxylic acid dihydrochloride x 2 HCl The title compound was obtained in the same manner as in Example 3, step B, using (1R,2S,5R)-1-amino-2-(((S)-3-(benzyloxy)-2-((tert-butoxycarbonyl)amino)propanamido)methyl)-5-(2-boronoethyl)cyclohexane-1-carboxylic acid (36 mg, 0.07 mmol) and 2 M HCl$_{aq}$ (1 mL). The desired product was obtained as a white solid (34 mg, 99% yield). ESI+MS: m/z=422.00 (M+1)$^+$; ESI-MS: m/z=419.19 (M-1)$^-$. $^1$H NMR (700 MHz, deuterium oxide) δ 7.54-7.38

(m, 5H), 4.66 (dd, J=72.2, 11.8 Hz, 2H), 4.28 (t, J=4.0 Hz, 1H), 3.99-3.92 (m, 2H), 3.70 (dd, J=13.9, 3.0 Hz, 1H), 2.99 (dd, J=13.9, 9.7 Hz, 1H), 2.30-2.24 (m, 1H), 1.89-1.82 (m, 2H), 1.81-1.73 (m, 2H), 1.70-1.59 (m, 1H), 1.37-1.31 (m, 2H), 1.28 (t, J=12.8 Hz, 1H), 0.83-0.70 (m, 3H).

Step C. (1R,2S,5R)-1-Amino-2-(((S)-2-amino-3-hydroxypropanamido)methyl)-5-(2-boronoethyl)cyclohexane-1-carboxylic acid dihydrochloride (1R,2S,5R)-1-Amino-2-(((S)-2-amino-3-(benzyloxy)propanamido)methyl)-5-(2-boronoethyl)cyclohexane-1-carboxylic acid dihydrochloride (32 mg, 0.065 mmol) was dissolved in 3 mL of MeOH and flushed with argon. Next, 20 mg of Pd/C (wet, 10%) was added and the resulting mixture was stirred under hydrogen atmosphere for 1 h. The reaction mixture was filtered through a pad of Celite and the filtrate was concentrated. The residue was dissolved in water and lyophilized to give the corresponding product (22 mg, 84% yield, white solid). ESI+MS: m/z=331.90 (M+1)$^+$; ESI-MS: m/z=329.95 (M-1)$^-$. $^1$H NMR (700 MHz, deuterium oxide) δ 4.15 (dt, J=10.2, 5.1 Hz, 1H), 4.08-3.93 (m, 2H), 3.65 (dd, J=13.9, 2.9 Hz, 1H), 3.12 (dd, J=13.9, 9.1 Hz, 1H), 2.31-2.24 (m, 1H), 2.00-1.69 (m, 5H), 1.41-1.34 (m, 2H), 1.32 (t, J=12.7 Hz, 1H), 0.95 (qd, J=12.9, 3.4 Hz, 1H), 0.82 (dd, J=9.3, 6.9 Hz, 2H).

Example 8. (1R,2S,5R)-1-Amino-2-(((S)-2-amino-3-(1H-imidazol-4-yl)propanamido)methyl)-5-(2-boronoethyl)cyclohexane-1-carboxylic acid trihydrochloride x 3 HCl

Step A. (1R,2S,5R)-1-Amino-5-(2-boronoethyl)-2-(((S)-2-((tert-butoxycarbonyl)amino)-3-(1H-imidazol-4-yl)propanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-His-(1-Boc)-OSu (60 mg, 0.13 mmol), TEA (84 μL, 0.60 mmol) and DMF (2 mL). The residue was purified by preparative HPLC (1-50% of acetonitrile in water) to give the corresponding product (16 mg, 28% yield, white solid). ESI+MS: m/z=482.05 (M+1)$^+$; ESI-MS: m/z=480.10 (M-1)$^-$. $^1$H NMR (700 MHz, methanol-d$_4$) δ 7.82 (s, 1H), 6.98 (s, 1H), 4.25 (t, J=6.9 Hz, 1H), 3.60-3.47 (m, 1H), 3.40-3.35 (m, 1H), 3.08 (dd, J=14.3, 6.5 Hz, 1H), 2.98-2.80 (m, 2H), 2.23-2.13 (m, 1H), 2.07-1.98 (m, 1H), 1.98-1.84 (m, 2H), 1.71-1.57 (m, 2H), 1.46 (s, 9H), 1.38-1.24 (m, 2H), 1.09 (t, J=12.4 Hz, 1H), 0.88-0.76 (m, 2H).

Step B. (1R,2S,5R)-1-Amino-2-(((S)-2-amino-3-(1H-imidazol-4-yl)propanamido)methyl)-5-(2-boronoethyl)cyclohexane-1-carboxylic acid trihydrochloride The title compound was obtained in the same manner as in Example 3, step B, using (1R,2S,5R)-1-amino-5-(2-boronoethyl)-2-(((S)-2-((tert-butoxycarbonyl)amino)-3-(1H-imidazol-4-yl)propanamido)methyl)cyclohexane-1-carboxylic acid (15 mg, 0.03 mmol) and 2 M HCl$_{aq}$ (1 mL). The desired product was obtained as a white solid (15 mg, 99% yield). ESI+MS: m/z=382.00 (M+1)$^+$; ESI-MS: m/z=380.05 (M−1)$^-$. $^1$H NMR (700 MHz, deuterium oxide) δ 8.80 (d, J=1.3 Hz, 1H), 7.50 (s, 1H), 4.27 (dd, J=8.5, 6.7 Hz, 1H), 3.64 (dd, J=13.8, 2.8 Hz, 1H), 3.45-3.37 (m, 2H), 2.95 (dd, J=13.9, 9.4 Hz, 1H), 2.27-2.21 (m, 1H), 1.91-1.86 (m, 1H), 1.85-1.77 (m, 1H), 1.70-1.59 (m, 2H), 1.40-1.30 (m, 3H), 1.26 (t, J=12.7 Hz, 1H), 0.90-0.76 (m, 3H).

Example 9. (1R,2S,5R)-1-Amino-5-(2-boronoethyl)-2-(((S)-2,6-diaminohexanamido)methyl)cyclohexane-1-carboxylic acid trihydrochloride x 3 HCl

Step A. (1R,2S,5R)-1-Amino-2-(((S)-2,6-bis((tert-butoxycarbonyl)amino)hexanamido)methyl)-5-(2-boronoethyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-Lys(Boc)-OSu (58 mg, 0.13 mmol), TEA (84 μL, 0.60 mmol) and DMF (2 mL). The residue was purified by preparative HPLC (1-55% of acetonitrile in water) to give the corresponding product (30 mg, 44% yield, white solid). ESI+MS: m/z=573.15 (M+1)$^+$; ESI-MS: m/z=571.20 (M−1)$^-$. $^1$H NMR (700 MHz, methanol-d$_4$) δ 3.93 (dd, J=8.5, 5.4 Hz, 1H), 3.58 (dd, J=13.9, 3.3 Hz, 1H), 3.07 (t, J=6.9 Hz, 2H), 2.89 (dd, J=13.8, 8.3 Hz, 1H), 2.22-2.14 (m, 1H), 2.07-1.79 (m, 4H), 1.78-1.60 (m, 3H), 1.59-1.41 (m, 21H), 1.41-1.34 (m, 1H), 1.34-1.25 (m, 2H), 1.11 (t, J=12.5 Hz, 1H), 0.91-0.74 (m, 3H).

Step B. (1R,2S,5R)-1-Amino-5-(2-boronoethyl)-2-(((S)-2,6-diaminohexanamido)methyl)cyclohexane-1-carboxylic acid trihydrochloride The title compound was obtained in the same manner as in Example 3, step B, using (1R,2S,5R)-1-amino-2-(((S)-2,6-bis((tert-butoxycarbonyl)amino)hexanamido)methyl)-5-(2-boronoethyl)cyclohexane-1-carboxylic acid (27 mg, 0.05 mmol) and 2 M HCl$_{aq}$ (2 mL). The desired product was obtained as a white solid (22.5 mg, 99% yield). ESI+MS: m/z=373.05 (M+1)$^+$; ESI-MS: m/z=371.05 (M−1)$^-$. $^1$H NMR (700 MHz, deuterium oxide) δ 4.02 (t, J=6.7 Hz, 1H), 3.65 (dd, J=13.9, 2.7 Hz, 1H), 3.10 (dd, J=13.9, 9.2 Hz, 1H), 3.08-2.99 (m, 2H), 2.29-2.22 (m, 1H), 2.04-1.89 (m, 3H), 1.90-1.67 (m, 6H), 1.48 (dt, J=16.0, 8.2 Hz, 2H), 1.37 (dd, J=15.7, 7.3 Hz, 2H), 1.29 (t, J=12.7 Hz, 1H), 0.94 (ddd, J=16.2, 13.0, 3.6 Hz, 1H), 0.86-0.80 (m, 2H).

Example 10. (1R,2S,5R)-1-Amino-2-(((2S,3S)-2-amino-3-methylpentanamido)methyl)-5-(2-boronoethyl)cyclohexane-1-carboxylic acid dihydrochloride x 2 HCl

Step A. (1R,2S,5R)-1-Amino-5-(2-boronoethyl)-2-(((2S,3S)-2-((tert-butoxycarbonyl)amino)-3-methylpentanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-Ile-OSu (43 mg, 0.13 mmol), TEA (84 μL, 0.60 mmol) and DMF (2 mL). The residue was purified by preparative HPLC (1-60% of acetonitrile in water) to give the corresponding product (23 mg, 42% yield, white solid). ESI+MS: m/z=458.10 (M+1)$^+$; ESI-MS: m/z=456.15 (M−1)$^-$. $^1$H NMR (700 MHz, methanol-d$_4$) δ 3.86 (d, J=7.0 Hz, 1H), 3.61 (dd, J=13.7, 2.9 Hz, 1H), 2.87 (dd, J=13.8, 8.7 Hz, 1H), 2.21-2.17 (m, 1H), 2.05-1.91 (m, 2H), 1.91-1.76 (m, 3H), 1.73-1.66 (m, 1H), 1.59-1.51 (m, 1H), 1.49 (s, 9H), 1.31 (dd, J=15.3, 7.7 Hz, 2H), 1.25-1.19 (m, 1H), 1.11 (t, J=12.5 Hz, 1H), 0.99-0.93 (m, 6H), 0.87-0.77 (m, 3H).

Step B. (1R,2S,5R)-1-Amino-2-(((2S,3S)-2-amino-3-methylpentanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((2S,3S)-2-((tert-butoxycarbonyl)amino)-3-methylpentanamido)methyl)cyclohexane-1-carboxylic acid (19 mg, 0.04 mmol) and 2 M $HCl_{aq}$ (3 mL). The desired product was obtained as a white solid (17 mg, 99% yield). ESI+MS: m/z=358.05 (M+1)$^+$; ESI-MS: m/z=356.10 (M–1)$^-$. $^1$H NMR (700 MHz, deuterium oxide) δ 3.89 (d, J=5.5 Hz, 1H), 3.72 (dd, J=13.8, 2.5 Hz, 1H), 3.01 (dd, J=13.8, 10.0 Hz, 1H), 2.33-2.27 (m, 1H), 2.04-1.97 (m, 1H), 1.96-1.71 (m, 5H), 1.56-1.48 (m, 1H), 1.39-1.24 (m, 4H), 1.04 (d, J=6.9 Hz, 3H), 0.99-0.91 (m, 4H), 0.82 (dd, J=9.5, 7.0 Hz, 2H).

Example 11. (1R,2S,5R)-1-Amino-2-(((S)-2-amino-2-cyclopentylacetamido)methyl)-5-(2-boronoethyl)cyclohexane-1-carboxylic acid dihydrochloride

Step A. 2,5-Dioxopyrrolidin-1-yl (S)-2-((tert-butoxycarbonyl)amino)-2-cyclopentylacetate To a solution of (S)-2-((tert-butoxycarbonyl)amino)-2-cyclopentylacetic acid (1 g, 4.11 mmol) in dry THF (20 mL), TEA (1.43 mL, 10.27 mmol) and N,N'-disuccinimidyl carbonate (90% purity, 1.40 g, 4.93 mmol) were added under argon and the resulting mixture was stirred at room temperature overnight. The reaction was diluted with AcOEt (40 mL) and quenched with saturated aqueous solution of NaHCO$_3$ (30 mL). Layers were separated and the organic phase was washed with 0.5 M NaOH (1x 30 mL), brine (1x 30 mL), dried over Na$_2$SO$_4$, filtered and concentrated to give the corresponding product (1.12 g, 80% yield, white solid). ESI+MS: m/z=362.95 (M+23)$^+$, 241.00 (M–100+1)$^+$. $^1$H NMR (700 MHz, chloroform-d) δ 5.01 (d, J=8.4 Hz, 1H), 4.56 (t, J=7.9 Hz, 1H), 2.82 (s, 4H), 2.38-2.29 (m, 1H), 1.96-1.77 (m, 2H), 1.72-1.64 (m, 2H), 1.61-1.53 (m, 2H), 1.51-1.47 (m, 1H), 1.44 (s, 9H), 1.40-1.33 (m, 1H).

Step B. (1R,2S,5R)-1-Amino-5-(2-boronoethyl)-2-(((S)-2-((tert-butoxycarbonyl)amino)-2-cyclopentylacetamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), 2,5-dioxopyrrolidin-1-yl (S)-2-((tert-butoxycarbonyl)amino)-2-cyclopentylacetate (45 mg, 0.13 mmol), TEA (84 μL, 0.60 mmol) and DMF (2 mL). The residue was purified by preparative HPLC (1-55% of acetonitrile in water) to give the corresponding product (29 mg, 51% yield, white solid). ESI+MS: m/z=470.10 (M+1)$^+$; ESI-MS: m/z=468.15 (M–1)$^-$. $^1$H NMR (700 MHz, methanol-d$_4$) δ 3.78 (d, J=8.9 Hz, 1H), 3.58 (dd, J=13.8, 3.4 Hz, 1H), 2.90 (dd, J=13.8, 8.5 Hz, 1H), 2.22-2.12 (m, 2H), 2.06-2.01 (m, 1H), 2.00-1.93 (m, 1H), 1.93-1.80 (m, 3H), 1.77-1.64 (m, 4H), 1.64-1.56 (m, 2H), 1.49 (s, 9H), 1.42-1.29 (m, 4H), 1.11 (t, J=12.5 Hz, 1H), 0.89-0.75 (m, 3H).

Step C. (1R,2S,5R)-1-Amino-2-(((S)-2-amino-2-cyclopentylacetamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-2-cyclopentylacetamido)methyl)cyclohexane-1-carboxylic acid (16 mg, 0.034 mmol) and 2 M $HCl_{aq}$ (3 mL). The desired product was obtained as a white solid (15 mg, 99% yield). ESI+MS: m/z=370.00 (M+1)$^+$; ESI-MS: m/z=368.05 (M–1)$^-$. $^1$H NMR (700 MHz, deuterium oxide) δ 3.80 (d, J=8.6 Hz, 1H), 3.73 (dd, J=13.7, 2.5 Hz, 1H), 2.99 (dd, J=13.8, 10.1 Hz, 1H), 2.35-2.24 (m, 2H), 1.99-1.89 (m, 3H), 1.88-1.69 (m, 6H), 1.68-1.60 (m, 2H), 1.43-1.29 (m, 5H), 0.98-0.89 (m, 1H), 0.86-0.76 (m, 2H).

Example 12. (1R,2S,5R)-1-Amino-2-(((S)-2-amino-3,3-dimethylbutanamido)methyl)-5-(2-boronoethyl)cyclohexane-1-carboxylic acid dihydrochloride

Step A. (1R,2S,5R)-1-Amino-5-(2-boronoethyl)-2-(((S)-2-((tert-butoxycarbonyl)amino)-3,3-dimethylbutanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-tert-Leu-OSu (43 mg, 0.13 mmol), TEA (84 μL, 0.60 mmol) and DMF (2 mL). The residue was purified by preparative HPLC (1-55% of acetonitrile in water) to give the corresponding product (13 mg, 24% yield, white solid). ESI+MS: m/z=458.10 (M+1)$^+$; ESI-MS: m/z=456.05 (M−1)$^−$. $^1$H NMR (700 MHz, methanol-d$_4$) δ 3.83 (s, 1H), 3.63 (dd, J=13.2, 2.5 Hz, 1H), 2.85 (dd, J=14.0, 9.2 Hz, 1H), 2.22 (dd, J=13.0, 2.3 Hz, 1H), 2.00-1.87 (m, 4H), 1.75-1.67 (m, 1H), 1.49 (s, 9H), 1.36-1.29 (m, 2H), 1.16 (t, J=12.6 Hz, 1H), 1.03 (s, 9H), 0.91-0.77 (m, 3H).

Step B. (1R,2S,5R)-1-Amino-2-(((S)-2-amino-3,3-dimethylbutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-3,3-dimethylbutanamido)methyl)cyclohexane-1-carboxylic acid (13 mg, 0.03 mmol) and 2 M HCl$_{aq}$ (2 mL). The desired product was obtained as a white solid (12.2 mg, 95% yield). ESI+MS: m/z=358.05 (M+1)$^+$; ESI-MS: m/z=356.00 (M−1)$^−$. $^1$H NMR (700 MHz, deuterium oxide) δ 3.74-3.69 (m, 2H), 3.01 (dd, J=13.8, 9.7 Hz, 1H), 2.30-2.26 (m, 1H), 1.98-1.90 (m, 2H), 1.87-1.75 (m, 3H), 1.41-1.34 (m, 2H), 1.31 (t, J=12.7 Hz, 1H), 1.12 (s, 9H), 0.98-0.91 (m, 1H), 0.85-0.80 (m, 2H).

Example 13. (1R,2S,5R)-1-Amino-2-(((S)-2-amino-5-guanidinopentanamido)methyl)-5-(2-boronoethyl)cyclohexane-1-carboxylic acid trihydrochloride x 3 HCl

Step A. 2,5-Dioxopyrrolidin-1-yl (Z)—N$^\omega$,N$^{\omega'}$,N-tris(tert-butoxycarbonyl)-L-argininate (Boc-L-Arg(Boc)$_2$-OSu)

The title compound was obtained in the same manner as in Example 11, step A, using Boc-L-Arg(Boc)$_2$-OH (5 g, 10.54 mol), TEA (3.66 mL, 26.25 mmol), N,N'-disuccinimidyl carbonate (90% of purity, 3.28 g, 11.59 mmol) and dry THF (100 mL). The desired product was obtained as a white solid (4.94 g, 82% yield). ESI+MS: m/z=572.25 (M+1)$^+$, 516.10 (M−56+1)$^+$, 472.15 (M−100+1)$^+$.

Step B. (1R,2S,5R)-1-Amino-2-(((S)-2-amino-5-guanidinopentanamido)methyl)-5-(2-boronoethyl)cyclohexane-1-carboxylic acid trihydrochloride To a stirred solution of (1R,2S,5R)-1-amino-2-(aminomethyl)-5-(2-boronoethyl)cyclohexane-1-carboxylic acid dihydrochloride (38 mg, 0.12 mmol) in DMF (2 mL), Boc-L-Arg(Boc)$_2$-OSu (75 mg, 0.13 mmol) and TEA (84 μL, 0.60 mmol) were added and the resulting mixture was stirred at room temperature overnight. DMF was evaporated under reduced pressure and the residue purified by preparative HPLC (1-60% of acetonitrile in water) to give the coupling product as a mixture of product with two and three Boc groups. The mixture was treated with 2 M HCl$_{aq}$ (3 mL) and stirred at room temperature for 4 h. Then the reaction mixture was concentrated under reduced pressure at 35° C. and the residue was purified by preparative HPLC (0.1-5% of acetonitrile in water) to give the corresponding product (18.7 mg, 31% yield, white solid). ESI+MS: m/z=401.00 (M+1)$^+$; ESI-MS: m/z=399.05 (M−1)$^−$. $^1$H NMR (700 MHz, deuterium oxide) δ 4.04 (t, J=6.6 Hz, 1H), 3.69 (dd, J=13.9, 2.7 Hz, 1H), 3.32-3.24 (m, 2H), 3.06 (dd, J=13.9, 9.4 Hz, 1H), 2.31-2.24 (m, 1H), 2.00-1.92 (m, 3H), 1.89-1.72 (m, 4H), 1.71-1.64 (m, 2H), 1.37 (dd, J=15.7, 7.3 Hz, 2H), 1.30 (t, J=12.7 Hz, 1H), 0.92 (qd, J=13.1, 3.7 Hz, 1H), 0.86-0.78 (m, 2H).

Example 14. (1R,2S,5R)-1-Amino-2-(((S)-2-amino-3-(4-hydroxyphenyl)propanamido)methyl)-5-(2-boronoethyl)cyclohexane-1-carboxylic acid dihydrochloride x 2 HCl

Step A. (1R,2S,5R)-1-Amino-5-(2-boronoethyl)-2-(((S)-2-((tert-butoxycarbonyl)amino)-3-(4-hydroxyphenyl)propanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-Tyr-OSu (50 mg, 0.13 mmol), TEA (84 μL, 0.60 mmol) and DMF (2 mL). The residue was purified by preparative HPLC (1-55% of acetonitrile in water) to give the corresponding product (25 mg, 41% yield, white solid). ESI+MS: m/z=508.20 (M+1)$^+$; ESI-MS: m/z=506.15 (M−1)$^−$. $^1$H NMR (700 MHz, methanol-d$_4$) δ 7.10-7.02 (m, 2H), 6.75 (d, J=8.3 Hz, 2H), 4.16 (t, J=7.4 Hz, 1H), 3.55-3.47 (m, 1H), 2.92 (dd, J=13.9, 8.3 Hz, 1H), 2.84 (dd, J=13.6, 7.4 Hz, 1H), 2.75 (dd, J=13.5, 8.8 Hz, 1H), 2.18-2.14 (m, 1H), 2.00-1.91 (m, 1H), 1.85-1.73 (m, 2H), 1.57-1.47 (m, 2H), 1.45 (s, 9H), 1.34-1.27 (m, 2H), 1.08 (t, J=12.5 Hz, 1H), 0.88-0.75 (m, 3H).

Step B. (1R,2S,5R)-1-Amino-2-(((S)-2-amino-3-(4-hydroxyphenyl)propanamido)methyl)-5-(2-borono-ethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-3-(4-hydroxy-phenyl)propanamido)methyl)cyclohexane-1-carboxylic acid (23 mg, 0.045 mmol) and 2 M $HCl_{aq}$ (2 mL). The desired product was obtained as a white solid (20.7 mg, 96% yield). ESI+MS: m/z=408.00 (M+1)$^+$; ESI-MS: m/z=406.00 (M−1)$^-$. $^1$H NMR (700 MHz, deuterium oxide) δ 7.21-7.17 (m, 2H), 6.97-6.89 (m, 2H), 4.11 (dd, J=10.8, 5.6 Hz, 1H), 3.70 (dd, J=13.7, 2.0 Hz, 1H), 3.26 (dd, J=13.4, 5.6 Hz, 1H), 2.99 (dd, J=13.4, 10.8 Hz, 1H), 2.63-2.58 (m, 1H), 2.23 (d, J=11.6 Hz, 1H), 1.80-1.75 (m, 1H), 1.74-1.67 (m, 1H), 1.42-1.32 (m, 4H), 1.24 (t, J=12.7 Hz, 1H), 0.99-0.93 (m, 1H), 0.85-0.73 (m, 3H).

Example 15. (1R,2S,5R)-1-Amino-5-(2-borono-ethyl)-2-(((S)-2,4-diamino-4-oxobutanamido)methyl)cyclohexane-1-carboxylic acid dihydrochloride x 2 HCl

Step A. (1R,2S,5R)-1-Amino-2-(((S)-4-amino-2-((tert-butoxycarbonyl)amino)-4-oxobutanamido)methyl)-5-(2-boronoethyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-L-Asn-OSu (43 mg, 0.13 mmol), TEA (84 μL, 0.60 mmol) and DMF (2 mL). The residue was purified by preparative HPLC (1-40% of acetonitrile in water) to give the corresponding product (12 mg, 23% yield, white solid). ESI+MS: m/z=459.05 (M+1)$^+$; ESI-MS: m/z=457.00 (M−1)$^-$. $^1$H NMR (700 MHz, methanol-d$_4$) δ 4.59 (s, 1H), 4.37 (t, J=6.5 Hz, 1H), 3.55-3.49 (m, 1H), 2.99-2.93 (m, 1H), 2.72-2.64 (m, 1H), 2.19-2.15 (m, 1H), 2.07-1.93 (m, 2H), 1.91-1.79 (m, 2H), 1.73-1.66 (m, 1H), 1.49 (s, 9H), 1.36-1.27 (m, 2H), 1.09 (t, J=12.4 Hz, 1H), 0.92-0.76 (m, 3H).

Step B. (1R,2S,5R)-1-Amino-5-(2-boronoethyl)-2-(((S)-2,4-diamino-4-oxobutanamido)methyl)cyclohexane-1-carboxylic acid dihydrochloride The title compound was obtained in the same manner as in Example 3, step B, using (1R,2S,5R)-1-amino-2-(((S)-4- amino-2-((tert-butoxycarbonyl)amino)-4-oxobutanamido)methyl)-5-(2-boronoethyl)cyclohexane-1-carboxylic acid (11 mg, 0.045 mmol) and 2 M $HCl_{aq}$ (2 mL). The desired product was obtained as a white solid (10.4 mg, 99% yield). ESI+MS: m/z=359.00 (M+1)$^+$; ESI-MS: m/z=357.00 (M−1)$^-$. $^1$H NMR (700 MHz, deuterium oxide) δ 4.33 (t, J=6.1 Hz, 1H), 3.70 (dd, J=13.8, 2.8 Hz, 1H), 3.05-2.94 (m, 3H), 2.30 (ddd, J=13.0, 3.4, 1.7 Hz, 1H), 1.96-1.83 (m, 3H), 1.82-1.67 (m, 2H), 1.40-1.29 (m, 3H), 0.93 (qd, J=13.1, 3.5 Hz, 1H), 0.82 (dd, J=9.4, 7.0 Hz, 2H).

Example 16. (1R,2S,5R)-1-Amino-2-(((S)-2-amino-3-hydroxy-3-methylbutanamido)methyl)-5-(2-boronoethyl)cyclohexane-1-carboxylic acid dihydrochloride x 2 HCl

Step A. (1R,2S,5R)-1-Amino-5-(2-boronoethyl)-2-(((S)-2-((tert-butoxycarbonyl)amino)-3-hydroxy-3-methylbutanamido)methyl)cyclohexane-1-carboxylic acid To a solution of (S)-2-((tert-butoxycarbonyl)amino)-3-hydroxy-3-methylbutanoic acid (28 mg, 0.12 mmol) in DMF (1 mL) cooled to 0° C., DIPEA (104 μL, 0.60 mmol) and HATU (46 mg, 0.12 mmol) were added and the reaction mixture was stirred for 15 min at this temperature. Then, a solution of (1R,2S,5R)-1-amino-2-(aminomethyl)-5-(2-boronoethyl)cyclohexane-1-carboxylic acid dihydrochloride (38 mg, 0.12 mmol) in DMF (0.5 mL) was slowly added and the reaction mixture was stirred overnight at room temperature. DMF was evaporated and the residue was purified by preparative HPLC (1-50% of acetonitrile in water) to give the corresponding product (10 mg, 18% yield, white solid). ESI+MS: m/z=460.05 (M+1)$^+$; ESI-MS: m/z=458.00 (M−1)$^-$. $^1$H NMR (700 MHz, methanol-d$_4$) δ 3.95 (s, 1H), 3.63-3.54 (m, 1H), 2.92 (dd, J=13.7, 8.3 Hz, 1H), 2.21-2.16 (m, 1H), 2.08-1.82 (m, 4H), 1.71 (ddd, J=12.0, 8.2, 4.0 Hz, 1H), 1.50 (s, 9H), 1.39-1.21 (m, 8H), 1.12 (t, J=12.5 Hz, 1H), 0.91-0.74 (m, 3H).

Step B. (1R,2S,5R)-1-Amino-2-(((S)-2-amino-3-hydroxy-3-methylbutanamido)methyl)-5-(2-borono-ethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-3-hy-droxy-3-methylbutanamido)methyl)cyclohexane-1-carbox-ylic acid (9 mg, 0.02 mmol) and 2 M HCl$_{aq}$ (2 mL). The crude material was purified by preparative HPLC (0.1-3% of acetonitrile in water) to give the corresponding product (7.6 mg, 87% yield, white solid). ESI+MS: m/z=359.95 (M+1)$^+$; ESI-MS: m/z=358.00 (M–1)$^-$. $^1$H NMR (700 MHz, deuterium oxide) δ 3.87 (s, 1H), 3.71 (dd, J=13.8, 2.8 Hz, 1H), 3.06 (dd, J=13.8, 9.9 Hz, 1H), 2.33-2.27 (m, 1H), 1.97-1.70 (m, 5H), 1.42 (s, 3H), 1.40-1.30 (m, 6H), 1.02-0.92 (m, 1H), 0.82 (dd, J=9.2, 6.8 Hz, 2H).

Example 17. (1R,2S,5R)-1-Amino-2-(((S)-2-amino-4-(methylthio)butanamido)methyl)-5-(2-borono-ethyl)cyclohexane-1-carboxylic acid dihydrochloride x 2 HCl

Step A. (1R,2S,5R)-1-Amino-5-(2-boronoethyl)-2-(((S)-2-((tert-butoxycarbonyl)amino)-4-(methylthio)butanamido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (40 mg, 0.13 mmol), Boc-L-Met-OSu (48 mg, 0.14 mmol), TEA (88 μL, 0.63 mmol) and DMF (2 mL). The residue was purified by preparative HPLC (1-55% of acetonitrile in water) to give the corresponding product (30 mg, 50% yield, white solid). ESI+MS: m/z=476.00 (M+1)$^+$; ESI-MS: m/z=474.00 (M–1)$^-$. $^1$H NMR (700 MHz, metha-nol-d$_4$) δ 4.09 (dd, J=9.0, 5.1 Hz, 1H), 3.55 (dd, J=14.2, 2.6 Hz, 1H), 2.86 (dd, J=13.1, 8.5 Hz, 1H), 2.60-2.54 (m, 1H), 2.52-2.47 (m, 1H), 2.19-2.13 (m, 1H), 2.09 (s, 3H), 2.03-1.94 (m, 2H), 1.87 (ddd, J=17.6, 10.8, 3.0 Hz, 4H), 1.70-1.64 (m, 1H), 1.45 (s, 9H), 1.31-1.23 (m, 3H), 1.08 (t, J=12.5 Hz, 1H), 0.80-0.74 (m, 2H).

Step B. (1R,2S,5R)-1-Amino-2-(((S)-2-amino-4-(methylthio)butanamido)methyl)-5-(2-boronoethyl)cyclohexane-1-carboxylic acid dihydrochloride The title compound was obtained in the same manner as in Example 3, step B, using (1R,2S,5R)-1-amino-5-(2-bo-ronoethyl)-2-(((S)-2-((tert-butoxycarbonyl)amino)-4-(meth-ylthio)butanamido)methyl)cyclohexane-1-carboxylic acid (30 mg, 0.063 mmol) and 2 M HCl$_{aq}$ (2 mL). The crude material was purified by preparative HPLC (0.1-15% of acetonitrile in water) to give the corresponding product (20.9 mg, 75% yield, white solid). ESI+MS: m/z=375.95 (M+1)$^+$; ESI-MS: m/z=374.00 (M–1)$^-$. $^1$H NMR (700 MHz, deuterium oxide) δ 4.14 (t, J=6.6 Hz, 1H), 3.70 (dd, J=13.7, 2.1 Hz, 1H), 3.04 (dd, J=13.8, 9.7 Hz, 1H), 2.70-2.57 (m, 2H), 2.30 (d, J=12.1 Hz, 1H), 2.22 (ddd, J=14.3, 7.2, 3.5 Hz, 2H), 2.16 (s, 3H), 1.99-1.87 (m, 3H), 1.85-1.72 (m, 2H), 1.36 (dt, J=25.8, 10.1 Hz, 3H), 0.94 (qd, J=12.9, 3.1 Hz, 1H), 0.82 (dd, J=9.2, 7.0 Hz, 2H).

Example 18. (1R,2S,5R)-1-Amino-2-(((S)-2-amino-3-(1H-indol-3-yl)propanamido)methyl)-5-(2-borono-ethyl)cyclohexane-1-carboxylic acid dihydrochloride x 2 HCl

Step A. (1R,2S,5R)-1-Amino-5-(2-boronoethyl)-2-(((S)-2-((tert-butoxycarbonyl)amino)-3-(1H-indol-3-yl)propanamido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (40 mg, 0.13 mmol), Boc-L-Trp-OSu (56 mg, 0.14 mmol), TEA (88 μL, 0.63 mmol) and DMF (2 mL). The residue was purified by preparative HPLC (1-55% of acetonitrile in water) to give the corresponding product (38 mg, 56% yield, white solid). ESI+MS: m/z=531.20 (M+1)$^+$; ESI-MS: m/z=529.05 (M–1)$^-$. $^1$H NMR (700 MHz, metha-nol-d$_4$) δ 7.58 (d, J=7.9 Hz, 1H), 7.33 (d, J=8.2 Hz, 1H), 7.12-7.07 (m, 2H), 7.03 (t, J=7.4 Hz, 1H), 4.27 (t, J=7.3 Hz, 1H), 3.43 (d, J=12.5 Hz, 1H), 3.18 (dd, J=14.3, 7.6 Hz, 1H), 3.07 (dd, J=14.2, 7.1 Hz, 1H), 2.66 (dd, J=12.4, 9.1 Hz, 1H), 2.09 (d, J=10.9 Hz, 1H), 1.93-1.81 (m, 1H), 1.76-1.59 (m, 2H), 1.41 (s, 9H), 1.34-1.27 (m, 2H), 1.25 (dd, J=15.2, 7.8 Hz, 2H), 0.99 (t, J=12.4 Hz, 1H), 0.80-0.70 (m, 2H), 0.69-0.62 (m, 1H).

Step B. (1R,2S,5R)-1-Amino-2-(((S)-2-amino-3-(1H-indol-3-yl)propanamido)methyl)-5-(2-borono-ethyl)cyclohexane-1-carboxylic acid dihydrochloride The title compound was obtained in the same manner as in Example 3, step B, using (1R,2S,5R)-1-amino-5-(2-bo-ronoethyl)-2-(((S)-2-((tert-butoxycarbonyl)amino)-3-(1H-indol-3-yl)propanamido)methyl)cyclohexane-1-carboxylic acid (38 mg, 0.072 mmol) and 2 M $HCl_{aq}$ (2 mL). The crude material was purified by preparative HPLC (0.1-15% of acetonitrile in water) to give the corresponding product (20.8 mg, 58% yield, white solid). ESI+MS: m/z=431.00 (M+1)$^+$; ESI-MS: m/z=429.00 (M–1)$^-$. $^1$H NMR (700 MHz, deuterium oxide) δ 7.69 (d, J=7.9 Hz, 1H), 7.59 (d, J=8.2 Hz, 1H), 7.36-7.29 (m, 2H), 7.27-7.23 (m, 1H), 4.27 (dd, J=10.5, 5.6 Hz, 1H), 3.60 (dd, J=13.7, 2.7 Hz, 1H), 3.45 (dd, J=14.0, 5.5 Hz, 1H), 3.34 (dd, J=14.1, 10.5 Hz, 1H), 2.55 (dd, J=13.8, 10.1 Hz, 1H), 2.16 (d, J=12.9 Hz, 1H), 1.68-1.61 (m, 2H), 1.34 (dd, J=15.3, 7.3 Hz, 2H), 1.26-1.11 (m, 3H), 0.82-0.78 (m, 2H), 0.67 (ddd, J=10.6, 6.5, 3.4 Hz, 1H), 0.58 (qd, J=13.4, 3.7 Hz, 1H).

Example 19. (1R,2S,5R)-1-Amino-2-(((2S,3R)-2-amino-3-hydroxybutanamido)methyl)-5-(2-borono-ethyl)cyclohexane-1-carboxylic acid dihydrochloride x 2 HCl

Step A. (1R,2S,5R)-1-Amino-5-(2-boronoethyl)-2-(((2S,3R)-2-((tert-butoxycarbonyl)amino)-3-hy-droxybutanamido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (40 mg, 0.13 mmol), Boc-L-Thr-OSu (44 mg, 0.14 mmol), TEA (88 μL, 0.63 mmol) and DMF (2 mL). The residue was purified by preparative HPLC (1-55% of acetonitrile in water) to give the corresponding product (25 mg, 45% yield, white solid). ESI+MS: m/z=446.05 (M+1)$^+$; ESI-MS: m/z=444.05 (M–1)$^-$. $^1$H NMR (700 MHz, metha-nol-d$_4$) δ 4.16-4.11 (m, 1H), 3.91 (d, J=3.0 Hz, 1H), 3.53 (dd, J=13.9, 4.1 Hz, 1H), 2.92 (dd, J=13.8, 8.2 Hz, 1H), 2.15 (d, J=11.1 Hz, 1H), 1.99-1.78 (m, 4H), 1.74-1.66 (m, 1H), 1.46 (s, 9H), 1.32-1.25 (m, 3H), 1.19 (d, J=6.3 Hz, 3H), 1.10 (t, J=12.6 Hz, 1H), 0.87-0.73 (m, 2H).

Step B. (1R,2S,5R)-1-Amino-2-(((2S,3R)-2-amino-3-hydroxybutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-bo-ronoethyl)-2-(((2S,3R)-2-((tert-butoxycarbonyl)amino)-3-hydroxybutanamido)methyl)cyclohexane-1-carboxylic acid (25 mg, 0.056 mmol) and 2 M $HCl_{aq}$ (2 mL). The crude material was purified by preparative HPLC (0.1-2% of acetonitrile in water) to give the corresponding product (14.1 mg, 61% yield, white solid). ESI+MS: m/z=345.95 (M+1)$^+$; ESI-MS: m/z=343.95 (M–1)$^-$. $^1$H NMR (700 MHz, deuterium oxide) δ 4.23-4.16 (m, 1H), 3.88 (d, J=6.0 Hz, 1H), 3.67 (dd, J=13.9, 2.9 Hz, 1H), 3.07 (dd, J=13.9, 9.3 Hz, 1H), 2.28-2.20 (m, 1H), 1.99-1.75 (m, 5H), 1.37 (dt, J=15.8, 8.0 Hz, 2H), 1.34 (d, J=6.5 Hz, 3H), 1.28 (t, J=12.7 Hz, 1H), 0.94 (ddd, J=14.8, 12.3, 3.2 Hz, 1H), 0.82 (dd, J=9.2, 7.0 Hz, 2H).

Example 20. (1R,2S,5R)-1-Amino-2-(((S)-2-amino-pentanamido)methyl)-5-(2-boronoethyl)cyclo-hexane-1-carboxylic acid dihydrochloride x 2 HCl

Step A. (1R,2S,5R)-1-Amino-5-(2-boronoethyl)-2-(((S)-2-((tert-butoxycarbonyl)amino)pentanamido)methyl)cyclohexane-1-carboxylic acid The title compound was obtained in the same manner as in Example 1, step E, using (1R,2S,5R)-1-amino-2-(ami-nomethyl)-5-(2-boronoethyl)cyclohexane-1-carboxylic acid dihydrochloride (34 mg, 0.11 mmol), Boc-L-Nva-OSu (37 mg, 0.12 mmol), TEA (75 μL, 0.63 mmol) and DMF (2 mL). The residue was purified by preparative HPLC (1-55% of acetonitrile in water) to give the corresponding product (29 mg, 59% yield, white solid). ESI+MS: m/z=444.05 (M+1)$^+$; ESI-MS: m/z=442.00 (M–1)$^-$. $^1$H NMR (700 MHz, metha-nol-d$_4$) δ 3.91 (dd, J=8.8, 5.5 Hz, 1H), 3.60-3.51 (m, 1H), 2.91-2.79 (m, 1H), 2.18-2.11 (m, 1H), 2.02-1.87 (m, 2H), 1.84 (d, J=13.1 Hz, 1H), 1.78 (d, J=13.3 Hz, 1H), 1.72-1.63 (m, 2H), 1.56 (dddd, J=13.5, 9.7, 8.7, 4.9 Hz, 1H), 1.45 (s, 9H), 1.40-1.32 (m, 2H), 1.27 (q, J=7.7 Hz, 2H), 1.08 (t, J=12.5 Hz, 1H), 0.94 (t, J=7.4 Hz, 3H), 0.88-0.71 (m, 3H).

Step B. (1R,2S,5R)-1-Amino-2-(((S)-2-aminopen-tanamido)methyl)-5-(2-boronoethyl)cyclohexane-1-carboxylic acid dihydrochloride The title compound was obtained in the same manner as in Example 3, step B, using (1R,2S,5R)-1-amino-5-(2-bo-ronoethyl)-2-(((S)-2-((tert-butoxycarbonyl)amino)pentana-mido)methyl)cyclohexane-1-carboxylic acid (28 mg, 0.063 mmol) and 2 M $HCl_{aq}$ (2 mL). The desired product was obtained as a white solid (23.6 mg, 90% yield). ESI+MS: m/z=344.00 (M+1)$^+$; ESI-MS: m/z=342.05 (M–1)$^-$. $^1$H NMR (700 MHz, deuterium oxide) δ 4.01 (t, J=6.6 Hz, 1H), 3.69 (dd, J=13.9, 2.5 Hz, 1H), 3.04 (dd, J=13.8, 9.9 Hz, 1H), 2.30 (ddd, J=13.2, 3.6, 1.8 Hz, 1H), 2.01-1.69 (m, 7H), 1.48-1.29 (m, 5H), 0.98 (t, J=7.3 Hz, 3H), 0.96-0.89 (m, 1H), 0.82 (td, J=7.5, 1.8 Hz, 2H).

Example 21. (1R,2S,5R)-1-Amino-2-((2-amino-2,3-dimethylbutanamido)methyl)-5-(2-boronoethyl)cyclohexane-1-carboxylic acid dihydrochloride

Step A. 2,5-Dioxopyrrolidin-1-yl 2-((tert-butoxycarbonyl)amino)-2,3-dimethylbutanoate The title compound was obtained in the same manner as in Example 11, step A, using (S)-2-((tert-butoxycarbonyl)amino)-2,3-dimethylbutanoic acid (100 mg, 0.43 mmol), TEA (151 μL, 1.08 mmol), N,N'-disuccinimidyl carbonate (90% of purity, 148 mg, 0.52 mmol) and dry THF (5 mL). The desired product was obtained as a white solid (105 mg, 74% yield). ESI+MS: m/z=351.00 (M+23)$^+$. $^1$H NMR (700 MHz, chloroform-d) δ 4.91 (s, 1H), 2.90-2.74 (m, 4H), 2.30-2.19 (m, 1H), 1.63 (s, 3H), 1.48 (s, 9H), 1.07 (d, J=4.6 Hz, 3H), 1.06 (d, J=4.7 Hz, 3H).

Step B. (1R,2S,5R)-1-Amino-5-(2-boronoethyl)-2-((2-((tert-butoxycarbonyl)amino)-2,3-dimethylbutanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), 2,5-dioxopyrrolidin-1-yl 2-((tert-butoxycarbonyl)-amino)-2,3-dimethylbutanoate (43 mg, 0.13 mmol), TEA (84 μL, 0.60 mmol) and DMF (2 mL). The residue was purified by preparative HPLC (1-60% of acetonitrile in water) to give the corresponding product (15 mg, 27% yield, white solid). ESI+MS:

m/z=458.10 (M+1)$^+$; ESI-MS: m/z=456.15 (M-1)$^-$. $^1$H NMR (700 MHz, methanol-d$_4$) δ 3.57 (dd, J=14.1, 3.0 Hz, 1H), 2.77-2.66 (m, 1H), 2.15 (ddd, J=13.0, 3.5, 1.9 Hz, 1H), 1.98-1.86 (m, 3H), 1.86-1.75 (m, 2H), 1.66-1.58 (m, 1H), 1.45 (s, 9H), 1.35 (s, 3H), 1.30-1.24 (m, 2H), 1.09 (t, J=12.5 Hz, 1H), 0.95 (d, J=6.8 Hz, 3H), 0.86 (d, J=6.8 Hz, 3H), 0.84-0.69 (m, 3H).

Step C. (1R,2S,5R)-1-Amino-2-((2-amino-2,3-dimethylbutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-((2-((tert-butoxycarbonyl)amino)-2,3-dimethylbutanamido)methyl)cyclohexane-1-carboxylic acid (13 mg, 0.028 mmol) and 2 M HCl$_{aq}$ (2 mL). The desired product was obtained as a white solid (11.4 mg, 95% yield). ESI+MS: m/z=357.95 (M+1)$^+$; ESI-MS: m/z=356.00 (M-1)$^-$. $^1$H NMR (700 MHz, deuterium oxide) δ 3.64 (dd, J=13.8, 2.5 Hz, 1H), 3.09 (dd, J=13.8, 9.7 Hz, 1H), 2.30 (ddd, J=13.1, 3.6, 1.8 Hz, 1H), 2.26-2.17 (m, 1H), 1.98-1.86 (m, 3H), 1.82-1.70 (m, 2H), 1.60 (s, 3H), 1.43-1.24 (m, 3H), 1.06 (d, J=6.9 Hz, 3H), 1.00 (d, J=7.0 Hz, 3H), 0.94 (qd, J=13.2, 3.7 Hz, 1H), 0.82 (td, J=7.5, 1.5 Hz, 2H).

Example 22. (1R,2S,5R)-1-Amino-2-(((R)-2-aminopropanamido)methyl)-5-(2-boronoethyl)cyclohexane-1-carboxylic acid dihydrochloride

Step A. (1R,2S,5R)-1-Amino-5-(2-boronoethyl)-2-(((R)-2-((tert-butoxycarbonyl)amino)propanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (38 mg, 0.12 mmol), Boc-D-Ala-OSu (38 mg, 0.13 mmol), TEA (84 μL, 0.60 mmol) and DMF (2 mL). The residue was purified by preparative HPLC (1-50% of acetonitrile in water) to give the corresponding product (29 mg, 58% yield, white solid). ESI+MS: m/z=416.00 (M+1)$^+$; ESI-MS: m/z=413.90 (M-1)$^-$. $^1$H NMR (700 MHz, methanol-d$_4$) δ 4.02 (dd, J=14.2, 7.1 Hz, 1H), 3.57-3.49 (m, 1H), 2.92 (dd, J=13.8, 7.7 Hz, 1H), 2.21-2.16 (m, 1H), 2.08-1.98 (m, 1H), 1.98-1.82 (m, 3H), 1.77-1.69 (m, 1H), 1.49 (s, 9H), 1.36-1.26 (m, 5H), 1.10 (t, J=12.5 Hz, 1H), 0.94-0.76 (m, 3H).

Step B. (1R,2S,5R)-1-Amino-2-(((R)-2-aminopropanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((R)-2-((tert-butoxycarbonyl)amino)propanamido)methyl)cyclohexane-1-carboxylic acid (28 mg, 0.067 mmol) and 2 M HCl$_{aq}$ (2 mL). The desired product was obtained as a white solid (23.5 mg, 90% yield). ESI+MS: m/z=315.95 (M+1)$^+$; ESI-MS: m/z=314.05 (M−1)$^-$. $^1$H NMR (700 MHz, deuterium oxide) δ 4.09 (q, J=7.1 Hz, 1H), 3.54 (dd, J=13.8, 2.9 Hz, 1H), 3.20 (dd, J=13.9, 9.4 Hz, 1H), 2.31-2.27 (m, 1H), 1.96-1.86 (m, 3H), 1.85-1.70 (m, 2H), 1.55 (d, J=7.1 Hz, 3H), 1.41-1.31 (m, 3H), 0.95 (qd, J=13.2, 3.8 Hz, 1H), 0.82 (dd, J=9.3, 6.8 Hz, 2H).

Example 23. (1R,2S,5R)-1-Amino-2-(((R)-2-amino-3-methylbutanamido)methyl)-5-(2-boronoethyl)cyclohexane-1-carboxylic acid dihydrochloride

Step A. 2,5-dioxopyrrolidin-1-yl (tert-butoxycarbonyl)-D-valinate (Boc-D-Val-OSu)

The title compound was obtained in the same manner as in Example 11, step A, using Boc-D-Val-OH (500 mg, 2.30 mmol), TEA (802 μL, 5.75 mmol), N,N'-disuccinimidyl carbonate (90% of purity, 707 mg, 2.76 mmol) and dry THF (20 mL). The desired product was obtained as a white solid (720 mg, 99% yield). ESI+MS: m/z=359.00 (M−56+1)$^+$. $^1$H NMR (700 MHz, chloroform-d) δ 4.99 (d, J=9.2 Hz, 1H), 4.60 (dd, J=9.3, 4.9 Hz, 1H), 2.84 (s, 4H), 2.35-2.23 (m, 1H), 1.46 (s, 9H), 1.05 (dd, J=23.8, 6.9 Hz, 6H).

Step B. (1R,2S,5R)-1-Amino-5-(2-boronoethyl)-2-(((R)-2-((tert-butoxycarbonyl)amino)-3-methylbutanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (45 mg, 0.14 mmol), Boc-D-Val-OSu (49 mg, 0.16 mmol), TEA (100 μL, 0.71 mmol) and DMF (2 mL). The residue was purified by preparative HPLC (1-60% of acetonitrile in water) to give the corresponding product (40 mg, 64% yield, white solid). ESI+MS: m/z=444.10 (M+1)$^+$; ESI-MS: m/z=441.95 (M−1)$^-$. $^1$H NMR (700 MHz, methanol-d$_4$) δ 3.82 (d, J=6.9 Hz, 1H), 3.62 (dd, J=14.2, 2.0 Hz, 1H), 2.85 (dd, J=13.7, 8.6 Hz, 1H), 2.18 (d, J=13.9 Hz, 1H), 2.08-1.85 (m, 5H), 1.73-1.66 (m, 1H), 1.48 (s, 9H), 1.34-1.23 (m, 2H), 1.10 (t, J=12.4 Hz, 1H), 0.96 (dd, J=10.0, 6.9 Hz, 6H), 0.89-0.75 (m, 3H).

Step C. (1R,2S,5R)-1-Amino-2-(((R)-2-amino-3-methylbutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((R)-2-((tert-butoxycarbonyl)amino)-3-methylbutanamido)methyl)cyclohexane-1-carboxylic acid (38 mg, 0.09 mmol) and 2 M HCl$_{aq}$ (2 mL). The crude material was purified by preparative HPLC (0.1-4% of acetonitrile in water) to give the corresponding product (23.1 mg, 65% yield, white solid). ESI+MS: m/z=344.00 (M+1)$^+$; ESI-MS: m/z=341.90 (M−1)$^-$. $^1$H NMR (700 MHz, deuterium oxide) δ 3.80 (d, J=5.9 Hz, 1H), 3.60 (dd, J=13.7, 2.6 Hz, 1H), 3.13 (dd, J=13.8, 10.0 Hz, 1H), 2.30 (ddd, J=13.0, 3.6, 1.5 Hz, 1H), 2.23 (dq, J=13.6, 6.8 Hz, 1H), 1.96-1.88 (m, 3H), 1.84-1.76 (m, 1H), 1.76-1.67 (m, 1H), 1.41-1.31 (m, 3H), 1.05 (dd, J=7.0, 3.3 Hz, 6H), 0.99-0.88 (m, 1H), 0.81 (dd, J=9.5, 6.8 Hz, 2H).

Example 24. (1R,2S,5R)-1-Amino-2-(((S)-2-amino-N-methylpropanamido)methyl)-5-(2-boronoethyl)cyclohexane-1-carboxylic acid dihydrochloride

Step A. (1R,2S,5R)-1-Amino-5-(2-boronoethyl)-2-(((S)-2-((tert-butoxycarbonyl)amino)-N-methylpropanamido)methyl)cyclohexane-1-carboxylic acid The title compound was obtained in the same manner as in Example 1, step E, using (1R,2S,5R)-1-amino-5-(2-boronoethyl)-2-((methylamino)methyl)cyclohexane-1-carboxylic acid dihydrochloride (compound was synthesized according to procedure from U.S. Pat. No. 10,391,077 B2) (20 mg, 0.06 mmol), Boc-L-Ala-OSu (19 mg, 0.07 mmol), TEA (42 μL, 0.30 mmol) and DMF (1 mL). The residue was purified by preparative HPLC (1-55% of acetonitrile in water) to give the corresponding product (3 mg, 12% yield, white solid, 4:1 mixture of rotamers in CD30D at room temperature based on NMR). ESI+MS: m/z=430.05 (M+1)$^+$; ESI-MS: m/z=427.95 (M–1)$^-$. $^1$H NMR (700 MHz, methanol-d$_4$) δ 4.54 (q, J=7.0 Hz, 1H), 3.92-3.86 (m, 0.20H), 3.74-3.66 (m, 0.80H), 3.21 (s, 2.40H), 3.19-3.13 (m, 1H), 2.97 (s, 0.60H), 2.30-2.25 (m, 0.20H), 2.25-2.20 (m, 0.80H), 2.09-1.94 (m, 2H), 1.95-1.85 (m, 2H), 1.86-1.74 (m, 1H), 1.47 (s, 9H), 1.38-1.32 (m, 2H), 1.29 (d, J=6.9 Hz, 3H), 1.18 (t, J=12.7 Hz, 1H), 0.97-0.87 (m, 1H), 0.86-0.77 (m, 2H).

Step B. (1R,2S,5R)-1-Amino-2-(((S)-2-amino-N-methylpropanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-N-methylpropanamido)methyl)cyclohexane-1-carboxylic acid (2 mg, 0.005 mmol) and 2 M HCl$_{aq}$ (1 mL). The desired product was obtained as a white solid (1.7 mg, 91% yield, 9:1 mixture of rotamers in D$_2$O at room temperature based on NMR). ESI+MS: m/z=329.95 (M+1)$^+$; ESI-MS: m/z=327.90 (M–1)$^-$. $^1$H NMR (700 MHz, deuterium oxide) δ 4.53 (q, J=7.0 Hz, 1H), 3.67 (d, J=13.9 Hz, 0.90H), 3.60 (d, J=13.9 Hz, 0.10H), 3.49 (dd, J=14.1 Hz, 8.7 Hz, 0.10H), 3.34 (dd, J=14.1, 8.7 Hz, 0.90H), 3.19 (s, 2.70H), 3.00 (s, 0.30H), 2.25 (d, J=13.6 Hz, 0.10H), 2.21 (d, J=13.6 Hz, 0.90H), 2.00-1.78 (m, 5H), 1.60-1.52 (m, 3H), 1.41-1.33 (m, 2H), 1.24 (t, J=12.7 Hz, 1H), 0.94 (dd, J=25.2, 12.4 Hz, 1H), 0.83 (t, J=8.1 Hz, 2H).

Example 25. (1R,2S,5R)-1-Amino-2-(((S)-2-amino-N,3-dimethylbutanamido)methyl)-5-(2-boronoethyl)cyclohexane-1-carboxylic acid dihydrochloride

Step A. (1R,2S,5R)-1-Amino-5-(2-boronoethyl)-2-(((S)-2-((tert-butoxycarbonyl)amino)-N,3-dimethylbutanamido)methyl)cyclohexane-1-carboxylic acid The title compound was obtained in the same manner as in Example 1, step E, using (1R,2S,5R)-1-amino-5-(2-boronoethyl)-2-((methylamino)methyl)cyclohexane-1-carboxylic acid dihydrochloride (the compound was synthesized according to procedure from U.S. Pat. No. 10,391,077 B2) (10 mg, 0.03 mmol), Boc-L-Val-OSu (10 mg, 0.03 mmol), TEA (21 μL, 0.15 mmol) and DMF (1 mL). The residue was purified by preparative HPLC (1-60% of acetonitrile in water) to give the corresponding product (7 mg, 51% yield, white solid, 3:1 mixture of rotamers in CD$_3$OD at room temperature based on NMR). ESI+MS: m/z=458.15 (M+1)$^+$; ESI-MS: m/z=456.00 (M–1)$^-$. $^1$H NMR (700 MHz, methanol-d$_4$) δ 4.31 (d, J=7.5 Hz, 0.75H), 4.18 (d, J=7.5 Hz, 0.25H), 4.14 (d, J=14.0 Hz, 0.25H), 3.78 (d, J=14.0 Hz, 0.75H), 3.24 (s, 2.30H), 3.12-3.05 (m, 1H), 3.02 (s, 0.70H), 2.22 (d, J=12.3 Hz, 0.25H), 2.17 (d, J=12.3 Hz, 0.75H), 2.12-1.95 (m, 3H), 1.91-1.70 (m, 3H), 1.48 (s, 2.20H), 1.45 (s, 6.80H), 1.32-1.25 (m, 2H), 1.10 (t, J=12.2 Hz, 0.75H), 1.04 (t, J=12.2 Hz, 0.25H), 1.00-0.90 (m, 6H), 0.87-0.74 (m, 3H).

Step B. (1R,2S,5R)-1-Amino-2-(((S)-2-amino-N,3-dimethylbutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((S)-2-((tert-butoxycarbonyl)amino)-N,3-dimethylbutanamido)methyl)cyclohexane-1-carboxylic acid (6 mg, 0.01 mmol) and 2 M HCl$_{aq}$ (1 mL). The crude material was purified by preparative HPLC (1-20% of acetonitrile in water) to give the corresponding product (5 mg, 89% yield, white solid, 9:1 mixture of rotamers in D$_2$O at room temperature based on NMR). ESI+MS: m/z=358.00 (M+1)$^+$; ESI-MS: m/z=355.90 (M–1)$^-$. $^1$H NMR (700 MHz, deuterium oxide) δ 4.39 (d, J=5.0 Hz, 0.90H), 4.33 (d, J=5.0 Hz, 0.10H), 3.76 (dd, J=13.8, 2.7 Hz, 0.90H), 3.65 (dd, J=13.8, 2.7 Hz, 0.10H), 3.46 (dd, J=13.8, 9.9 Hz, 0.10H), 3.29 (dd, J=13.8, 9.9 Hz, 0.90H), 3.20 (s, 2.70H), 2.99 (s, 0.30H), 2.39-2.31 (m, 1H), 2.31-2.22 (m, 1H), 2.04-1.96 (m, 1H), 1.96-1.84 (m, 3H), 1.84-1.75 (m, 1H), 1.40-1.34 (m, 2H), 1.31 (t, J=12.7 Hz, 1H), 1.13 (d, J=7.0 Hz, 3H), 1.02 (d, J=7.0 Hz, 3H), 0.93 (qd, J=12.6, 5.4 Hz, 1H), 0.81 (dd, J=9.5, 6.8 Hz, 2H).

Example 26. (1R,2S,5R)-1-Amino-2-(((R)-2-amino-3-(1-methyl-1H-indol-3-yl)propanamido)methyl)-5-(2-boronoethyl)cyclohexane-1-carboxylic acid dihydrochloride Step A. (1R,2S,5R)-1-Amino-5-(2-boronoethyl)-2-(((R)-2-((tert-butoxycarbonyl)amino)-3-(1-methyl-1H-indol-3-yl)propanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (35 mg, 0.11 mmol), 1-Me-Boc-D-Trp-OSu (50 mg, 0.12 mmol), TEA (77 µL, 0.55 mmol) and DMF (2 mL). The residue was purified by preparative HPLC (1-60% of acetonitrile in water) to give the corresponding product (13 mg, 22% yield, white solid) ESI+MS: m/z=545.20 (M+1)$^+$; ESI-MS: m/z=542.95 (M−1)$^-$. $^1$H NMR (700 MHz, methanol-d$_4$) δ 7.58 (d, J=7.5 Hz, 1H), 7.31 (d, J=8.1 Hz, 1H), 7.16 (t, J=7.5 Hz, 1H), 7.05 (t, J=7.5 Hz, 1H), 7.00 (s, 1H), 4.27 (t, J=6.9 Hz, 1H), 3.75 (s, 3H), 3.47-3.38 (m, 1H), 3.22-3.14 (m, 1H), 3.06 (dd, J=14.7, 7.1 Hz, 1H), 2.75 (dd, J=14.0, 8.4 Hz, 1H), 2.14-2.08 (m, 1H), 2.00-1.90 (m, 1H), 1.83-1.74 (m, 2H), 1.64-1.52 (m, 2H), 1.39 (s, 9H), 1.28-1.19 (m, 2H), 1.03 (t, J=12.5 Hz, 1H), 0.83-0.67 (m, 3H).

Step B. (1R,2S,5R)-1-Amino-2-(((R)-2-amino-3-(1-methyl-1H-indol-3-yl)propanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((R)-2-((tert-butoxycarbonyl)amino)-3-(1-methyl-1H-indol-3-yl)propanamido)methyl)cyclohexane-1-carboxylic acid (12 mg, 0.02 mmol) and 2 M HCl$_{aq}$ (2 mL). The crude material was purified by preparative HPLC (1-30% of acetonitrile in water) to give the corresponding product (7.5 mg, 62% yield, white solid) ESI+MS: m/z=445.10 (M+1)$^+$; ESI-MS: m/z=443.00 (M−1)$^-$. $^1$H NMR (700 MHz, deuterium oxide) δ 7.65 (d, J=7.9 Hz, 1H), 7.55 (d, J=8.3 Hz, 1H), 7.37 (t, J=7.6 Hz, 1H), 7.27-7.22 (m, 2H), 4.25 (dd, J=9.1, 6.2 Hz, 1H), 3.83 (s, 3H), 3.44 (dd, J=14.4, 5.8 Hz, 1H), 3.36 (dd, J=14.4, 9.5 Hz, 1H), 3.27 (d, J=13.2 Hz, 1H), 2.90 (t, J=12.1 Hz, 1H), 2.18 (d, J=13.1 Hz, 1H), 1.77-1.66 (m, 2H), 1.51 (t, J=11.4 Hz, 1H), 1.37-1.27 (m, 2H), 1.20-1.07 (m, 2H), 0.93-0.87 (m, 1H), 0.80 (t, J=8.0 Hz, 2H), 0.68-0.58 (m, 1H).

Example 27. (1R,2S,5R)-1-Amino-2-(((R)-2-amino-3-mercaptopropanamido)methyl)-5-(2-boronoethyl)cyclohexane-1-carboxylic acid dihydrochloride Step A. (1R,2S,5R)-1-Amino-5-(2-boronoethyl)-2-(((R)-2-((tert-butoxycarbonyl)amino)-3-(tritylthio)propanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (33 mg, 0.1 mmol), Boc-L-Cys(Trt)-OSu (64 mg, 0.11 mmol), TEA (72 µL, 0.52 mmol) and DMF (2 mL). The residue was purified by preparative HPLC (10-90% of acetonitrile in water) to give the corresponding product (36 mg, 50% yield, white solid) ESI+MS: m/z=690.45 (M+1)$^+$; ESI-MS: m/z=688.05 (M−1)$^-$. $^1$H NMR (700 MHz, methanol-d$_4$) δ 7.44-7.41 (m, 6H), 7.36-7.32 (m, 6H), 7.29-7.26 (m, 3H), 4.00-3.91 (m, 1H), 3.67-3.51 (m, 1H), 2.85-2.73 (m, 1H), 2.61-2.44 (m, 2H), 2.17 (d, J=11.8 Hz, 1H), 2.05-1.96 (m, 1H), 1.94-1.80 (m, 3H), 1.74-1.63 (m, 1H), 1.48 (s, 9H), 1.32-1.25 (m, 2H), 1.09 (td, J=12.5, 3.7 Hz, 1H), 0.87-0.71 (m, 3H).

Step B. (1R,2S,5R)-1-Amino-2-(((R)-2-amino-3-mercaptopropanamido)methyl)-5-(2-boronoethyl)cyclohexane-1-carboxylic acid dihydrochloride (1R,2S,5R)-1-Amino-5-(2-boronoethyl)-2-(((R)-2-((tert-butoxycarbonyl)amino)-3-(tritylthio)propanamido)methyl)cyclohexane-1-carboxylic acid (35 mg, 0.05 mmol) was dissolved in DCM (3 mL) and cooled to 0° C. Trifluoroacetic acid (1 mL) was added dropwise and then triethylsilane (20 µL, 0.13 mmol). The resulting mixture was stirred at this temperature for 1 h. The reaction was concentrated and the residue purified by preparative HPLC (0.1-10% of acetonitrile in water) to give the corresponding product (10.7 mg, 50% yield, white solid, 4:1 mixture of rotamers in D$_2$O at room temperature based on NMR) ESI+MS: m/z=348.00 (M+1)$^+$; ESI-MS: m/z=345.85 (M−1)$^-$. $^1$H NMR (700 MHz, deuterium oxide) δ 4.39-4.33 (m, 0.20H), 4.23-4.18 (m, 0.80H), 3.69 (dd, J=13.8, 2.7 Hz, 0.80H), 3.58 (dd, J=13.8, 2.6 Hz, 0.20H), 3.36-3.27 (m, 0.20H), 3.18 (dd, J=13.8, 9.6 Hz, 0.20H), 3.14-3.04 (m, 2.60H), 2.31-2.25 (m, 1H), 1.98-1.87 (m, 3H), 1.86-1.70 (m, 2H), 1.40-1.29 (m, 3H), 0.99-0.90 (m, 1H), 0.85-0.79 (m, 2H).

Example 28. (1R,2S,5R)-1-Amino-5-(2-boronoethyl)-2-(((S)-2,5-diamino-5-oxopentanamido)methyl)cyclohexane-1-carboxylic acid dihydrochloride

Step A. (1R,2S,5R)-1-Amino-2-(((S)-5-amino-2-((tert-butoxycarbonyl)amino)-5-oxopentanamido)methyl)-5-(2-boronoethyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (40 mg, 0.13 mmol), Boc-L-Gln-OSu (48 mg, 0.14 mmol), TEA (88 μL, 0.63 mmol) and DMF (2 mL). The residue was purified by preparative HPLC (1-40% of acetonitrile in water) to give the corresponding product (8 mg, 13% yield, white solid) ESI+MS: m/z=473.35 (M+1)$^+$; ESI-MS: m/z=470.90 (M−1)$^-$. $^1$H NMR (700 MHz, methanol-d$_4$) δ 4.00 (dd, J=9.2, 5.1 Hz, 1H), 3.61 (d, J=13.5 Hz, 1H), 2.93-2.87 (m, 1H), 2.36 (t, J=7.6 Hz, 2H), 2.25 (d, J=12.8 Hz, 1H), 2.10-2.03 (m, 1H), 1.95-1.78 (m, 6H), 1.50 (s, 9H), 1.38-1.30 (m, 2H), 1.24 (t, J=12.7 Hz, 1H), 0.96-0.89 (m, 1H), 0.87-0.79 (m, 2H).

Step B. (1R,2S,5R)-1-Amino-5-(2-boronoethyl)-2-(((S)-2,5-diamino-5-oxopentanamido)methyl)cyclohexane-1-carboxylic acid dihydrochloride The title compound was obtained in the same manner as in Example 3, step B, using (1R,2S,5R)-1-amino-2-(((S)-5-amino-2-((tert-butoxycarbonyl)amino)-5-oxopentanamido)methyl)-5-(2-boronoethyl)cyclohexane-1-carboxylic acid (5 mg, 0.01 mmol) and 2 M HCl$_{aq}$ (1 mL). The crude material was purified by preparative HPLC (0.1-5% of acetonitrile in water) to give the corresponding product (1.8 mg, 36% yield, white solid) ESI+MS: m/z=373.00 (M+1)$^+$; ESI-MS: m/z=370.85 (M−1)$^-$. $^1$H NMR (700 MHz, deuterium oxide) 64.09 (t, J=6.4 Hz, 1H), 3.65 (dd, J=13.8, 1.6 Hz, 1H), 3.11 (dd, J=13.7, 9.3 Hz, 1H), 2.52-2.46 (m, 2H), 2.28 (d, J=12.5 Hz, 1H), 2.24-2.13 (m, 2H), 1.95 (d, J=12.6 Hz, 1H), 1.92-1.75 (m, 4H), 1.38 (dd, J=15.2, 7.4 Hz, 2H), 1.32 (t, J=12.7 Hz, 1H), 1.02-0.91 (m, 1H), 0.86-0.81 (m, 2H).

Example 29. (1R,2S,5R)-1-Amino-2-(((S)-2-amino-3-carboxypropanamido)methyl)-5-(2-boronoethyl)cyclohexane-1-carboxylic acid dihydrochloride

Step A. (1R,2S,5R)-1-Amino-2-(((S)-4-(benzyloxy)-2-((tert-butoxycarbonyl)amino)-4-oxobutanamido)methyl)-5-(2-boronoethyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (40 mg, 0.13 mmol), Boc-L-Asp(OBn)-OSu (58 mg, 0.14 mmol), TEA (88 μL, 0.63 mmol) and DMF (2 mL). The residue was purified by preparative HPLC (1-65% of acetonitrile in water) to give the corresponding product (15 mg, 22% yield, white solid) ESI+MS: m/z=550.20 (M+1)$^+$; ESI-MS: m/z=548.05 (M−1)$^-$. $^1$H NMR (700 MHz, methanol-d$_4$) δ 7.44-7.31 (m, 5H), 5.21-5.17 (m, 2H), 4.49-4.42 (m, 1H), 3.54 (dd, J=14.3, 2.9 Hz, 1H), 2.97-2.88 (m, 2H), 2.79 (dd, J=16.4, 7.7 Hz, 1H), 2.18 (d, J=12.7 Hz, 1H), 2.08-1.92 (m, 2H), 1.91-1.77 (m, 2H), 1.74-1.65 (m, 1H), 1.49 (s, 9H), 1.31 (dd, J=15.1, 8.1 Hz, 2H), 1.09 (t, J=12.4 Hz, 1H), 0.90-0.75 (m, 3H).

Step B. (1R,2S,5R)-1-Amino-2-(((S)-2-amino-4-(benzyloxy)-4-oxobutanamido)methyl)-5-(2-boronoethyl)cyclohexane-1-carboxylic acid dihydrochloride The title compound was obtained in the same manner as in Example 3, step B, using (1R,2S,5R)-1-amino-2-(((S)-4-(benzyloxy)-2-((tert-butoxycarbonyl)amino)-4-oxobutanamido)methyl)-5-(2-boronoethyl)cyclohexane-1-carboxylic acid (15 mg, 0.03 mmol) and 2 M HCl$_{aq}$ (1 mL). The desired product was obtained as a colorless film (14 mg, 99% yield). ESI+MS: m/z=450.05 (M+1)$^+$; ESI-MS: m/z=447.80 (M−1)$^-$. $^1$H NMR (700 MHz, deuterium oxide) δ 7.56-7.42 (m, 5H), 5.28 (s, 2H), 4.42-4.34 (m, 1H), 3.65 (dd, J=13.9, 2.8 Hz, 1H), 3.20 (d, J=5.8 Hz, 2H), 3.02-2.92 (m, 1H), 2.27 (d, J=12.6 Hz, 1H), 1.91-1.64 (m, 5H), 1.43-1.31 (m, 2H), 1.28 (t, J=12.7 Hz, 1H), 0.87-0.72 (m, 3H).

Step C. (1R,2S,5R)-1-Amino-2-(((S)-2-amino-3-carboxypropanamido)methyl)-5-(2-boronoethyl)cyclohexane-1-carboxylic acid dihydrochloride The title compound was obtained in the same manner like in Example 7, step C, using (1R,2S,5R)-1-amino-2-(((S)-2-amino-4-(benzyloxy)-4-oxobutanamido)methyl)-5-(2-boronoethyl)cyclohexane-1-carboxylic acid dihydrochloride (10 mg, 0.02 mmol), Pd/C (wet, 10%, 10 mg) and MeOH (2 mL). The crude material was purified by preparative HPLC (0.1-5% of acetonitrile in water) to give the corresponding product (3.8 mg, 46% yield, white solid) ESI+MS: m/z=360.00 (M+1)$^+$; ESI-MS: m/z=357.80 (M–1)$^-$. $^1$H NMR (700 MHz, deuterium oxide) δ 4.36 (t, J=6.1 Hz, 1H), 3.69 (d, J=13.5 Hz, 1H), 3.08 (d, J=6.2 Hz, 2H), 3.07-2.98 (m, 1H), 2.28 (d, J=11.1 Hz, 1H), 1.94 (d, J=13.5 Hz, 1H), 1.90-1.80 (m, 3H), 1.78-1.68 (m, 1H), 1.38 (dd, J=14.8, 7.3 Hz, 2H), 1.32 (t, J=12.7 Hz, 1H), 0.98-0.91 (m, 1H), 0.85-0.77 (m, 2H).

Example 30. (1R,2S,5R)-1-Amino-2-(((S)-2-amino-4-carboxybutanamido)methyl)-5-(2-boronoethyl)cyclohexane-1-carboxylic acid dihydrochloride

Step A. (1R,2S,5R)-1-Amino-5-(2-boronoethyl)-2-(((S)-5-(tert-butoxy)-2-((tert-butoxycarbonyl)amino)-5-oxopentanamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (45 mg, 0.14 mmol), Boc-L-Glu(OtBu)-OSu (62 mg, 0.16 mmol), TEA (99 µL, 0.71 mmol) and DMF (2 mL). The residue was purified by preparative HPLC (1-55% of acetonitrile in water) to give the corresponding product (47 mg, 62% yield, white solid) ESI+MS: m/z=530.25 (M+1)$^+$; ESI-MS: m/z=528.00 (M–1)$^-$. $^1$H NMR (700 MHz, methanol-d$_4$) δ 4.01 (dd, J=9.0, 5.4 Hz, 1H), 3.60 (dd, J=14.1, 2.9 Hz, 1H), 2.89 (dd, J=13.7, 8.5 Hz, 1H), 2.36 (t, J=7.4 Hz, 2H), 2.21-2.17 (m, 1H), 2.07-1.93 (m, 3H), 1.92-1.81 (m, 3H), 1.74-1.65 (m, 1H), 1.50 (s, 18H), 1.35-1.28 (m, 2H), 1.12 (t, J=12.5 Hz, 1H), 0.90-0.79 (m, 3H).

Step B. (1R,2S,5R)-1-Amino-2-(((S)-2-amino-4-carboxybutanamido)methyl)-5-(2-boronoethyl)cyclohexane-1-carboxylic acid dihydrochloride The title compound was obtained in the same manner as in Example 3, step B, using (1R,2S,5R)-1-amino-5-(2-boronoethyl)-2-(((S)-5-(tert-butoxy)-2-((tert-butoxycarbonyl)amino)-5-oxopentanamido)methyl)cyclohexane-1-carboxylic acid (45 mg, 0.09 mmol) and 2 M HCl$_{aq}$ (3 mL). The crude material was purified by preparative HPLC (0.1-5% of acetonitrile in water) to give the corresponding product (30.7 mg, 81% yield, white solid) ESI+MS: m/z=373.95 (M+1)$^+$; ESI-MS: m/z=371.80 (M–1)$^-$. $^1$H NMR (700 MHz, deuterium oxide) δ 4.09 (t, J=6.6 Hz, 1H), 3.67 (dd, J=13.8, 2.4 Hz, 1H), 3.09 (dd, J=13.8, 9.6 Hz, 1H), 2.63-2.52 (m, 2H), 2.30 (d, J=11.9 Hz, 1H), 2.25-2.18 (m, 2H), 1.97-1.72 (m, 5H), 1.41-1.31 (m, 3H), 0.96 (dt, J=12.5, 9.6 Hz, 1H), 0.83 (dd, J=9.3, 6.9 Hz, 2H).

Example 31. (1R,2S,5R)-1-Amino-5-(2-borono-ethyl)-2-((2-(methylamino)acetamido)methyl)cyclohexane-1-carboxylic acid dihydrochloride

Step A. (1R,2S,5R)-1-Amino-5-(2-boronoethyl)-2-((2-((tert-butoxycarbonyl)(methyl)amino)acetamido)methyl)cyclohexane-1-carboxylic acid The title compound was obtained in the same manner as in Example 1, step E, using (1R,2S,5R)-1-amino-2-(aminomethyl)-5-(2-boronoethyl)cyclohexane-1-carboxylic acid dihydrochloride (31 mg, 0.10 mmol), Boc-Sar-OSu (31 mg, 0.11 mmol), TEA (68 µL, 0.49 mmol) and DMF (1 mL). The residue was purified by preparative HPLC (1-50% of acetonitrile in water) to give the corresponding product (8 mg, 20% yield, white solid) ESI+MS: m/z=416.05 (M+1)$^+$; ESI-MS: m/z=413.90 (M–1)$^-$. $^1$H NMR (700 MHz, methanol-d$_4$) δ 3.95-3.84 (m, 2H), 3.65 (dd, J=61.9, 13.5 Hz, 1H), 2.98 (s, 3H), 2.96-2.84 (m, 1H), 2.23-2.17 (m, 1H), 2.06-1.82 (m, 4H), 1.79-1.68 (m, 1H), 1.50 (d, J=32.0 Hz, 9H), 1.32 (dd, J=15.5, 7.5 Hz, 2H), 1.12 (t, J=12.5 Hz, 1H), 0.93-0.77 (m, 3H).

Step B. (1R,2S,5R)-1-Amino-5-(2-boronoethyl)-2-((2-(methylamino)acetamido)methyl)cyclohexane-1-carboxylic acid dihydrochloride The title compound was obtained in the same manner as in Example 3, step B, using (1R,2S,5R)-1-amino-5-(2-boronoethyl)-2-((2-((tert-butoxycarbonyl)(methyl)amino)acetamido)methyl)cyclohexane-1-carboxylic acid (7 mg, 0.02 mmol) and 2 M HCl$_{aq}$ (1 mL). The desired product was obtained as a white solid (6.3 mg, 95% yield). ESI+MS: m/z=316.05 (M+1)$^+$; ESI-MS: m/z=313.90 (M–1)$^-$. $^1$H NMR (700 MHz, deuterium oxide) δ 3.92 (s, 2H), 3.58 (dd, J=13.9, 2.1 Hz, 1H), 3.18 (dd, J=13.8, 9.0 Hz, 1H), 2.81 (s, 3H), 2.27 (d, J=12.9 Hz, 1H), 1.97-1.87 (m, 3H), 1.87-1.81

(m, 1H), 1.77 (dt, J=23.8, 11.9 Hz, 1H), 1.38 (dd, J=15.0, 7.3 Hz, 2H), 1.31 (t, J=12.7 Hz, 1H), 0.99-0.92 (m, 1H), 0.86-0.81 (m, 2H).

Example 32. (2-((1R,3R,4S)-3-Amino-4-(((S)-2-amino-3-methylbutanamido)methyl)-3-(methoxycarbonyl)cyclohexyl)ethyl)boronic acid dihydrochloride To a solution of (1R,2S,5R)-1-amino-2-(((S)-2-amino-3-methylbutanamido)methyl)-5-(2-boronoethyl)cyclohexane-1-carboxylic acid dihydrochloride (20 mg, 0.05 mmol) in toluene (0.30 mL) and methanol (0.15 mL) was added dropwise 2M solution of (diazomethyl)trimethylsilane in $Et_2O$ (36 μL, 0.07 mmol). The mixture was stirred at room temperature for 3 h. The solvents were evaporated and the residue was purified by preparative HPLC (1-30% of acetonitrile in water) to give the corresponding product (1.2 mg, 6% yield, white solid). ESI+MS: m/z=358.00 (M+1)$^+$. $^1$H NMR (700 MHz, deuterium oxide) δ 3.92 (s, 3H), 3.82 (d, J=5.8 Hz, 1H), 3.71 (d, J=13.7 Hz, 1H), 2.97 (t, J=12.3 Hz, 1H), 2.32 (d, J=12.8 Hz, 1H), 2.29-2.20 (m, 1H), 2.00-1.86 (m, 3H), 1.79-1.67 (m, 2H), 1.45-1.32 (m, 3H), 1.07 (d, J=6.8 Hz, 6H), 1.00-0.92 (m, 1H), 0.82 (t, J=7.8 Hz, 2H).

Example 33. 2-(2-((1R,3R,4S)-3-Amino-4-(((S)-2-amino-3-methylbutanamido)methyl)-3-carboxycyclohexyl)ethyl)-4-(carboxymethyl)-6-oxo-1,3,2-dioxaborinane-4-carboxylic acid dihydrochloride To a solution of (1R,2S,5R)-1-amino-2-(((S)-2-amino-3-methylbutanamido)methyl)-5-(2-boronoethyl)cyclohexane-1-carboxylic acid dihydrochloride (10 mg, 0.02 mmol) in methanol (0.5 mL) citric acid monohydrate (5 mg, 0.02 mmol) was added and the resulting mixture was stirred at room temperature for 2 h. Reaction was concentrated to dryness and the crude product was triturated with acetonitrile (2×1 mL). The precipitate was filtered off and lyophilized to give the corresponding product (6.7 mg, 510% yield, white solid). $^1$H NMR (700 MHz, dimethyl sulfoxide-$d_6$) δ 8.53 (t, J=5.3 Hz, 1H), 8.45 (bs, 2H), 8.18-8.08 (m, 3H), 3.65-3.59 (m, 1H), 3.58-3.50 (m, 4H), 2.93-2.86 (m, 1H), 2.38-2.36 (m, 1H), 2.16-2.11 (m, 1H), 2.07-2.02 (m, 1H), 1.89-1.85 (m, 1H), 1.84-1.77 (m, 2H), 1.66-1.58 (m, 1H), 1.52 (qd, J=13.2, 3.6 Hz, 1H), 1.25-1.16 (m, 1H), 1.15-1.06 (m, 2H), 0.93 (dd, J=6.9, 1.4 Hz, 6H), 0.77-0.68 (m, 1H), 0.26-0.18 (m, 2H).

Example 34. (1R,2R,5R)-1-Amino-2-(((S)-2-amino-3-methylbutanamido)methyl)-5-(2-boronoethyl)cyclohexane-1-carboxylic acid dihydrochloride

Step A. (1R,2R,5R)-1-Acetamido-N-(tert-butyl)-2-((dibenzylamino)methyl)-5-vinylcyclohexane-1-carboxamide The title compound was obtained in the same manner as in Example 1, step A, using ethyl (1R,2R,4R)-2-acetamido-2-(tert-butylcarbamoyl)-4-vinylcyclohexane-1-carboxylate (1.05 g, 3.10 mmol), 1 M DIBAL-H in DCM (9.62 mL, 9.62 mmol), glacial acetic acid (0.89 mL, 15.51 mmol), N,N-dibenzylamine (0.9 mL, 4.65 mmol), sodium triacetoxyborohydride (2.63 g, 12.41 mmol) and dry DCM (42 mL). The residue was purified by silica gel flash chromatography (DCM/Acetone 80:1 to 20:1) and subsequently preparative HPLC (20-90% of acetonitrile in water) to give the corresponding product (15 mg, 1% yield, white solid). ESI+MS: m/z=476.60 (M+1)$^+$; ESI-MS: m/z=474.00 (M-1)$^-$. $^1$H NMR (700 MHz, chloroform-d) δ 8.72 (s, 1H), 7.36-7.33 (m, 4H), 7.31-7.27 (m, 6H), 7.07 (s, 1H), 5.60 (ddd, J=17.0, 10.4, 6.4 Hz, 1H), 4.88 (tt, J=10.3, 1.5 Hz, 2H), 3.85 (d, J=13.4 Hz, 2H), 3.38 (d, J=13.4 Hz, 2H), 3.07 (dd, J=13.3, 9.9 Hz, 1H), 2.75-2.69 (m, 1H), 2.65 (dd, J=14.1, 3.4 Hz, 1H), 2.38-2.31 (m, 1H), 2.26 (dd, J=13.4, 2.9 Hz, 1H), 1.85 (s, 3H), 1.79 (ddd, J=14.0, 9.1, 4.2 Hz, 1H), 1.47-1.43 (m, 1H), 1.33 (s, 9H), 1.26 (s, 1H), 0.96-0.86 (m, 2H).

Step B. (1R,2R,5R)-1-Acetamido-N-(tert-butyl)-2-((dibenzylamino)methyl)-5-(2-(4,4,5,5-tetramethyl-1,3,2-dioxaborolan-2-yl)ethyl)cyclohexane-1-carboxamide The title compound was obtained in the same manner as in Example 1, step B, using (1R,2R,5R)-1-acetamido-N-(tert-butyl)-2-((dibenzylamino)methyl)-5-vinylcyclohexane-1-carboxamide (13 mg, 0.003 mmol), dppe (0.6 mg, 0.002 mmol), bis(1,5-cyclooctadiene)-diiridium(I) dichloride (0.5 mg, 0.001 mmol), 4,4,5,5-tetramethyl-1,3,2-dioxaborolane (6 µL, 0.04 mmol) and DCM (1 mL). The residue was purified by silica gel flash chromatography (DCM/Acetone 50:1 to 15:1) to give the corresponding product (15 mg, 92% yield, colorless oil). ESI+MS: m/z=604.50 (M+1)$^+$; ESI-MS: m/z=602.15 (M−1)$^-$. $^1$H NMR (700 MHz, chloroform-d) δ 8.80 (s, 1H), 7.36-7.32 (m, 5H), 7.30-7.26 (m, 5H), 7.24 (bs, 1H), 3.88 (d, J=13.4 Hz, 2H), 3.32 (d, J=13.4 Hz, 2H), 3.07 (dd, J=13.3, 10.1 Hz, 1H), 2.82-2.77 (m, 1H), 2.74-2.70 (m, 1H), 2.19 (dd, J=13.4, 2.3 Hz, 1H), 1.81 (s, 3H), 1.76 (tt, J=14.3, 4.2 Hz, 1H), 1.46-1.37 (m, 2H), 1.32 (s, 9H), 1.27-1.25 (m, 2H), 1.24 (s, 12H), 0.87-0.79 (m, 2H), 0.75-0.64 (m, 3H).

Step C. (1R,2R,5R)-1-Amino-5-(2-boronoethyl)-2-((dibenzylamino)methyl)cyclohexane-1-carboxylic acid dihydrochloride x 2 HCl The title compound was obtained in the same manner as in Example 1, step C, (1R,2R,5R)-1-acetamido-N-(tert-butyl)-2-((dibenzylamino)methyl)-5-(2-(4,4,5,5-tetramethyl-1,3,2-dioxaborolan-2-yl)ethyl)cyclohexane-1-carboxamide (15 mg, 0.03 mmol) and 12 M HCl$_{aq}$ (3 mL). The residue was purified by preparative HPLC (1-50% of acetonitrile in water) to give the corresponding product (12 mg, 96% yield, white solid). ESI+MS: m/z=425.15 (M+1)$^+$; ESI-MS: m/z=404.90 (M−1−18)$^-$. $^1$H NMR (700 MHz, deuterium oxide) δ 7.62-7.37 (m, 10H), 4.61 (d, J=13.0 Hz, 2H), 4.40 (bs, 1H), 4.10 (bs, 1H), 3.17-3.09 (m, 2H), 2.71-2.60 (m, 1H), 2.09 (dd, J=14.3, 4.8 Hz, 1H), 1.63-1.49 (m, 2H), 1.40-1.26 (m, 3H), 1.23-1.09 (m, 2H), 0.75-0.54 (m, 3H).

Step D. (1R,2R,5R)-1-Amino-2-(aminomethyl)-5-(2-boronoethyl)cyclohexane-1-carboxylic acid dihydrochloride x 2 HCl The title compound was obtained in the same manner as in Example 1, step D, using (1R,2R,5R)-1-amino-5-(2-boronoethyl)-2-((dibenzylamino)methyl)cyclohexane-1-carboxylic acid dihydrochloride (22 mg, 0.04 mmol), Pd(OH)$_2$/C (20%, 15 mg) and MeOH (3 mL). The desired product was obtained as a colorless film (11.5 mg, 82% yield). ESI+MS: m/z=245.00 (M+1)$^+$; ESI-MS: m/z=224.70 (M−1−18)$^-$. $^1$H NMR (700 MHz, deuterium oxide) δ 3.19-3.06 (m, 2H), 2.27 (dd, J=12.6, 5.3 Hz, 1H), 1.98-1.90 (m, 1H), 1.83-1.76 (m, 1H), 1.75-1.66 (m, 2H), 1.53 (dd, J=14.0, 9.0 Hz, 1H), 1.48-1.42 (m, 2H), 1.40-1.34 (m, 1H), 1.32 (t, J=7.3 Hz, 1H), 0.91-0.77 (m, 2H).

Step E. (1R,2R,5R)-1-Amino-5-(2-boronoethyl)-2-(((S)-2-((tert-butoxycarbonyl)amino)-3-methylbutanamido)methyl)cyclohexane-1-carboxylic acid The title compound was obtained in the same manner as in Example 1, step E, using (1R,2R,5R)-1-amino-2-(aminomethyl)-5-(2-boronoethyl)cyclohexane-1-carboxylic acid dihydrochloride (11 mg, 0.04 mmol), Boc-L-Val-OSu (12 mg, 0.04 mmol), TEA (24 µL, 0.17 mmol) and DMF (1 mL). The residue was purified by preparative HPLC (1-60% of acetonitrile in water) to give the corresponding product (2 mg, 13% yield, white solid). ESI+MS: m/z=444.00 (M+1)$^+$; ESI-MS: m/z=441.95 (M−1)$^-$. $^1$H NMR (700 MHz, methanol-d$_4$) δ 3.87 (d, J=6.6 Hz, 1H), 3.39-3.37 (m, 1H), 3.19 (dd, J=13.8, 4.1 Hz, 1H), 2.41 (td, J=9.5, 4.5 Hz, 1H), 2.21 (dd, J=13.5, 4.5 Hz, 1H), 2.12-2.04 (m, 1H), 2.03-1.96 (m, 1H), 1.89-1.78 (m, 1H), 1.70-1.60 (m, 2H), 1.49 (s, 9H), 1.44-1.34 (m, 3H), 1.33-1.23 (m, 1H), 0.99 (dd, J=17.6, 6.8 Hz, 6H), 0.84 (dtd, J=22.5, 15.9, 8.7 Hz, 2H).

Step F. (1R,2R,5R)-1-Amino-2-(((S)-2-amino-3-methylbutanamido)methyl)-5-(2-boronoethyl)cyclohexane-1-carboxylic acid dihydrochloride The title compound was obtained in the same manner as in Example 3, step B, using (1R,2R,5R)-1-amino-5-(2-boronoethyl)-2-(((S)-2-((tert-butoxycarbonyl)amino)-3-methylbutanamido)methyl)cyclohexane-1-carboxylic acid (2 mg, 0.005 mmol) and 2 M HCl$_{aq}$ (1 mL). The reaction was concentrated and subsequently lyophilized to give the corresponding product (1.7 mg, 89% yield, white solid). ESI+MS: m/z=344.05 (M+1)$^+$; ESI-MS: m/z=323.80 (M−1−18)$^-$. $^1$H NMR (700 MHz, deuterium oxide) δ 3.82 (d, J=6.0 Hz, 1H), 3.46 (dd, J=13.5, 10.3 Hz, 1H), 3.36 (dd, J=13.7, 5.5 Hz, 1H), 2.58-2.51 (m, 1H), 2.30-2.22 (m, 2H), 1.83-1.74 (m, 2H), 1.73-1.63 (m, 2H), 1.59 (dd, J=14.0, 9.1 Hz, 1H), 1.50-1.39 (m, 2H), 1.38-1.31 (m, 1H), 1.10-1.06 (m, 6H), 0.91-0.79 (m, 2H).

Example 35. (1R,2S,5R)-2-(((S)-2-Aminopropanamido)methyl)-5-(2-boronoethyl)-1-(ethylamino)cyclohexane-1-carboxylic acid dihydrochloride

Step A. (1R,2S,5R)—N-(tert-Butyl)-2-((dibenzylamino)methyl)-1-(ethylamino)-5-vinylcyclohexane-1-carboxamide The title compound was obtained in the same manner as in Example 1, step A, using ethyl (1R,2R,4R)-2-acetamido-2-(tert-butylcarbamoyl)-4-vinylcyclohexane-1-carboxylate (1.05 g, 3.10 mmol), 1 M DIBAL-H in DCM (9.62 mL, 9.62 mmol), glacial acetic acid (0.89 mL, 15.51 mmol), N,N-dibenzylamine (0.9 mL, 4.65 mmol), sodium triacetoxyborohydride (2.63 g, 12.41 mmol) and dry DCM (42 mL). The residue was purified by silica gel flash chromatography (hexane/AcOEt 15:1 to 12:1) to give the corresponding product (55 mg, 4% yield, white solid). ESI+MS: m/z=462.60 (M+1)$^+$. $^1$H NMR (700 MHz, chloroform-d) δ 7.38-7.29 (m, 8H), 7.26-7.21 (m, 2H), 5.72 (ddd, J=17.2, 10.4, 6.7 Hz, 1H), 5.03-4.82 (m, 2H), 3.70 (d, J=13.5 Hz, 2H), 3.38 (d, J=13.5 Hz, 2H), 3.06-2.92 (m, 1H), 2.77-2.65 (m, 2H), 2.31 (dq, J=11.1, 7.3 Hz, 1H), 2.25 (dd, J=12.7, 9.3 Hz, 1H), 2.09-2.02 (m, 2H), 1.83-1.76 (m, 1H), 1.48-1.37 (m, 2H), 1.20 (s, 9H), 1.06 (t, J=7.1 Hz, 3H), 1.01-0.94 (m, 2H), 0.89-0.81 (m, 2H).

Step B. (1R,2S,5R)—N-(tert-Butyl)-2-((dibenzylamino)methyl)-1-(ethylamino)-5-(2-(4,4,5,5-tetramethyl-1,3,2-dioxaborolan-2-yl)ethyl)cyclohexane-1-carboxamide The title compound was obtained in the same manner as in Example 1, step B, using (1R,2S,5R)—N-(tert-butyl)-2-((dibenzylamino)methyl)-1-(ethylamino)-5-vinylcyclohexane-1-carboxamide (50 mg, 0.11 mmol), dppe (2.5 mg, 0.006 mmol), bis(1,5-cyclooctadiene)-diiridium(I) dichloride (2.1 mg, 0.003 mmol), 4,4,5,5-tetramethyl-1,3,2-dioxaborolane (24 μL, 0.16 mmol) and DCM (1 mL). The residue was purified by silica gel flash chromatography (hexane/AcOEt 15:1 to AcOEt) to give the corresponding product (57 mg, 89% yield, white solid). ESI+MS: m/z=590.50 (M+1)$^+$. $^1$H NMR (700 MHz, chloroform-d) δ 7.36 (s, 1H), 7.33-7.26 (m, 8H), 7.24-7.16 (m, 2H), 3.62 (d, J=13.5 Hz, 2H), 3.49 (s, 1H), 3.38 (d, J=13.5 Hz, 2H), 2.71-2.62 (m, 2H), 2.32-2.24 (m, 1H), 2.21 (dd, J=12.8, 8.5 Hz, 1H), 2.11-2.05 (m, 1H), 1.98-1.92 (m, 2H), 1.87-1.80 (m, 1H), 1.45-1.35 (m, 2H), 1.30-1.27 (m, 1H), 1.24 (s, 12H), 1.15 (s, 9H), 1.03 (t, J=7.1 Hz, 3H), 0.88 (dt, J=9.5, 2.1 Hz, 1H), 0.82-0.76 (m, 2H), 0.73-0.63 (m, 2H).

Step C. (1R,2S,5R)-5-(2-Boronoethyl)-2-((dibenzylamino)methyl)-1-(ethylamino)cyclohexane-1-carboxylic acid dihydrochloride The title compound was obtained in the same manner as in Example 1, step C, using (1R,2S,5R)—N-(tert-butyl)-2-((dibenzylamino)methyl)-1-(ethylamino)-5-(2-(4,4,5,5-tetramethyl-1,3,2-dioxaborolan-2-yl)ethyl)cyclohexane-1-carboxamide (55 mg, 0.09 mmol) and 12 M HCl$_{aq}$ (5 mL). The residue was purified by preparative HPLC (1-55% of acetonitrile in water) to give the corresponding product (26 mg, 53% yield, white solid). ESI+MS: m/z=453.20 (M+1)$^+$; ESI-MS: m/z=450.95 (M–1)$^-$. $^1$H NMR (700 MHz, deuterium oxide) δ 7.73-7.37 (m, 10H), 4.64-4.56 (m, 2H), 4.51-4.30 (m, 2H), 3.64-3.57 (m, 2H), 3.25 (dd, J=14.0, 11.2 Hz, 1H), 3.02-2.92 (m, 1H), 2.81-2.72 (m, 1H), 2.25-2.19 (m, 1H), 2.16-2.10 (m, 1H), 1.86-1.78 (m, 3H), 1.37-1.31 (m, 2H), 1.28 (t, J=7.2 Hz, 3H), 1.21 (t, J=7.1 Hz, 1H), 0.91-0.83 (m, 1H), 0.82-0.71 (m, 2H).

Step D. (1R,2S,5R)-2-(Aminomethyl)-5-(2-boronoethyl)-1-(ethylamino)cyclohexane-1-carboxylic acid dihydrochloride The title compound was obtained in the same manner as in Example 1, step D, using (1R,2S,5R)-5-(2-boronoethyl)-2-((dibenzylamino)methyl)-1-(ethylamino)cyclohexane-1-carboxylic acid dihydrochloride (26 mg, 0.05 mmol), $Pd(OH)_2/C$ (20%, 20 mg) and MeOH (5 mL). The desired product was obtained as a colorless film (16.9 mg, 99% yield). ESI+MS: m/z=272.95 (M+1)$^+$; ESI-MS: m/z=270.85 (M–1)$^-$. $^1$H NMR (700 MHz, methanol-$d_4$) δ 3.57 (dd, J=13.1, 2.2 Hz, 1H), 3.33-3.28 (m, 1H), 3.23-3.17 (m, 1H), 2.85-2.79 (m, 1H), 2.40-2.29 (m, 2H), 2.10-2.04 (m, 1H), 2.02-1.96 (m, 1H), 1.95-1.87 (m, 1H), 1.70 (qd, J=14.0, 3.8 Hz, 1H), 1.48-1.40 (m, 6H), 1.04 (qd, J=12.9, 3.5 Hz, 1H), 0.90-0.82 (m, 2H).

Step E. (1R,2S,5R)-5-(2-Boronoethyl)-2-(((S)-2-((tert-butoxycarbonyl)amino)propanamido)methyl)-1-(ethylamino)cyclohexane-1-carboxylic acid The title compound was obtained in the same manner as in Example 1, step E, using (1R,2S,5R)-2-(aminomethyl)-5-(2-boronoethyl)-1-(ethylamino)cyclohexane-1-carboxylic acid dihydrochloride (16 mg, 0.05 mmol), Boc-L-Ala-OSu (14.5 mg, 0.05 mmol), TEA (32 μL, 0.23 mmol) and DMF (1 mL). The residue was purified by preparative HPLC (1-55% of acetonitrile in water) to give the corresponding product (13 mg, 64% yield, white solid). ESI+MS: m/z=444.10 (M+1)$^+$; ESI-MS: m/z=441.95 (M–1)$^-$. $^1$H NMR (700 MHz, methanol-$d_4$) δ 3.99 (q, J=7.2 Hz, 1H), 3.79 (d, J=14.2 Hz, 1H), 3.30-3.19 (m, 1H), 3.13-3.03 (m, 1H), 2.78-2.68 (m, 1H), 2.22-2.14 (m, 2H), 1.91-1.82 (m, 2H), 1.80-1.64 (m, 2H), 1.53-1.50 (m, 1H), 1.48 (s, 9H), 1.40 (t, J=7.2 Hz, 3H), 1.36-1.26 (m, 5H), 1.12-1.00 (m, 1H), 0.89-0.77 (m, 2H).

Step F. (1R,2S,5R)-2-(((S)-2-Aminopropanamido)methyl)-5-(2-boronoethyl)-1-(ethylamino)cyclohexane-1-carboxylic acid dihydrochloride The title compound was obtained in the same manner as in Example 3, step B, using (1R,2S,5R)-5-(2-boronoethyl)-2-(((S)-2-((tert-butoxycarbonyl)amino)propanamido)methyl)-1-(ethylamino)cyclohexane-1-carboxylic acid (10 mg, 0.02 mmol) and 2 M HCl$_{aq}$ (1 mL). The crude material was purified by preparative HPLC (0.1-15% of acetonitrile in water) to give the corresponding product (4.4 mg, 47% yield, white solid). ESI+MS: m/z=344.00 (M+1)$^+$; ESI-MS: m/z=341.90 (M–1)$^-$. $^1$H NMR (700 MHz, deuterium oxide) δ 4.09 (q, J=7.1 Hz, 1H), 3.75 (dd, J=13.9, 2.6 Hz, 1H), 3.31 (dq, J=14.6, 7.3 Hz, 1H), 3.16 (dq, J=14.6, 7.2 Hz, 1H), 2.95 (dd, J=14.0, 10.0 Hz, 1H), 2.27 (dd, J=12.8, 3.3 Hz, 1H), 2.02-1.86 (m, 4H), 1.63-1.57 (m, 1H), 1.55 (d, J=7.1 Hz, 3H), 1.43-1.35 (m, 5H), 1.28 (t, J=12.4 Hz, 1H), 0.96-0.88 (m, 1H), 0.87-0.78 (m, 2H).

Example 36. (1R,2S,5R)-2-(((S)-2-Aminopropanamido)methyl)-5-(2-boronoethyl)-1-(methylamino)cyclohexane-1-carboxylic acid dihydrochloride

Step A. (1R,2S,5R)-5-(2-Boronoethyl)-1-((tert-butoxycarbonyl)amino)-2-((dibenzylamino)methyl)cyclohexane-1-carboxylic acid To a solution of (1R,2S,5R)-1-amino-5-(2-boronoethyl)-2-((dibenzylamino)methyl)cyclohexane-1-carboxylic acid dihydrochloride (135 mg, 0.27 mmol) in acetone (7 mL) were added saturated solution of $Na_2CO_3$ (7 mL) and di-tert-butyl dicarbonate (118 mg, 0.54 mmol). The resulting mixture was stirred at room temperature overnight. Inorganic contaminations were precipitated using acetone (10 mL) and were filtered off A filtrate was evaporated and the residue neutralized to pH~7 with 1 M aqueous solution of $KHSO_4$ and extracted with AcOEt (3×10 mL). The combined organic layers were dried over $Na_2SO_4$, filtered and concentrated in vacuo. The residue was purified by silica gel flash chromatography (DCM/MeOH 100:1 to 30:1) to give the corresponding product (70 mg, 49% yield, white solid). ESI+MS: m/z=525.30 (M+1)$^+$; ESI-MS: m/z=523.10 (M–1)$^-$. $^1$H NMR (700 MHz, methanol-$d_4$) δ 7.46-7.36 (m, 10H), 4.10-3.97 (m, 2H), 3.89-3.75 (m, 2H), 3.06 (dd, J=13.6, 5.8 Hz, 1H), 2.97-2.83 (m, 1H), 2.45-2.35 (m, 1H), 2.30-2.20 (m, 1H), 1.85-1.70 (m, 3H), 1.68-1.61 (m, 1H), 1.48 (s, 9H), 1.38-1.32 (m, 1H), 1.29-1.21 (m, 2H), 0.96-0.87 (m, 1H), 0.78 (dd, J=9.4, 6.9 Hz, 2H).

Step B. (1R,2S,5R)-5-(2-Boronoethyl)-2-((dibenzylamino)methyl)-1-(methylamino)cyclohexane-1-carboxylic acid dihydrochloride To a solution of (1R,2S,5R)-5-(2-boronoethyl)-1-((tert-butoxycarbonyl)amino)-2-((dibenzylamino)methyl)cyclohexane-1-carboxylic acid (70 mg, 0.13 mmol) in dry THF (2 mL), methyl iodide (66 µL, 1.06 mmol) was added. The resulting mixture was cooled to 0° C. and NaH (60% dispersion in mineral oil, 16 mg, 0.40 mmol) was slowly added. The cooling bath was removed and the reaction mixture was heated to 60° C. and stirred for 5 h at this temperature. The reaction was cooled to 0° C. and quenched with water (3 mL) and subsequently extracted with AcOEt (3×5 mL). The combined organic layers were dried over $Na_2SO_4$, filtered and concentrated in vacuo. The residue was purified by silica gel flash chromatography (DCM/MeOH 100:1 to 12:1) to give the mixture of product with and without methyl ester. The mixture of products was treated with 12 M $HCl_{aq}$ (1 mL) and heated at 100° C. overnight. The reaction mixture was concentrated under reduced pressure and the residue was purified by preparative HPLC (1-60% of acetonitrile in water) to give the corresponding product (20 mg, 29% yield, white solid). ESI+MS: m/z=439.15 (M+1)$^+$; ESI-MS: m/z=436.85 (M–1)$^-$. $^1$H NMR (700 MHz, deuterium oxide) δ 7.76-7.36 (m, 10H), 4.71-4.55 (m, 2H), 4.54-4.20 (m, 2H), 3.49 (dd, J=13.8, 2.5 Hz, 1H), 3.29-3.18 (m, 1H), 2.56 (s, 3H), 2.22 (d, J=12.5 Hz, 1H), 2.18 (t, J=10.3 Hz, 1H), 1.89-1.76 (m, 3H), 1.41-1.28 (m, 3H), 1.23 (t, J=12.5 Hz, 1H), 0.93-0.84 (m, 1H), 0.83-0.74 (m, 2H).

Step C. (1R,2S,5R)-2-(Aminomethyl)-5-(2-boronoethyl)-1-(methylamino)cyclohexane-1-carboxylic acid dihydrochloride The title compound was obtained in the same manner as in Example 1, step D, using (1R,2S,5R)-5-(2-boronoethyl)-2-((dibenzylamino)methyl)-1-(methylamino)cyclohexane-1-carboxylic acid dihydrochloride (19 mg, 0.04 mmol), Pd(OH)$_2$/C (20%, 10 mg) and MeOH (2 mL). The desired product was obtained as a colorless film (12 mg, 98% yield). ESI+MS: m/z=259.00 (M+1)$^+$; ESI-MS: m/z=256.80 (M–1)$^-$. $^1$H NMR (700 MHz, methanol-$d_4$) δ 3.44 (dd, J=13.0, 2.4 Hz, 1H), 2.82 (dd, J=12.9, 11.5 Hz, 1H), 2.79 (s, 3H), 2.35-2.31 (m, 1H), 2.30-2.23 (m, 1H), 2.11-2.06 (m, 1H), 2.01-1.96 (m, 1H), 1.97-1.89 (m, 1H), 1.70 (ddd, J=26.2, 13.4, 3.5 Hz, 1H), 1.46-1.40 (m, 3H), 1.04 (qd, J=13.2, 3.7 Hz, 1H), 0.92-0.80 (m, 2H).

Step D. (1R,2S,5R)-5-(2-Boronoethyl)-2-(((S)-2-((tert-butoxycarbonyl)amino)propanamido)methyl)-1-(methylamino)cyclohexane-1-carboxylic acid The title compound was obtained in the same manner as in Example 1, step E, using (1R,2S,5R)-2-(aminomethyl)-5-(2-boronoethyl)-1-(methylamino)cyclohexane-1-carboxylic acid dihydrochloride (11 mg, 0.03 mmol), Boc-L-Ala-OSu (10.5 mg, 0.04 mmol), TEA (23 µL, 0.17 mmol) and DMF (1 mL). The residue was purified by preparative HPLC (1-55% of acetonitrile in water) to give the corresponding product (13 mg, 64% yield, white solid). ESI+MS: m/z=430.00 (M+1)$^+$; ESI-MS: m/z=427.90 (M–1)$^-$. $^1$H NMR (700 MHz, methanol-$d_4$) δ 3.99 (q, J=7.2 Hz, 1H), 3.68-3.60 (m, 1H), 2.80-2.73 (m, 1H), 2.71 (s, 3H), 2.25-2.14 (m, 1H), 2.09 (dd, J=12.5, 2.4 Hz, 1H), 1.90-1.72 (m, 4H), 1.53-1.50 (m, 1H), 1.48 (s, 9H), 1.37-1.28 (m, 5H), 1.08 (t, J=12.2 Hz, 1H), 0.87-0.78 (m, 2H).

Step E. (1R,2S,5R)-2-(((S)-2-Aminopropanamido) methyl)-5-(2-boronoethyl)-1-(methylamino)cyclo-hexane-1-carboxylic acid dihydrochloride The title compound was obtained in the same manner as in Example 3, step B, using (1R,2S,5R)-5-(2-boronoethyl)-2-(((S)-2-((tert-butoxycarbonyl)amino)propanamido) methyl)-1-(methylamino)cyclohexane-1-carboxylic acid (8 mg, 0.02 mmol) and 2 M $HCl_{aq}$ (1 mL). The crude material was purified by preparative HPLC (0.1-15% of acetonitrile in water) to give the corresponding product (5.8 mg, 76% yield, white solid). ESI+MS: m/z=329.95 (M+1)$^+$; ESI-MS: m/z=327.85 (M−1)$^-$. $^1$H NMR (700 MHz, deuterium oxide) δ 4.10 (q, J=7.1 Hz, 1H), 3.68 (dd, J=13.9, 2.6 Hz, 1H), 2.94 (dd, J=14.0, 9.7 Hz, 1H), 2.77 (s, 3H), 2.22 (dd, J=12.9, 3.2 Hz, 1H), 2.06-1.95 (m, 1H), 1.95-1.84 (m, 3H), 1.64-1.53 (m, 4H), 1.45-1.34 (m, 2H), 1.24 (t, J=12.5 Hz, 1H), 0.99-0.88 (m, 1H), 0.87-0.78 (m, 2H).

Human Arginase Inhibition Assay

The inhibitory activities of the compounds of the invention were assessed using recombinant human arginases 1 and 2. Both enzymes were biosynthesized using a prokaryotic expression system (*E. coli*) and purified by fast protein liquid chromatography (FPLC). The compounds were screened in 96-well plates at the total reaction volume of 100 μL. Briefly, recombinant enzymes were incubated with the tested compounds for 1 h at 37° C. in the reaction buffer (100 mM sodium phosphate buffer, 130 mM NaCl, 1 mg/mL BSA, pH 7.4) containing substrate (L-arginine hydrochloride, 10 mM for hARG1 and 20 mM for hARG2) and cofactor (200 μM $MnCl_2$). The assay is based on the detection of urea, which is generated during the conversion of L-arginine into L-omithine catalyzed by ARG1 or ARG2 (Baggio et al. *J Pharmacol. Exp. Ther.* 1999, 290, 1409-1416). The colorimetrically detectable product was developed by adding a mixture of reagent A (4 mM oPA, 50 mM boric acid, 1 M sulfuric acid, 0.03% Brij-35) and reagent B (4 mM NED, 50 mM boric acid, 1 M sulfuric acid, 0.03% Brij-35) in equal proportions. The absorbance for each well was measured at 515 nm and the enzyme inhibition was calculated. The urea production in the absence of any tested compound was considered as maximal enzyme activity. The absorbance at the absence of arginase (background) was subtracted from all the values. The normalized values were analyzed using GraphPad Prism 7.0 software by plotting inhibition curves and determining the $IC_{50}$ values.

The calculated $IC_{50}$ values were divided into the following classes:

A=1-99 nM; B=100-199 nM; C=200-299 nM; and D>300 nM.

The inhibitory activity classes of the hydrochloride salts of the exemplary compounds according to the invention are presented in Table 1

TABLE 1

| Example No. | Compound Structure | Activity Class (ARG I) | Activity Class (ARG II) |
|---|---|---|---|
| 1 | | B | D |
| 2 | | B | C |
| 3 | | D | D |
| 4 | | A | D |
| 5 | | A | D |

TABLE 1-continued

| Example No. | Compound Structure | Activity Class (ARG I) | Activity Class (ARG II) |
|---|---|---|---|
| 6 | ×2 HCl | A | B |
| 7 | ×2 HCl | B | D |
| 8 | ×3 HCl | B | D |
| 9 | ×3 HCl | A | D |
| 10 | ×2 HCl | A | D |
| 11 | ×2 HCl | A | B |
| 12 | ×2 HCl | A | C |
| 13 | ×3 HCl | A | D |
| 14 | ×2 HCl | C | D |

TABLE 1-continued

| Example No. | Compound Structure | Activity Class (ARG I) | Activity Class (ARG II) |
|---|---|---|---|
| 15 | ×2 HCl | C | D |
| 16 | ×2 HCl | B | D |
| 17 | ×2 HCl | A | C |
| 18 | ×2 HCl | B | D |
| 19 | ×2 HCl | B | D |
| 20 | ×2 HCl | A | D |
| 21 | ×2 HCl | C | D |
| 22 | ×2 HCl | A | D |

TABLE 1-continued

| Example No. | Compound Structure | Activity Class (ARG I) | Activity Class (ARG II) |
|---|---|---|---|
| 23 | | A | D |
| 24 | | B | D |
| 25 | | A | D |
| 26 | | B | D |
| 27 | | C | D |
| 28 | | B | D |
| 29 | | D | D |
| 30 | | D | D |
| 31 | | B | D |

TABLE 1-continued

| Example No. | Compound Structure | Activity Class (ARG I) | Activity Class (ARG II) |
|---|---|---|---|
| 32 | | D | D |
| 33 | | B | D |
| 34 | | D | D |
| 35 | | D | D |
| 36 | | D | D |

To illustrate the lower cellular activity of the compounds according to the invention versus arginase inhibitors disclosed in U.S. Ser. No. 10/391,077 B2, the selected examples were tested in cell-based assay using murine primary macrophages. Lower intracellular activity observed for the compounds according to the invention may potentially result in lower hepatotoxicity compared to the arginase inhibitors disclosed in U.S. Ser. No. 10/391,077 B2.

Cell-Based Assay

Efficacy of Selected Examples Towards Intracellular Arginase in Macrophages Isolated from Murine Bone Marrow— Bone Marrow Derived Macrophages (BMDM)

Background: Macrophages are the most specialized phagocytic cells, and acquire specific phenotypes and functions in response to a variety of external triggers as a consequence of adaptation to local tissue environmental cues. Th1 pro-inflammatory cytokines such as IL-2, IL-12, IFN-γ, TNF-α and β, lead to the activation of macrophages towards the so-called classical inflammatory phenotype (CAMs or M1 macrophages). On the other hand, Th2 cytokines such as IL-4 and IL-13 as well as anti-inflammatory molecules like IL-10 and TGF-β activate macrophages towards an alternative phenotype (AAMs or M2 macrophages) (Murray and Wynn, 2011, *Nat Rev Immunol* 11(11): 723-737. Hoeksema, Stoger, et al. 2012, *Curr Atheroscler Rep* 14(3): 254-263). The M1/M2 macrophages use different metabolic pathways for arginine degradation. The preference of macrophages to metabolize arginine via nitric oxide synthase (NOS) to NO and citrulline or via arginase to ornithine and urea defines them as M1 (NOS) or M2 (arginase) respectively (Mills 2012, *Crit Rev Immunol* 32(6): 463-488).

Macrophages are a dominant leukocyte population infiltrating the tumor and play a critical role in modulating the tumor microenvironment. It has been shown that tumor-associated macrophages (TAMs) exhibit a similar phenotype to M2 macrophages and their accumulation in tumor correlates with a poor clinical outcome (Chanmee, Ontong et al. 2014, *Cancers* (Basel) 6(3): 1670-1690).

Murine bone marrow-derived or peritoneal macrophages comprise a convenient in vitro model that enables differentiation of these cells towards M1 or M2 macrophages and further use for the study.

Materials & Methods: The assay was performed according to modified literature protocol (Pineda-Torra I et al., *Methods Mol Biol.* 2015; 1339:101-9. Mia S et al., *Scand J Immunol.* 2014 May; 79(5):305-14). The femurs and tibias were isolated from C57BL/6 mice. Bones were cleaned from all attached tissues by using a sterile swab without affecting the bone structure. The sides of the bones were cut off and flush with cold sterile PBS by using 26-G needle S into a 50 mL sterile tube with a cell strainer (Falcon™, Cat. No. U00149), until the bone cavity appeared white. Then, the cells were centrifuged (5 min at 500×G, 4° C.), washed twice with PBS and counted. Cells were plated in Petri dish in density of $1\times10^6$/mL and cultured in DMEM (Gibco, Cat. No. 31331-029) with 10% FBS, 1% pen-strep and 50 ng/mL M-CSF (PeproTech, Cat. No. 315-02), (37° C., 5% $CO_2$). After five days cells were subcultured into P96 plate (BD, Cat. No. 353072) at the density of 64,000 cells/well in medium supplemented with 50 ng/mL M-CSF, 20 ng/mL TGF-β and 30 ng/mL IL-4 (Biomibo Cat. No. 214-1). One day later exemplary compounds (dissolved in PBS) were added in several different concentrations and 24 hours later the level of urea was measured in the culture medium in each well (Jung D et al., *Clin Chem.* 1975, 21(8):1136-40). The concentration of urea in the absence of any compound was considered as the maximum enzyme activity. The absorbance of cell culture media (background) was subtracted from all the values.

The $IC_{50}$ values were calculated using GraphPad Prism 7.0. and assigned into the following classes: A=10-100 µM; and B>100 µM.

The inhibitory activity classes of the exemplary compounds according to the invention are presented in Table 2

TABLE 2

| Example No. | Activity class (BMDM) |
|---|---|
| 2 | A |
| 3 | B |
| 4 | B |
| 5 | B |
| 6 | A |
| 9 | B |
| 10 | B |
| 12 | B |
| 13 | B |
| 17 | A |

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is sufficient to enable one skilled in the art to practice the invention. The present invention is not to be limited in scope by the examples provided, since each of the examples is intended as a single illustration of one aspect of the invention—other functionally equivalent embodiments are within the scope of the invention. Various modifications of the invention in addition to those shown and described herein will become apparent to those skilled in the art from the foregoing description and fall within the scope of the appended claims. All of the many advantages and objects of the invention are not necessarily encompassed by each embodiment of the invention.

The invention claimed is:
1. A compound of the formula or a pharmaceutically acceptable salt thereof, wherein:
$R^8$ is selected from the group consisting of D-alanyl, L-alanyl, L-arginyl, L-asparaginyl, glycyl, L-histidyl, L-isoleucyl, L-leucyl, L-tert-leucyl, L-lysyl, L-methionyl, L-norvalyl, L-phenylalanyl, L-prolyl, L-seryl, L-threonyl, L-tryptophanyl, L-tyrosyl, D-valyl, L-valyl, (S)-2-amino-2-cyclopentylacetyl, (S)-2-amino-3-hydroxy-3-methylbutyryl, and (S)-2-amino-2,3-dimethylbutyryl; and
$R^9$ is hydrogen or methyl.

2. The compound according to claim 1, wherein the compound is:
(1R,2S,5R)-1-amino-2-(((S)-2-aminopropanamido)methyl)-5-(2-boronoethyl)cyclohexane-1-carboxylic acid;
(1R,2S,5R)-1-amino-2-(((S)-2-amino-3-methylbutanamido)methyl)-5-(2-boronoethyl)cyclohexane-1-carboxylic acid;
(1R,2S,5R)-1-amino-2-(((S)-2-amino-3-phenylpropanamido)methyl)-5-(2-boronoethyl)cyclohexane-1-carboxylic acid;
(1R,2S,5R)-1-amino-2-((2-aminoacetamido)methyl)-5-(2-boronoethyl)cyclohexane-1-carboxylic acid;
(1R,2S,5R)-1-amino-5-(2-boronoethyl)-2-(((S)-pyrrolidine-2-carboxamido)methyl)cyclohexane-1-carboxylic acid;
(1R,2S,5R)-1-amino-2-(((S)-2-amino-4-methylpentanamido)methyl)-5-(2-boronoethyl)cyclohexane-1-carboxylic acid;
(1R,2S,5R)-1-amino-2-(((S)-2-amino-3-hydroxypropanamido)methyl)-5-(2-boronoethyl)cyclohexane-1-carboxylic acid;
(1R,2S,5R)-1-amino-2-(((S)-2-amino-3-(1H-imidazol-4-yl)propanamido)methyl)-5-(2-boronoethyl)cyclohexane-1-carboxylic acid
(1R,2S,5R)-1-amino-5-(2-boronoethyl)-2-(((S)-2,6-diaminohexanamido)methyl)cyclohexane-1-carboxylic acid;
(1R,2S,5R)-1-amino-2-(((2S,3S)-2-amino-3-methylpentanamido)methyl)-5-(2-boronoethyl)cyclohexane-1-carboxylic acid;
(1R,2S,5R)-1-amino-2-(((S)-2-amino-2-cyclopentylacetamido)methyl)-5-(2-boronoethyl)cyclohexane-1-carboxylic acid;

(1R,2S,5R)-1-amino-2-(((S)-2-amino-3,3-dimethylbu-tanamido)methyl)-5-(2-boronoethyl)cyclohexane-1-carboxylic acid;

(1R,2S,5R)-1-amino-2-(((S)-2-amino-5-guanidinopen-tanamido)methyl)-5-(2-boronoethyl)cyclohexane-1-carboxylic acid;

(1R,2S,5R)-1-amino-2-(((S)-2-amino-3-(4-hydroxyphe-nyl)propanamido)methyl)-5-(2-boronoethyl)cyclo-hexane-1-carboxylic acid;

(1R,2S,5R)-1-amino-5-(2-boronoethyl)-2-(((S)-2,4-di-amino-4-oxobutanamido)methyl)cyclohexane-1-car-boxylic acid;

(1R,2S,5R)-1-amino-2-(((S)-2-amino-3-hydroxy-3-meth-ylbutanamido)methyl)-5-(2-boronoethyl)cyclohexane-1-carboxylic acid;

(1R,2S,5R)-1-amino-2-(((S)-2-amino-4-(methylthio)bu-tanamido)methyl)-5-(2-boronoethyl)cyclohexane-1-carboxylic acid;

(1R,2S,5R)-1-amino-2-(((S)-2-amino-3-(1H-indol-3-yl)propanamido)methyl)-5-(2-boronoethyl)cyclohexane-1-carboxylic acid;

(1R,2S,5R)-1-amino-2-(((2S,3R)-2-amino-3-hydroxybu-tanamido)methyl)-5-(2-boronoethyl)cyclohexane-1-carboxylic acid;

(1R,2S,5R)-1-amino-2-(((S)-2-aminopentanamido)methyl)-5-(2-boronoethyl)cyclohexane-1-carboxylic acid;

(1R,2S,5R)-1-amino-2-((2-amino-2,3-dimethylbutana-mido)methyl)-5-(2-boronoethyl)cyclohexane-1-car-boxylic acid;

(1R,2S,5R)-1-amino-2-(((R)-2-aminopropanamido)methyl)-5-(2-boronoethyl)cyclohexane-1-carboxylic acid;

(1R,2S,5R)-1-amino-2-(((R)-2-amino-3-methylbutana-mido)methyl)-5-(2-boronoethyl)cyclohexane-1-car-boxylic acid;

(1R,2S,5R)-1-amino-2-(((S)-2-amino-N-methylpropana-mido)methyl)-5-(2-boronoethyl)cyclohexane-1-car-boxylic acid;

(1R,2S,5R)-1-amino-2-(((S)-2-amino-N,3-dimethylbu-tanamido)methyl)-5-(2-boronoethyl)cyclohexane-1-carboxylic acid;

(1R,2S,5R)-1-amino-2-(((R)-2-amino-3-(1-methyl-1H-indol-3-yl)propanamido)methyl)-5-(2-boronoethyl)cy-clohexane-1-carboxylic acid;

(1R,2S,5R)-1-amino-2-(((R)-2-amino-3-mercaptopro-panamido)methyl)-5-(2-boronoethyl)cyclohexane-1-carboxylic acid;

(1R,2S,5R)-1-amino-5-(2-boronoethyl)-2-(((S)-2,5-di-amino-5-oxopentanamido)methyl)cyclohexane-1-car-boxylic acid;

(1R,2S,5R)-1-amino-2-(((S)-2-amino-3-carboxypropana-mido)methyl)-5-(2-boronoethyl)cyclohexane-1-car-boxylic acid;

(1R,2S,5R)-1-amino-2-(((S)-2-amino-4-carboxybutana-mido)methyl)-5-(2-boronoethyl)cyclohexane-1-car-boxylic acid;

(1R,2S,5R)-1-amino-5-(2-boronoethyl)-2-((2-(methyl-amino)acetamido)methyl)cyclohexane-1-carboxylic acid;

(2-((1R,3R,4S)-3-amino-4-(((S)-2-amino-3-methylbu-tanamido)methyl)-3-(methoxycarbonyl)cyclohexyl)ethyl)boronic acid;

(1R,2S,5R)-2-(((S)-2-aminopropanamido)methyl)-5-(2-boronoethyl)-1-(ethylamino)cyclohexane-1-carboxylic acid; or (1R,2S,5R)-2-(((S)-2-aminopropanamido)methyl)-5-(2-boronoethyl)-1-(methylamino)cyclohexane-1-carbox-ylic acid.

3. The compound according to claim 2, wherein the compound is:

(1R,2S,5R)-1-amino-2-((2-aminoacetamido)methyl)-5-(2-boronoethyl)cyclohexane-1-carboxylic acid;

(1R,2S,5R)-1-amino-5-(2-boronoethyl)-2-(((S)-pyrroli-dine-2-carboxamido)methyl)cyclohexane-1-carboxylic acid;

(1R,2S,5R)-1-amino-2-(((S)-2-amino-4-methylpentana-mido)methyl)-5-(2-boronoethyl)cyclohexane-1-car-boxylic acid;

(1R,2S,5R)-1-amino-5-(2-boronoethyl)-2-(((S)-2,6-di-aminohexanamido)methyl)cyclohexane-1-carboxylic acid;

(1R,2S,5R)-1-amino-2-(((2S,3S)-2-amino-3-methylpen-tanamido)methyl)-5-(2-boronoethyl)cyclohexane-1-carboxylic acid;

(1R,2S,5R)-1-amino-2-(((S)-2-amino-2-cyclopentylacet-amido)methyl)-5-(2-boronoethyl)cyclohexane-1-car-boxylic acid;

(1R,2S,5R)-1-amino-2-(((S)-2-amino-3,3-dimethylbu-tanamido)methyl)-5-(2-boronoethyl)cyclohexane-1-carboxylic acid;

(1R,2S,5R)-1-amino-2-(((S)-2-amino-5-guanidinopen-tanamido)methyl)-5-(2-boronoethyl)cyclohexane-1-carboxylic acid;

(1R,2S,5R)-1-amino-2-(((S)-2-amino-4-(methylthio)bu-tanamido)methyl)-5-(2-boronoethyl)cyclohexane-1-carboxylic acid;

(1R,2S,5R)-1-amino-2-(((S)-2-aminopentanamido)methyl)-5-(2-boronoethyl)cyclohexane-1-carboxylic acid;

(1R,2S,5R)-1-amino-2-(((R)-2-aminopropanamido)methyl)-5-(2-boronoethyl)cyclohexane-1-carboxylic acid; or (1R,2S,5R)-1-amino-2-(((S)-2-amino-3-methylbutana-mido)methyl)-5-(2-boronoethyl)cyclohexane-1-car-boxylic acid;

or a tautomer, stereoisomer, pharmaceutically acceptable salt, and/or a solvate thereof.

4. A pharmaceutical composition comprising (i) a thera-peutically effective amount of at least one compound according to claim 1, or a tautomer, stereoisomer, pharma-ceutically acceptable salt, and/or a solvate thereof; and (ii) a pharmaceutically acceptable carrier, vehicle or excipient therefor.

5. A compound according to claim 1 which is (1R,2S,5R)-1-Amino-2-(((S)-2-aminopropanamido)methyl)-5-(2-boronoethyl)cyclohexane-1-carboxylic acid;

(1R,2S,5R)-1-Amino-2-(((S)-2-amino-3-methylbutana-mido)methyl)-5-(2-boronoethyl)cyclohexane-1-car-boxylic acid;

(1R,2S,5R)-1-Amino-2-(((S)-2-amino-3-phenylpropana-mido)methyl)-5-(2-boronoethyl)cyclohexane-1-car-boxylic acid;

(1R,2S,5R)-1-Amino-2-((2-aminoacetamido)methyl)-5-(2-boronoethyl)cyclohexane-1-carboxylic acid;

(1R,2S,5R)-1-Amino-5-(2-boronoethyl)-2-(((S)-pyrroli-dine-2-carboxamido)methyl)cyclohexane-1-carboxylic acid;

(1R,2S,5R)-1-Amino-2-(((S)-2-amino-4-methylpentana-mido)methyl)-5-(2-boronoethyl)cyclohexane-1-car-boxylic acid;

(1R,2S,5R)-1-Amino-5-(2-boronoethyl)-2-(((S)-2,6-di-aminohexanamido)methyl)cyclohexane-1-carboxylic acid;

(1R,2S,5R)-1-Amino-2-(((2S,3S)-2-amino-3-methylpen-tanamido)methyl)-5-(2-boronoethyl)cyclohexane-1-carboxylic acid;

(1R,2S,5R)-1-Amino-2-(((S)-2-amino-3,3-dimethylbu-tanamido)methyl)-5-(2-boronoethyl)cyclohexane-1-carboxylic acid;

(1R,2S,5R)-1-Amino-2-(((S)-2-amino-5-guanidinopen-tanamido)methyl)-5-(2-boronoethyl)cyclohexane-1-carboxylic acid;

(1R,2S,5R)-1-Amino-2-(((S)-2-amino-4-(methylthio)bu-tanamido)methyl)-5-(2-boronoethyl)cyclohexane-1-carboxylic acid; or a pharmaceutically acceptable salt thereof.

6. A compound according to claim 1 which is (1R,2S,5R)-1-Amino-2-(((S)-2-amino-3-phenylpropana-mido)methyl)-5-(2-boronoethyl)cyclohexane-1-car-boxylic acid;

(1R,2S,5R)-1-Amino-2-((2-aminoacetamido)methyl)-5-(2-boronoethyl)cyclohexane-1-carboxylic acid;

(1R,2S,5R)-1-Amino-5-(2-boronoethyl)-2-(((S)-pyrroli-dine-2-carboxamido)methyl)cyclohexane-1-carboxylic acid;

(1R,2S,5R)-1-Amino-5-(2-boronoethyl)-2-(((S)-2,6-di-aminohexanamido)methyl)cyclohexane-1-carboxylic acid;

(1R,2S,5R)-1-Amino-2-(((2S,3S)-2-amino-3-methylpen-tanamido)methyl)-5-(2-boronoethyl)cyclohexane-1-carboxylic acid;

(1R,2S,5R)-1-Amino-2-(((S)-2-amino-3,3-dimethylbu-tanamido)methyl)-5-(2-boronoethyl)cyclohexane-1-carboxylic acid;

(1R,2S,5R)-1-Amino-2-(((S)-2-amino-5-guanidinopen-tanamido)methyl)-5-(2-boronoethyl)cyclohexane-1-carboxylic acid; or a pharmaceutically acceptable salt thereof.

7. A compound according to claim 1 which is (1R,2S,5R)-1-amino-2-(((S)-2-aminopropanamido) methyl)-5-(2-boronoethyl)cyclohexane-1-carboxylic acid.

8. A compound according to claim 1 which is (1R,2S,5R)-1-amino-2-(((S)-2-amino-3-methylbutana-mido)methyl)-5-(2-boronoethyl)cyclohexane-1-car-boxylic acid.

9. A compound according to claim 1 which is (1R,2S,5R)-1-amino-2-(((2S,3S)-2-amino-3-methylpen-tanamido)methyl)-5-(2-boronoethyl)cyclohexane-1-carboxylic acid.

10. A compound according to claim 1 which is (1R,2S,5R)-1-amino-2-(((S)-2-amino-5-guanidinopen-tanamido)methyl)-5-(2-boronoethyl)cyclohexane-1-carboxylic acid.

* * * * *